(12) United States Patent
Shachar

(10) Patent No.: US 8,027,714 B2
(45) Date of Patent: Sep. 27, 2011

(54) APPARATUS AND METHOD FOR SHAPED MAGNETIC FIELD CONTROL FOR CATHETER, GUIDANCE, CONTROL, AND IMAGING

(75) Inventor: Yehoshua Shachar, Santa Monica, CA (US)

(73) Assignee: Magnetecs, Inc., Inglewood, CA (US)

( * ) Notice: Subject to any disclaimer, the term of this patent is extended or adjusted under 35 U.S.C. 154(b) by 879 days.

(21) Appl. No.: 11/140,475

(22) Filed: May 27, 2005

(65) Prior Publication Data

US 2007/0016006 A1 Jan. 18, 2007

(51) Int. Cl.
*A61B 5/05* (2006.01)
*A61B 5/06* (2006.01)
(52) U.S. Cl. .................... 600/424; 600/409; 600/411
(58) Field of Classification Search ................. 600/114, 600/117, 407, 424, 427, 585; 128/899; 361/141, 361/143, 146; 606/1, 108, 130; 251/129.15, 251/129.19, 129.21; 335/78, 81, 229, 245, 335/260
See application file for complete search history.

(56) References Cited

U.S. PATENT DOCUMENTS

| | | | | |
|---|---|---|---|---|
| 3,043,309 A | * | 7/1962 | McCarthy | 604/540 |
| 3,358,676 A | * | 12/1967 | Frei et al. | 600/12 |
| 3,622,869 A | | 11/1971 | Golay | |
| 3,628,527 A | | 12/1971 | West | |
| 3,746,937 A | * | 7/1973 | Koike | 318/122 |
| 3,961,632 A | | 6/1976 | Moossun | |

(Continued)

FOREIGN PATENT DOCUMENTS

DE 102005045073 A1 3/2007
(Continued)

OTHER PUBLICATIONS

Ishiyama, K.;Sendoh, M.;Arai, K.I.; Magnetic micromachines for medical applications. Journal of Magnetism and Magnetic Materials. 2002; vol. 242; pp. 41-46.*

(Continued)

*Primary Examiner* — Long V. Le
*Assistant Examiner* — Angela M Hoffa
(74) *Attorney, Agent, or Firm* — Knobbe, Martens, Olson & Bear, LLP

(57) ABSTRACT

A variable magnet system for manipulating a magnetic catheter is described. In one embodiment, a cluster of electromagnets is configured to generate a desired magnetic field. In one embodiment, one or more poles of the cluster are moveable with respect to other poles in the cluster to allow shaping of the magnetic field. In one embodiment, one or more magnetic poles can be extended or retracted to shape the magnetic field. In one embodiment, the electromagnets can be positioned to generate magnetic fields that exert a desired torque and/or movement force on the catheter. In one embodiment, the catheter guidance system includes a closed-loop servo feedback system. In one embodiment, a radar system is used to determine the location of the distal end of the catheter inside the body, thus, minimizing or eliminating the use of ionizing radiation such as X-rays. The catheter guidance system can also be used in combination with an X-ray system (or other imaging systems) to provide additional imagery to the operator. The magnetic system used in the magnetic catheter guidance system can also be used to locate the catheter tip to provide location feedback to the operator and the control system. In one embodiment, a magnetic field source is used to create a magnetic field of sufficient strength and orientation to move a magnetically-responsive catheter tip in a desired direction by a desired amount.

33 Claims, 62 Drawing Sheets

U.S. PATENT DOCUMENTS

| | | | |
|---|---|---|---|
| 4,063,561 A | 12/1977 | McKenna | |
| 4,096,862 A | 6/1978 | DeLuca | |
| 4,162,679 A | 7/1979 | Reenstierna | |
| 4,173,228 A | 11/1979 | Van Steenwyk et al. | |
| 4,244,362 A * | 1/1981 | Anderson | 128/200.26 |
| 4,249,536 A | 2/1981 | Vega | |
| 4,270,252 A | 6/1981 | Harrison et al. | |
| 4,292,961 A | 10/1981 | Kawashima | |
| 4,354,501 A | 10/1982 | Colley et al. | |
| 4,392,634 A * | 7/1983 | Kita | 251/129.19 |
| 4,671,287 A | 6/1987 | Fiddian-Green | |
| 4,727,344 A * | 2/1988 | Koga et al. | 335/78 |
| 4,735,211 A | 4/1988 | Takasugi | |
| 4,809,713 A * | 3/1989 | Grayzel | 607/116 |
| 4,869,247 A | 9/1989 | Howard, III et al. | |
| 4,870,306 A | 9/1989 | Petersen | |
| 4,943,770 A | 7/1990 | Ashley-Rollman et al. | |
| 4,984,581 A | 1/1991 | Stice | |
| 4,985,015 A | 1/1991 | Obermann et al. | |
| 5,031,634 A | 7/1991 | Simon | |
| 5,063,935 A | 11/1991 | Gambale | |
| 5,083,562 A | 1/1992 | de Coriolis et al. | |
| 5,090,956 A | 2/1992 | McCoy | |
| 5,125,888 A | 6/1992 | Howard et al. | |
| 5,167,626 A | 12/1992 | Casper et al. | |
| 5,209,234 A | 5/1993 | LaRocca | |
| 5,226,847 A | 7/1993 | Thomas et al. | |
| 5,249,163 A | 9/1993 | Erickson | |
| 5,255,680 A | 10/1993 | Darrow et al. | |
| 5,257,636 A | 11/1993 | White | |
| 5,269,759 A | 12/1993 | Hernandez et al. | |
| 5,353,807 A * | 10/1994 | DeMarco | 600/585 |
| 5,377,678 A | 1/1995 | Dumoulin et al. | |
| 5,396,902 A | 3/1995 | Brennen et al. | |
| 5,462,054 A | 10/1995 | Rapoport et al. | |
| 5,485,748 A | 1/1996 | Zeamer | |
| 5,492,131 A | 2/1996 | Galel | |
| 5,546,948 A | 8/1996 | Hamm et al. | |
| 5,550,469 A * | 8/1996 | Tanabe et al. | 324/251 |
| 5,558,091 A | 9/1996 | Acker et al. | |
| 5,573,012 A | 11/1996 | McEwan | |
| 5,588,442 A | 12/1996 | Scovil et al. | |
| 5,624,430 A | 4/1997 | Eton et al. | |
| 5,645,065 A | 7/1997 | Shapiro et al. | |
| 5,650,725 A | 7/1997 | Powell et al. | |
| 5,654,864 A * | 8/1997 | Ritter et al. | 361/141 |
| 5,656,030 A | 8/1997 | Hunjan et al. | |
| 5,681,260 A * | 10/1997 | Ueda et al. | 600/114 |
| 5,683,384 A | 11/1997 | Gough et al. | |
| 5,702,433 A | 12/1997 | Taylor et al. | |
| 5,704,897 A | 1/1998 | Truppe | |
| 5,709,661 A | 1/1998 | Van Egmond et al. | |
| 5,711,299 A | 1/1998 | Manwaring et al. | |
| 5,769,843 A | 6/1998 | Abela et al. | |
| 5,775,322 A | 7/1998 | Silverstein et al. | |
| 5,779,694 A * | 7/1998 | Howard et al. | 604/891.1 |
| 5,808,665 A | 9/1998 | Green | |
| 5,821,920 A | 10/1998 | Rosenberg et al. | |
| 5,843,153 A * | 12/1998 | Johnston et al. | 607/122 |
| 5,844,140 A | 12/1998 | Seale | |
| 5,851,185 A | 12/1998 | Berns | |
| 5,904,691 A | 5/1999 | Barnett et al. | |
| 5,919,135 A | 7/1999 | Lemuelson | |
| 5,931,818 A | 8/1999 | Werp et al. | |
| 5,971,976 A * | 10/1999 | Wang et al. | 606/1 |
| 6,014,580 A * | 1/2000 | Blume et al. | 600/424 |
| 6,015,414 A * | 1/2000 | Werp et al. | 606/108 |
| 6,038,488 A | 3/2000 | Barnes et al. | |
| 6,104,944 A * | 8/2000 | Martinelli | 600/424 |
| 6,122,538 A | 9/2000 | Sliwa et al. | |
| 6,128,174 A | 10/2000 | Ritter et al. | |
| 6,129,668 A | 10/2000 | Haynor et al. | |
| 6,148,823 A | 11/2000 | Hastings | |
| 6,152,933 A | 11/2000 | Werp et al. | |
| 6,157,853 A | 12/2000 | Blume et al. | |
| 6,200,312 B1 | 3/2001 | Zikorous et al. | |
| 6,241,671 B1 * | 6/2001 | Ritter et al. | 600/427 |
| 6,292,678 B1 * | 9/2001 | Hall et al. | 600/374 |
| 6,295,466 B1 | 9/2001 | Ishikawa et al. | |
| 6,296,604 B1 | 10/2001 | Garibaldi et al. | |
| 6,298,257 B1 * | 10/2001 | Hall et al. | 600/407 |
| 6,304,768 B1 | 10/2001 | Blume et al. | |
| 6,311,082 B1 * | 10/2001 | Creighton et al. | 600/407 |
| 6,314,312 B1 | 11/2001 | Wessels et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,381,485 B1 | 4/2002 | Hunter et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,454,776 B1 | 9/2002 | Tajima et al. | |
| 6,459,924 B1 * | 10/2002 | Creighton et al. | 600/427 |
| 6,459,926 B1 | 10/2002 | Nowlin et al. | |
| 6,475,223 B1 | 11/2002 | Werp et al. | |
| 6,505,062 B1 | 1/2003 | Ritter et al. | |
| 6,507,751 B2 | 1/2003 | Blume et al. | |
| 6,522,909 B1 * | 2/2003 | Garibaldi et al. | 600/424 |
| 6,524,303 B1 | 2/2003 | Garibaldi | |
| 6,529,761 B2 * | 3/2003 | Creighton et al. | 600/407 |
| 6,537,196 B1 | 3/2003 | Creighton, IV et al. | |
| 6,562,019 B1 | 5/2003 | Sell | |
| 6,575,977 B1 | 6/2003 | Michelson | |
| 6,587,709 B2 | 7/2003 | Solf et al. | |
| 6,594,517 B1 | 7/2003 | Nevo | |
| 6,630,879 B1 | 10/2003 | Creighton, IV et al. | |
| 6,662,034 B2 | 12/2003 | Segner et al. | |
| 6,667,660 B2 | 12/2003 | Schrodinger et al. | |
| 6,669,693 B2 | 12/2003 | Friedman | |
| 6,677,752 B1 | 1/2004 | Creighton, IV et al. | |
| 6,702,804 B1 | 3/2004 | Ritter et al. | |
| 6,704,694 B1 | 3/2004 | Basdogan et al. | |
| 6,726,675 B1 | 4/2004 | Beyar | |
| 6,733,511 B2 | 5/2004 | Hall et al. | |
| 6,740,103 B2 | 5/2004 | Hall et al. | |
| 6,755,816 B2 | 6/2004 | Ritter et al. | |
| 6,776,165 B2 | 8/2004 | Jin | |
| 6,786,219 B2 | 9/2004 | Garibaldi et al. | |
| 6,817,364 B2 | 11/2004 | Garibaldi et al. | |
| 6,834,201 B2 | 12/2004 | Gillies et al. | |
| 6,853,965 B2 | 2/2005 | Massie et al. | |
| 6,902,528 B1 | 6/2005 | Garibaldi | |
| 6,914,552 B1 | 7/2005 | McEwan | |
| 6,960,847 B2 * | 11/2005 | Suzuki et al. | 310/14 |
| 7,280,863 B2 * | 10/2007 | Shachar | 600/424 |
| 7,316,700 B2 | 1/2008 | Alden et al. | |
| 7,341,063 B2 * | 3/2008 | Garibaldi et al. | 128/899 |
| 7,346,379 B2 * | 3/2008 | Eng et al. | 600/374 |
| 7,495,537 B2 * | 2/2009 | Tunay | 335/306 |
| 7,543,239 B2 * | 6/2009 | Viswanathan et al. | 715/772 |
| 7,751,867 B2 * | 7/2010 | Viswanathan | 600/424 |
| 7,769,427 B2 * | 8/2010 | Shachar | 600/424 |
| 7,869,854 B2 * | 1/2011 | Shachar et al. | 600/374 |
| 7,873,402 B2 * | 1/2011 | Shachar | 600/424 |
| 2001/0004215 A1 | 6/2001 | Kubota et al. | |
| 2001/0021805 A1 | 9/2001 | Blume et al. | |
| 2002/0022777 A1 * | 2/2002 | Criegthon et al. | 600/407 |
| 2002/0055674 A1 | 5/2002 | Ben-haim et al. | |
| 2002/0058866 A1 | 5/2002 | Segner et al. | |
| 2002/0103430 A1 | 8/2002 | Hastings et al. | |
| 2003/0114727 A1 | 6/2003 | Wallace | |
| 2003/0205941 A1 * | 11/2003 | Suzuki et al. | 310/49 R |
| 2003/0233112 A1 | 12/2003 | Alden et al. | |
| 2004/0019447 A1 * | 1/2004 | Shachar | 702/115 |
| 2004/0199074 A1 * | 10/2004 | Ritter et al. | 600/424 |
| 2004/0249262 A1 * | 12/2004 | Werp et al. | 600/411 |
| 2004/0249263 A1 * | 12/2004 | Creighton, IV | 600/411 |
| 2005/0044449 A1 | 1/2005 | Mitschke et al. | |
| 2005/0021078 A1 | 1/2005 | Vleugels et al. | |
| 2005/0096589 A1 | 5/2005 | Shachar | |
| 2005/0256521 A1 | 11/2005 | Kozel | |
| 2006/0114088 A1 | 6/2006 | Shachar | |
| 2006/0116633 A1 | 6/2006 | Shachar | |
| 2006/0116634 A1 | 6/2006 | Shachar | |
| 2006/0217697 A1 | 9/2006 | Lau et al. | |

| | | | |
|---|---|---|---|
| 2007/0016006 | A1 | 1/2007 | Shachar |
| 2007/0016131 | A1* | 1/2007 | Munger et al. ............. 604/95.05 |
| 2007/0062547 | A1 | 3/2007 | Pappone |
| 2007/0066880 | A1 | 3/2007 | Lee et al. |
| 2007/0197891 | A1 | 8/2007 | Shachar |
| 2008/0027313 | A1 | 1/2008 | Shachar |
| 2008/0039880 | A1 | 2/2008 | Nohilly et al. |
| 2008/0249395 | A1 | 10/2008 | Shachar et al. |
| 2008/0297287 | A1 | 12/2008 | Shachar et al. |
| 2009/0248014 | A1 | 10/2009 | Shachar et al. |
| 2009/0253985 | A1 | 10/2009 | Shachar et al. |
| 2009/0275828 | A1 | 11/2009 | Shachar et al. |
| 2010/0130854 | A1* | 5/2010 | Shachar et al. ............... 600/424 |
| 2010/0305402 | A1* | 12/2010 | Shachar et al. ............... 600/118 |
| 2010/0305429 | A1* | 12/2010 | Shachar et al. ............... 600/424 |

FOREIGN PATENT DOCUMENTS

| | | | |
|---|---|---|---|
| EP | 0147082 | A2 | 7/1985 |
| EP | 1 059 067 | | 12/2000 |
| EP | 1115327 | * | 7/2001 |
| GB | 2367803 | A | 4/2002 |
| JP | 2000-509316 | | 7/2000 |
| JP | 2001-448 | | 1/2001 |
| JP | 2001-509038 | | 7/2001 |
| JP | 2001-514040 | | 9/2001 |
| WO | WO 95-01757 | A1 | 1/1995 |
| WO | WO 97-29803 | A1 | 8/1997 |
| WO | WO 98-35720 | A2 | 8/1998 |
| WO | WO 99-11189 | A1 | 3/1999 |
| WO | WO 99-23934 | A2 | 5/1999 |
| WO | WO 9923934 | * | 5/1999 |
| WO | WO 00-07641 | A | 2/2000 |
| WO | WO 02-19908 | A | 3/2002 |
| WO | WO 02-34131 | A1 | 5/2002 |
| WO | WO 0234131 | * | 5/2002 |
| WO | WO 02-094115 | A2 | 11/2002 |
| WO | WO 02-094115 | A3 | 11/2002 |
| WO | WO 2004-006795 | A1 | 1/2004 |
| WO | WO 2005-042053 | A2 | 5/2005 |
| WO | WO 2005-042053 | A3 | 5/2005 |
| WO | WO 2005-112813 | A1 | 12/2005 |
| WO | WO 2007-100559 | A2 | 9/2007 |

OTHER PUBLICATIONS

Ritter, J.A.;Ebner, A.D.;Daniel, K.D.;Stewart, K.L.; Application of high gradient magnetic separation principles to magnetic drug targeting. Journal of Magnetism and Magnetic Materials. 2004; vol. 280; pp. 184-201.*
Totsu, K.;Haga,Y.;Esashi, M.; Three-axis magneto-impedance effect sensor system for detecting position and orientation of catheter tip. Sensors and Actuators. 2004; Issue A 111; pp. 304-309.*
Office Action dated Feb. 22, 2006 from Related U.S. Appl. No. 10/621,196.
Office Action dated Nov. 14, 2006 from Related U.S. Appl. No. 10/621,196.
Office Action dated Apr. 18, 2007 from Related U.S. Appl. No. 10/621,196.
Office Action dated May 18, 2006 from Related U.S. Appl. No. 10/690,472.
Office Action dated Jan. 30, 2007 from Related U.S. Appl. No. 10/690,472.
Notice of Allowance dated Aug. 6, 2007 from Related U.S. Appl. No. 10/690,472.
Office Action dated Feb. 5, 2008 from Related U.S. Appl. No. 10/621,196.
Office Action dated Sep. 10, 2007 from Related U.S. Appl. No. 10/621,196.
Advisory Action dated Nov. 6, 2007 from Related U.S. Appl. No. 10/621,196.
International Search Report from PCT/US2007/004416, Aug. 24, 2007, 5 pages.
Bergveld, Piet, "Development, Operation, and Application of the Ion-Sensitive Field-Effect Transistor as a Tool for Electrophysiology", IEEE Transactions on Biomedical Engineering, vol. BME-19, No. 5, Sep. 1972, 10 pages.
Office Action dated Dec. 2, 2008 from Related U.S. Appl. No. 10/621,196.
Office Action dated Jan. 29, 2009 from Related U.S. Appl. No. 11/331,781.
Office Action dated Feb. 25, 2009 from Related U.S. Appl. No. 11/331,944.
Office Action dated Apr. 28, 2009 from Related U.S. Appl. No. 11/331,485.
Office Action dated May 6, 2009 from Related U.S. Appl. No. 11/362,542.
International Search Report from PCT/US2009/039659, Jul. 6, 2009, 4 pages.
Office Action dated Jul. 15, 2009 From Related U.S. Appl. No. 11/331,485.
Office Action dated Jul. 13, 2009 from Related U.S. Appl. No. 11/362,542.
International Search Report from PCT/US2008/060525, Oct. 31, 2008, 6 pages.
Office Action dated Jul. 10, 2008 from Related U.S. Appl. No. 10/621,196.
Office Action dated Jun. 18, 2008, 2008 From Related U.S. Appl. No. 11/331,485.
Fink et al.,"An Optically Switched PS-Radar for Pictorial Representation of Object Structures in Human Tissue," Experimentelle Technik Der Physik, vol. 38, No. 3, 1990, pp. 197-206, 10 pages.
International Search Report from PCT/US2008/056277, Nov. 18, 2008, 5 pages.
Supplementary Partial Search Report from 04795885.5, Nov. 18, 2008, 5 pages.
Extended European Search Report from 09005296.0, Aug. 19, 2009, 3 pages.
Faddis et al., "Novel, Magnetically Guided Catheter for Endocardial Mapping and Radiofrequency Catheter Ablation," Journal of the American Heart Association, Nov. 11, 2002, pp. 2980-2985.
International Search Report from PCT Application No. PCT/US03/22122; 9 pages, Jun. 11, 2003.
Faddis et al., "Novel, Magnetically Guided Catheter for Endocardial Mapping and Radiofrequency Catheter Ablation," Journal of the American Heart Association, Nov. 11, 2002, Circulation, vol. 106, pp. 2980-2985.
International Search Report from PCT Application No. PCT/US03/22122; 9 pages.
Canadian Office Action for Application No. 2542863, dated Sep. 30, 2010.
International Search Report for PCT/US2010/036149, dated Sep. 29, 2010.
International Search Report for PCT/US2010/052684, dated Dec. 6, 2010.
International Search Report for PCT/US2010/052696, dated Dec. 8, 2010.
Materials Library in FEMM 4.0, May 18, 2007, pp. 3-4.
Standard Specifications for Permanent Magnet Materials, Magnetic Materials Producers Association, 1964.

* cited by examiner

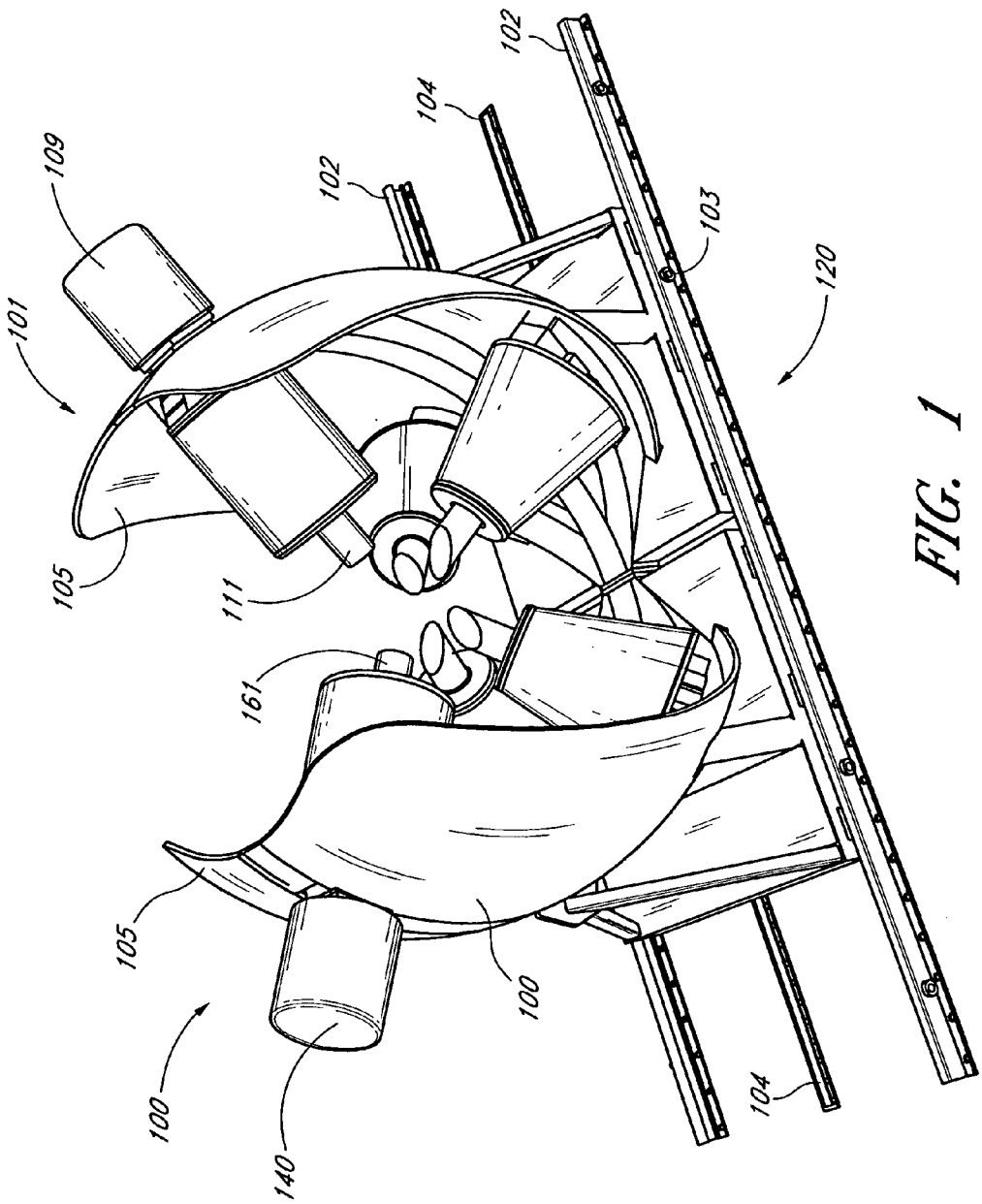

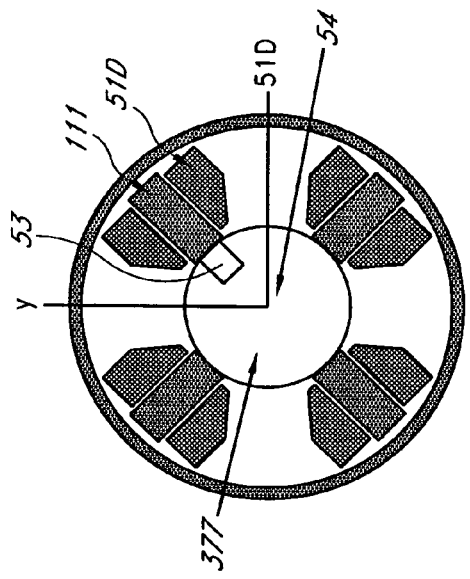
FIG. 3A
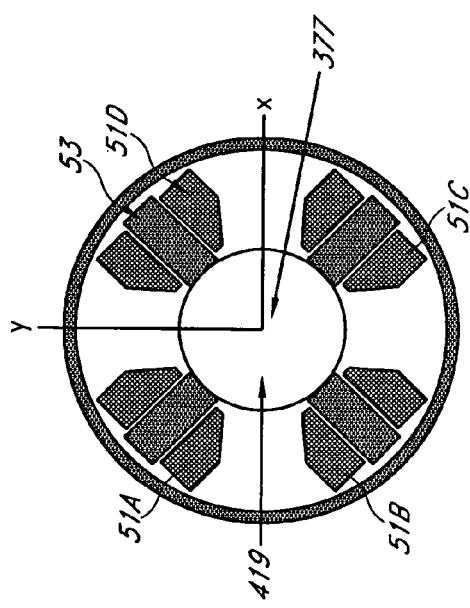
FIG. 3
| Magnet Assembly | Coil Current Direction 409 | | | |
|---|---|---|---|---|
| | 409.1CW | CW | CCW | CCW |
| 51B | CW | CCW | CCW | CW |
| 51C | 409.2CCW | CCW | CW | CW |
| 51D | CCW | CW | CW | CCW |
| B Field Direction 408 | +X → | -Y → | -X ← | +Y ← |
FIG. 4

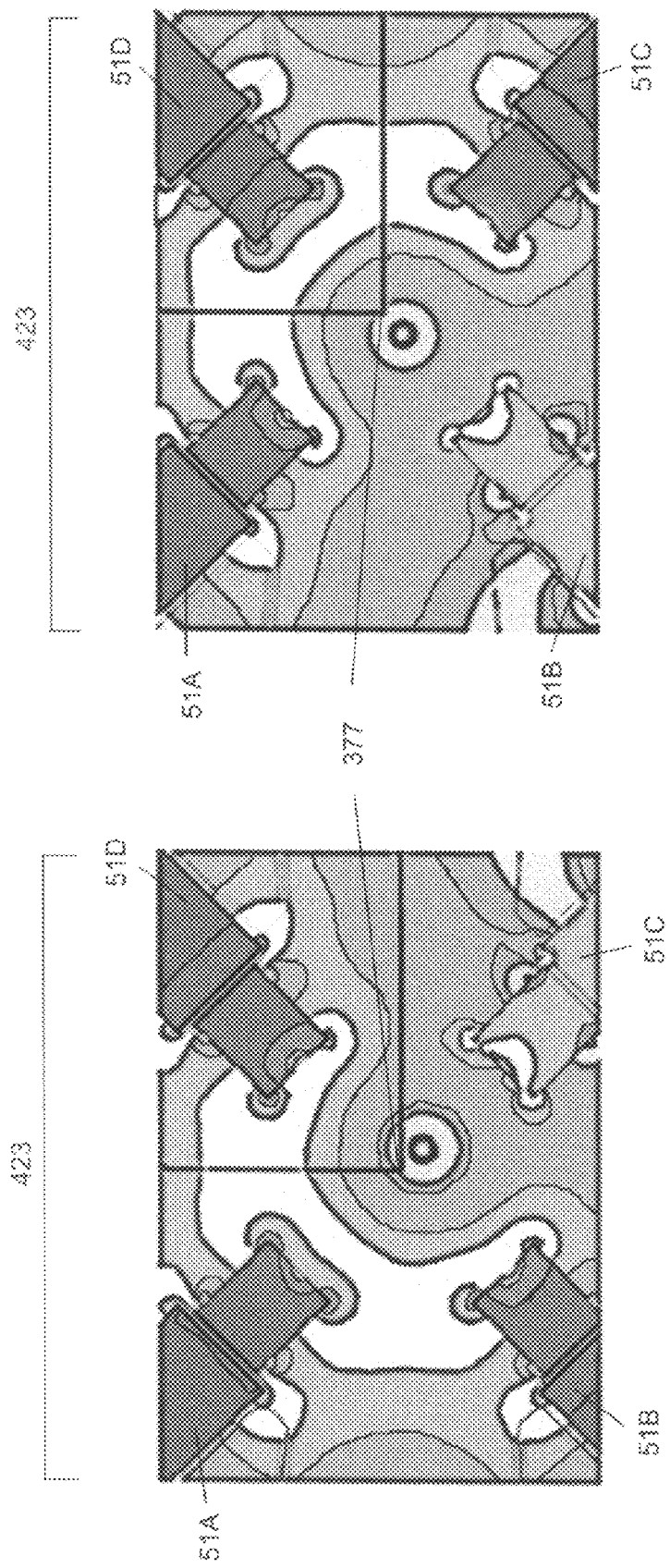

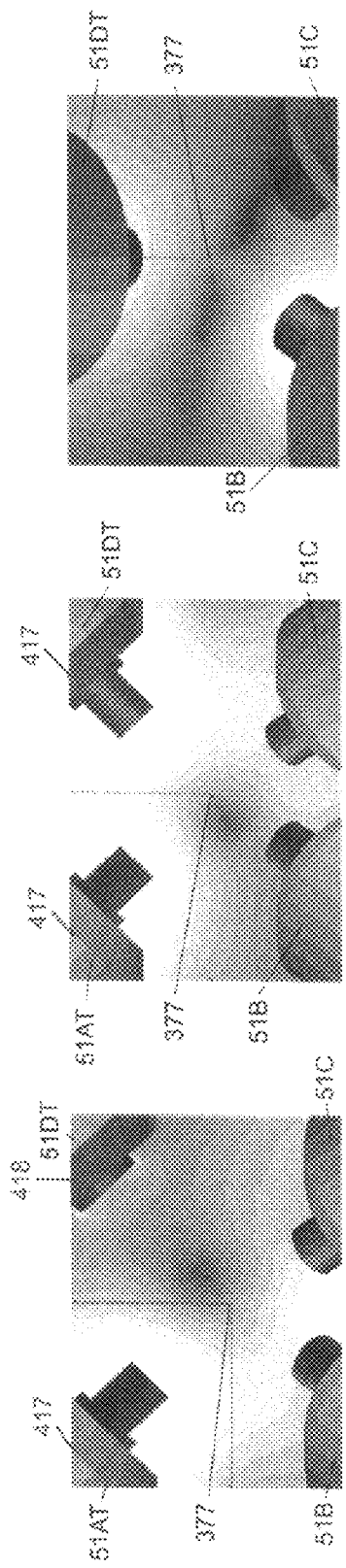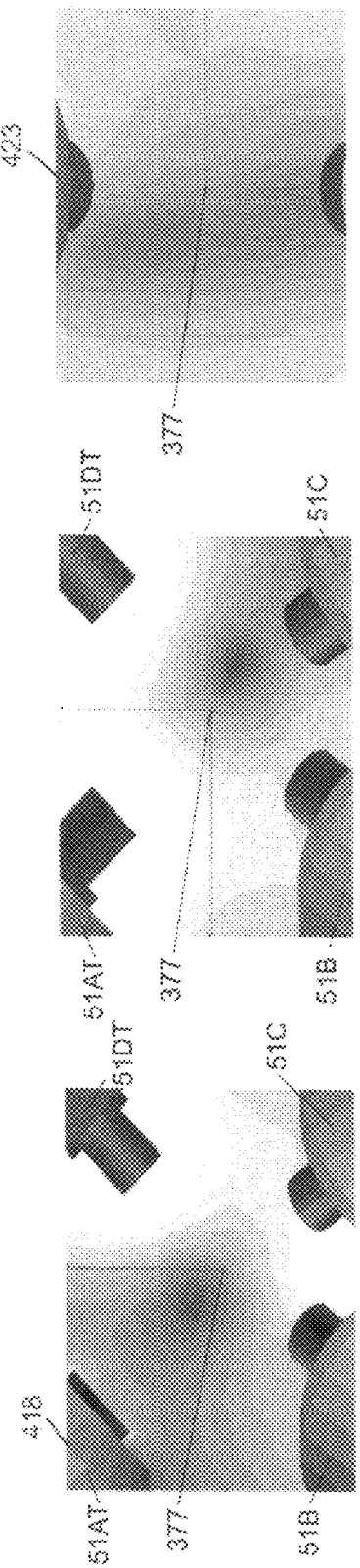

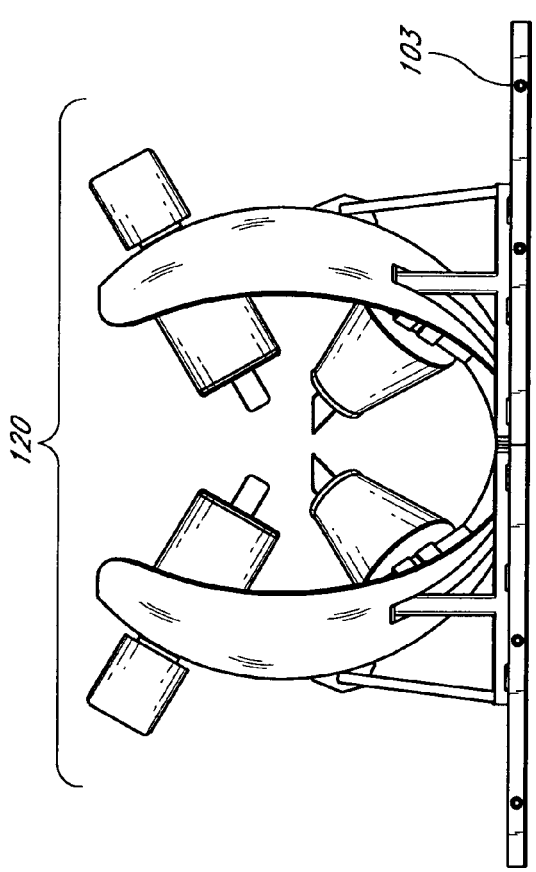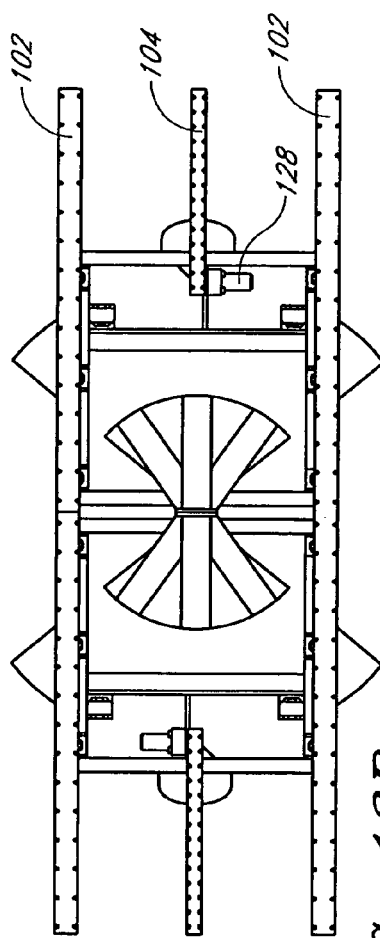
FIG. 13A
FIG. 13B

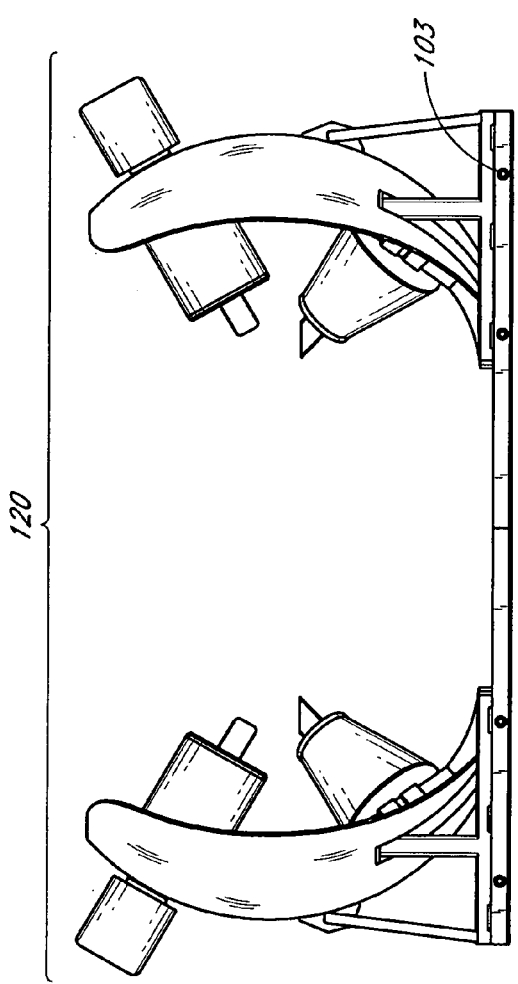
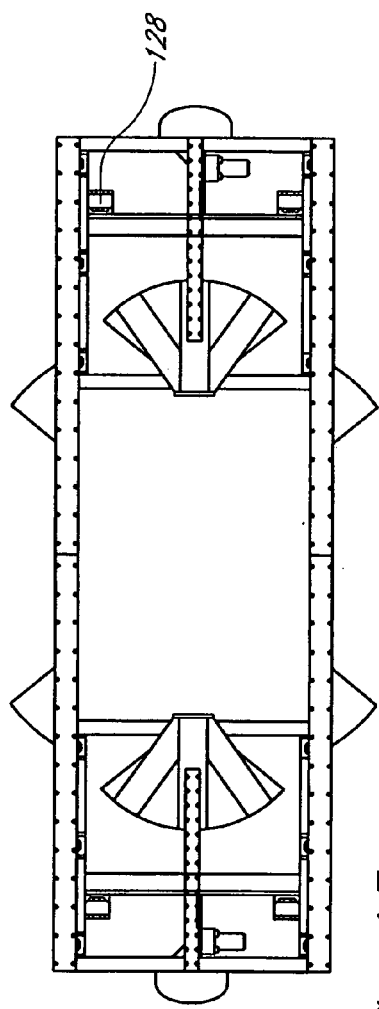
FIG. 14A
FIG. 15

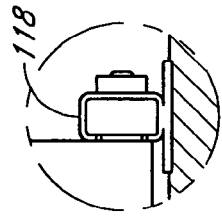
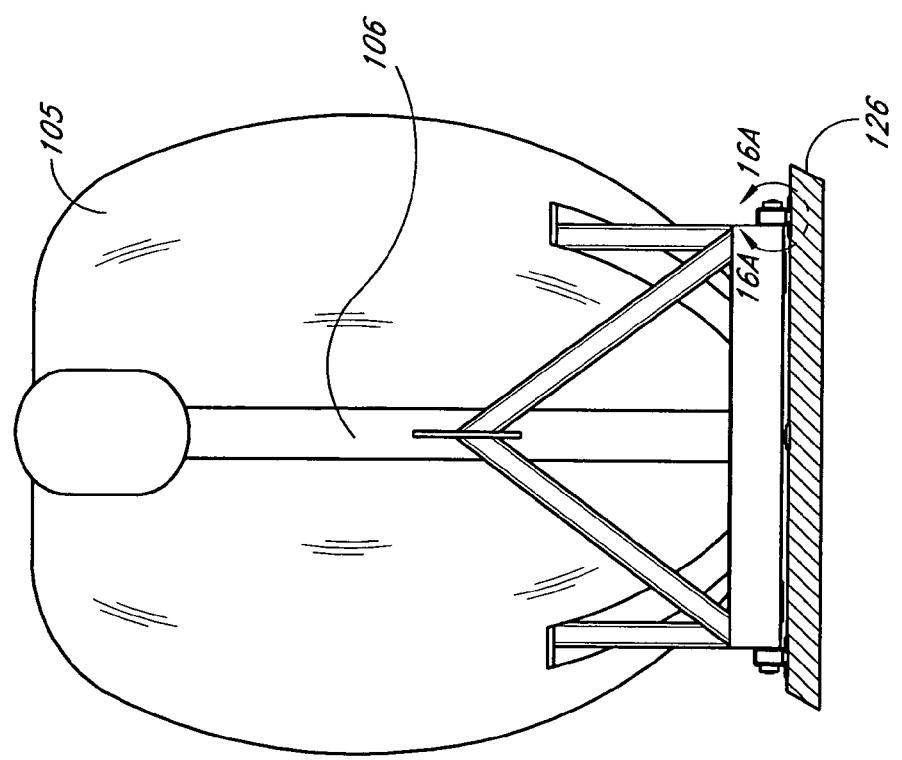

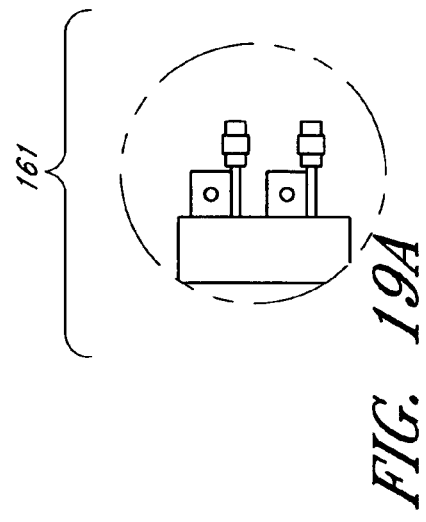
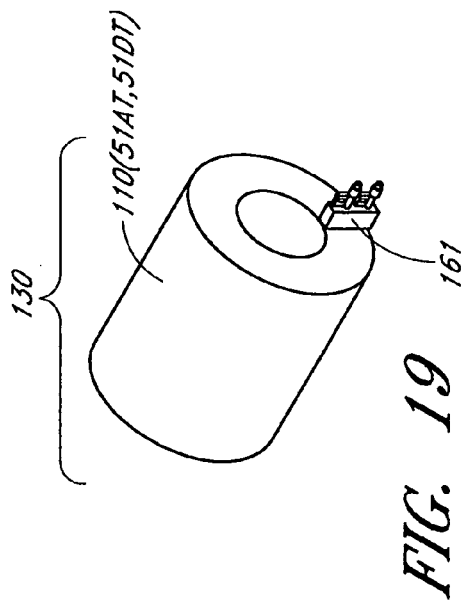
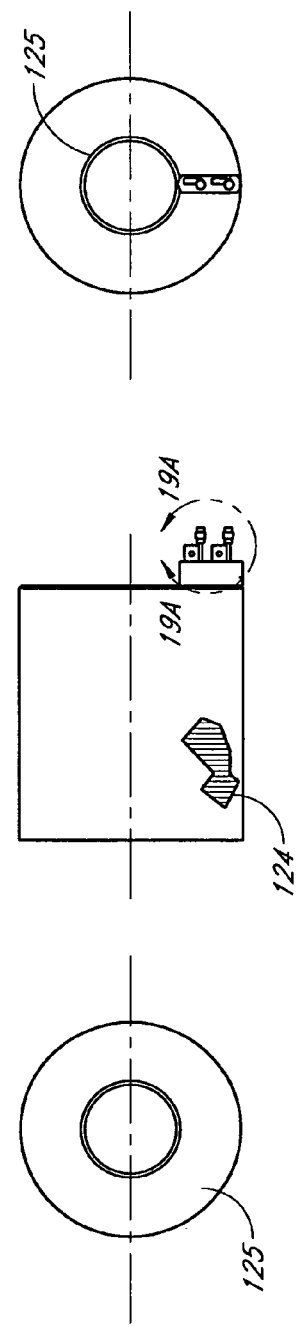
FIG. 19A
FIG. 19B
FIG. 19C
FIG. 19D
FIG. 19

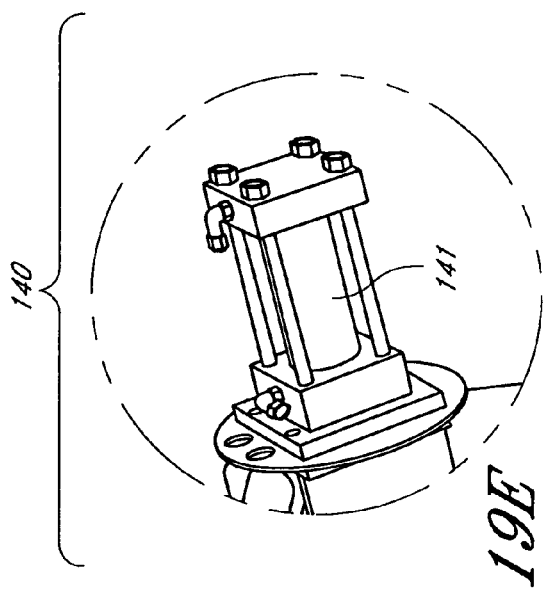
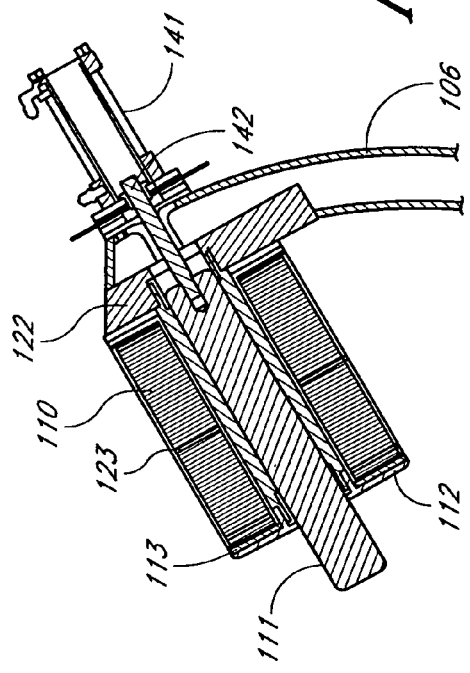
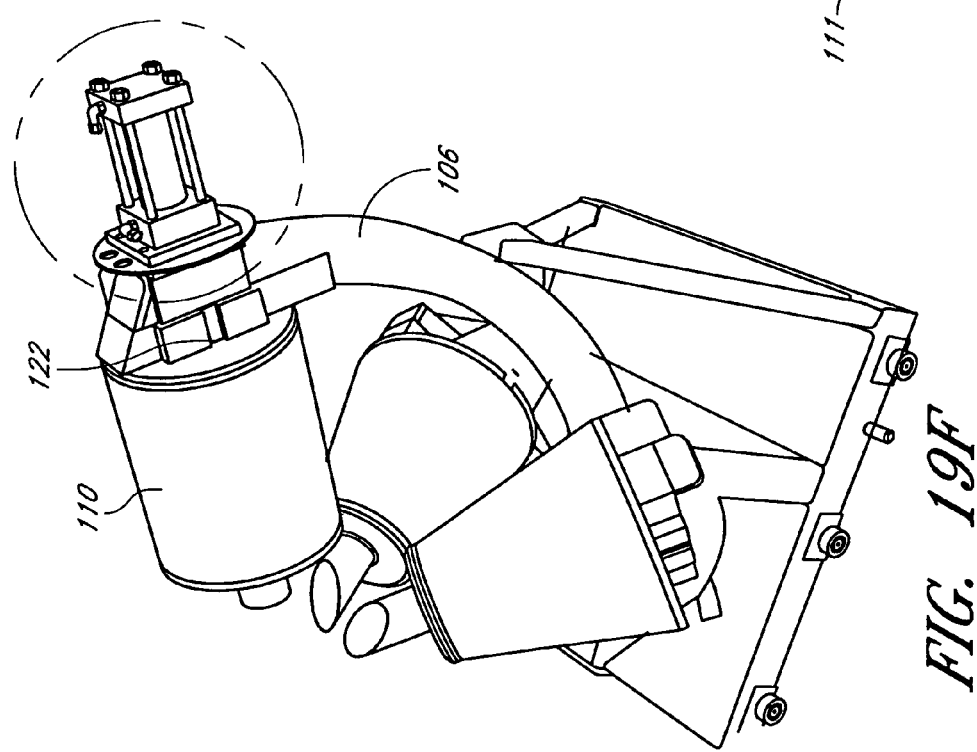
FIG. 19E
FIG. 19G
FIG. 19F

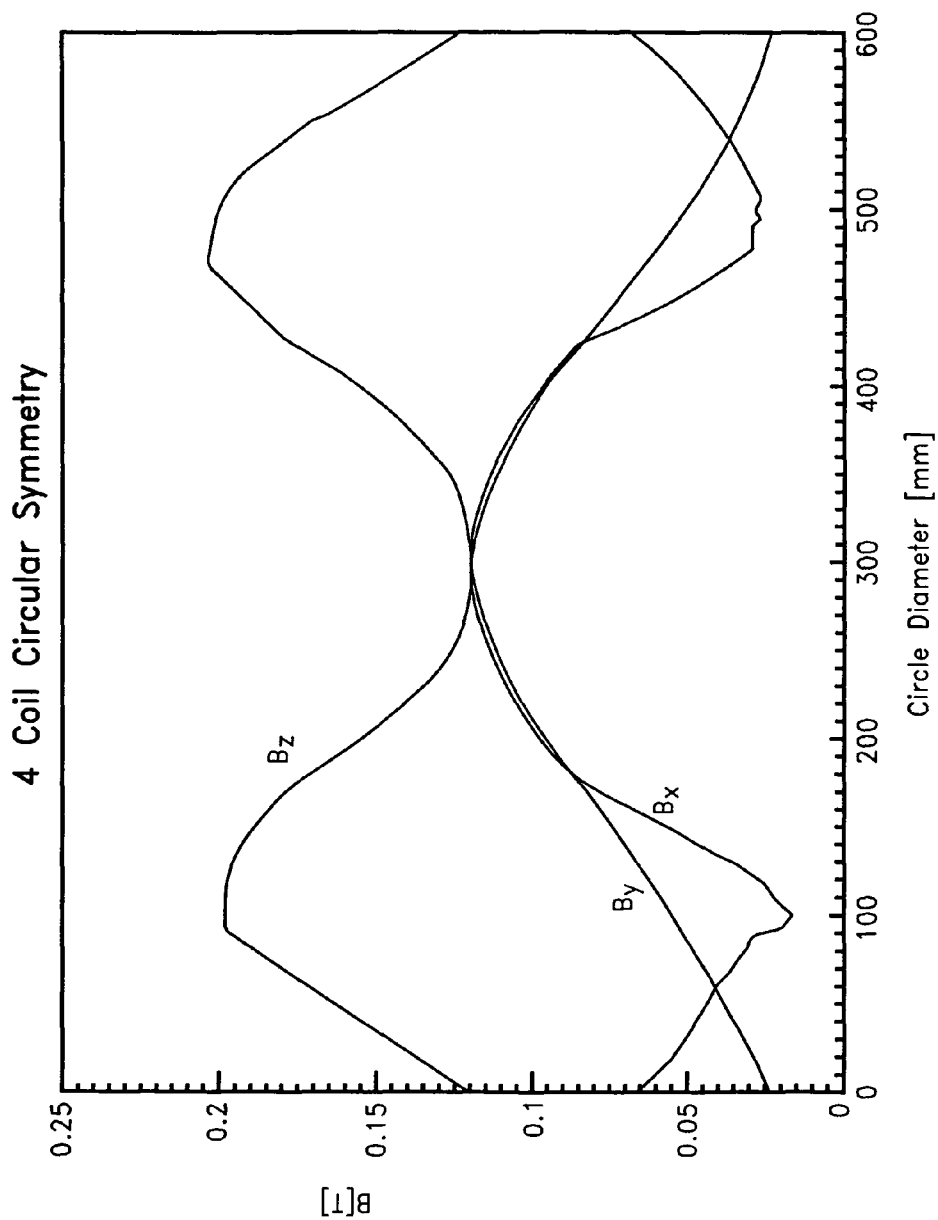

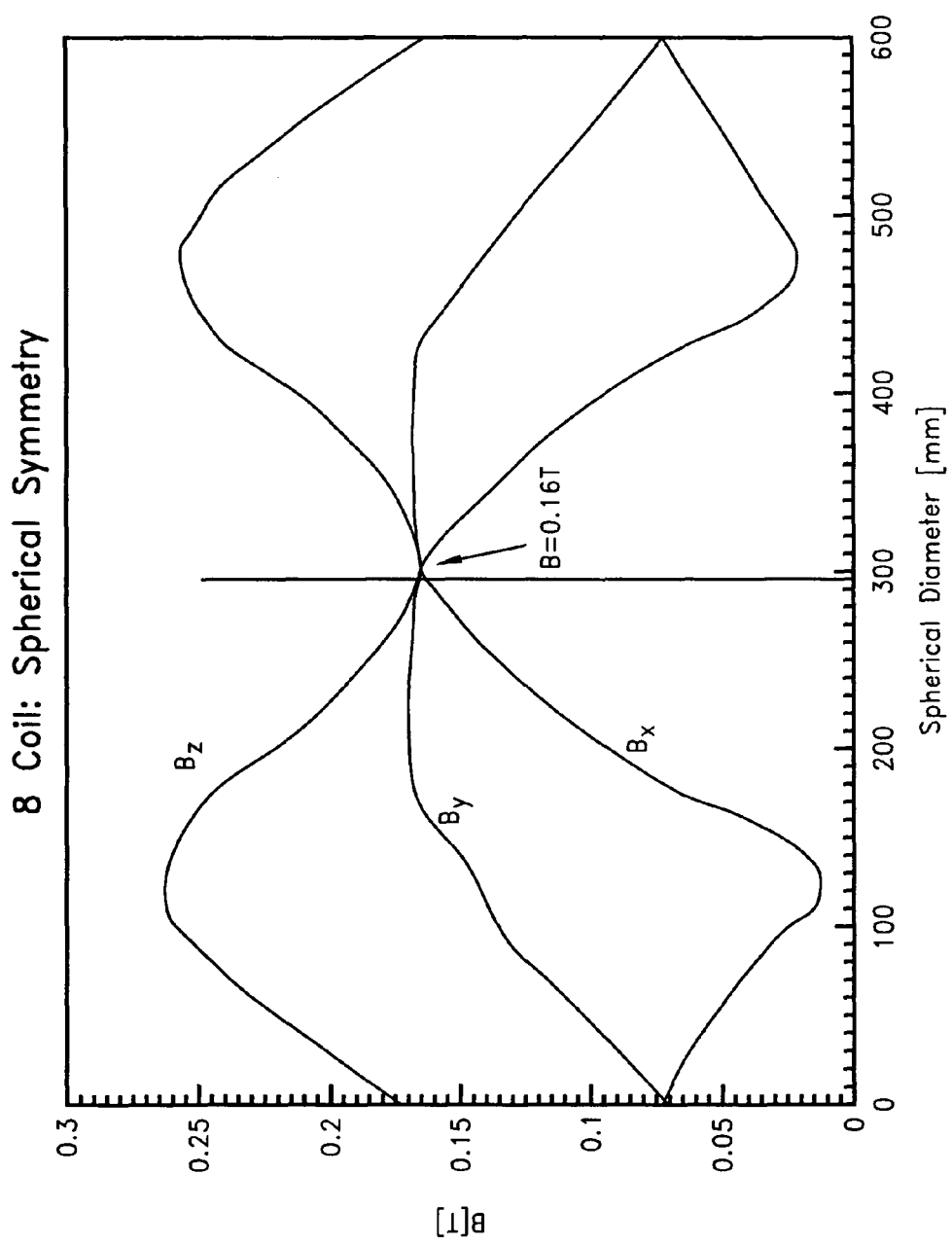

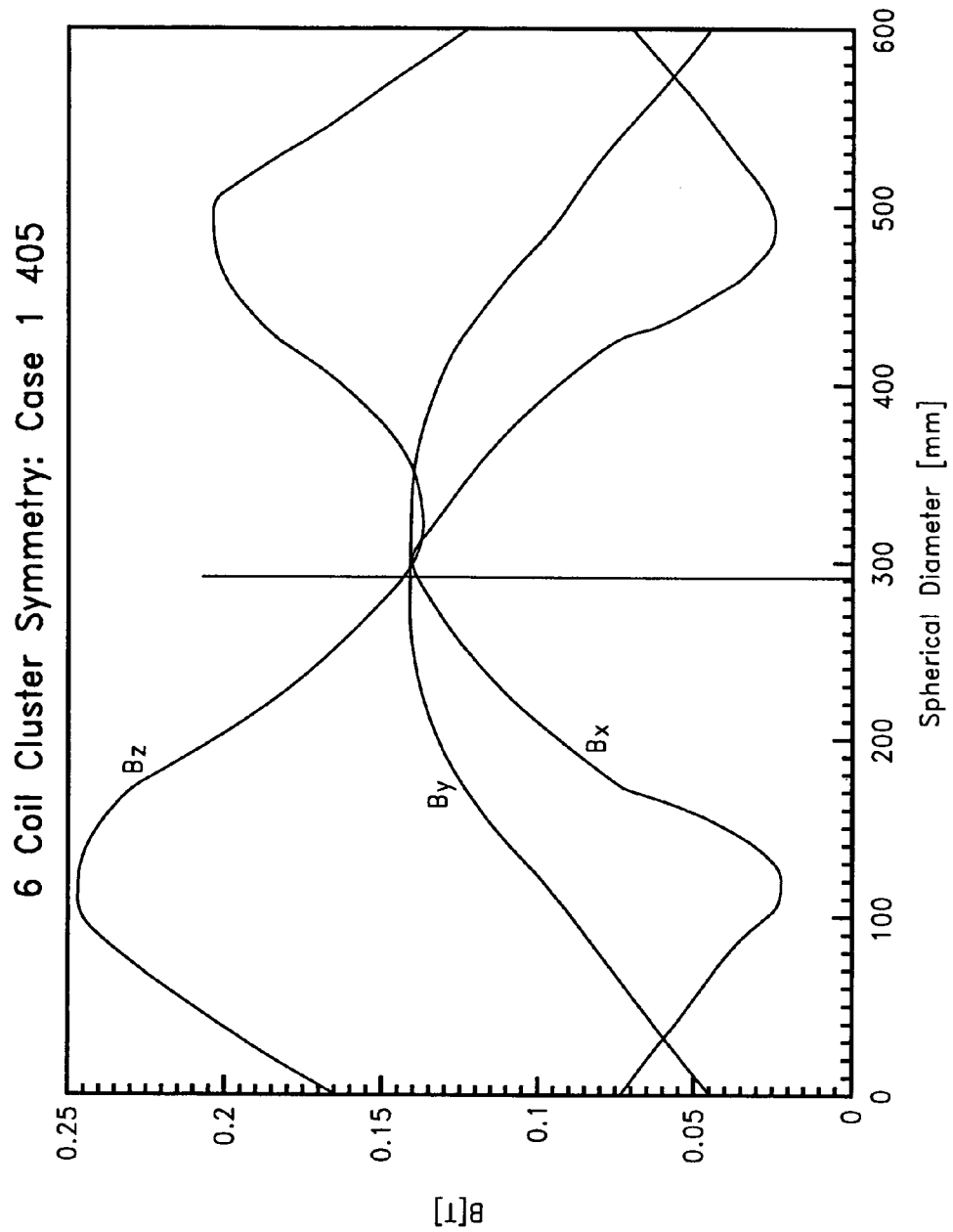

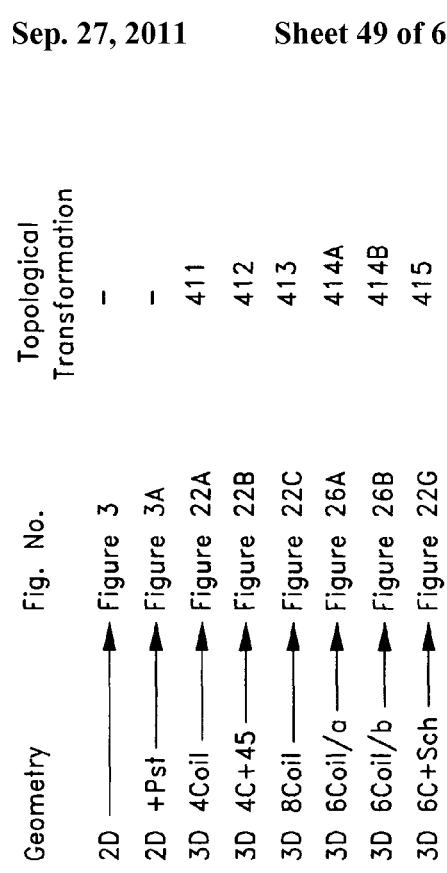
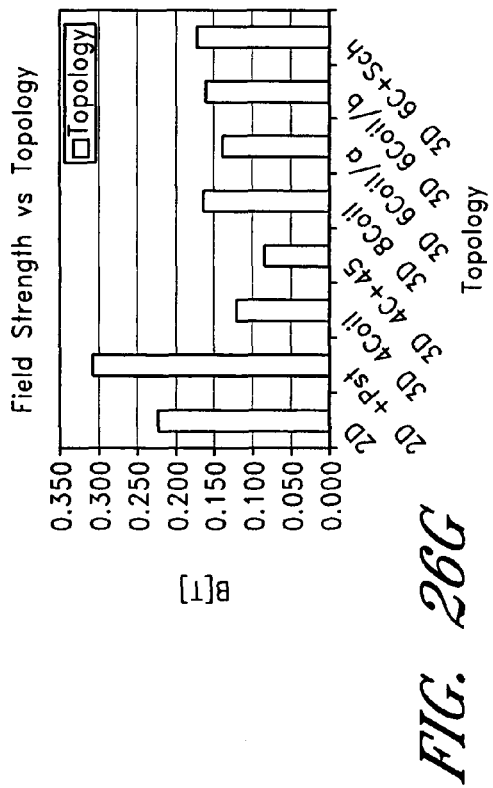
FIG. 26G
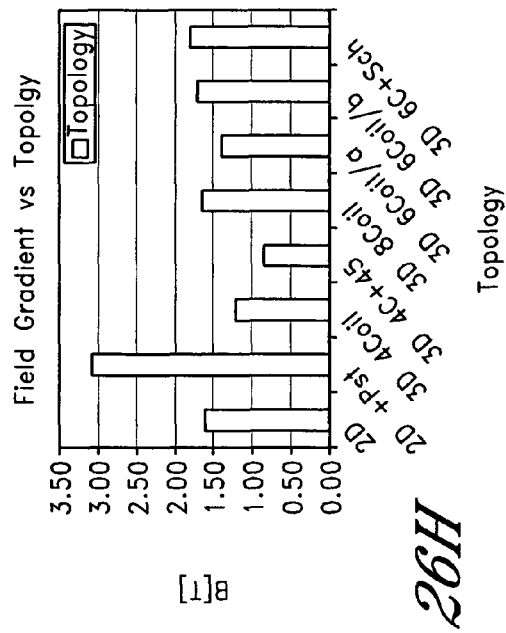
FIG. 26H
FIG. 26I

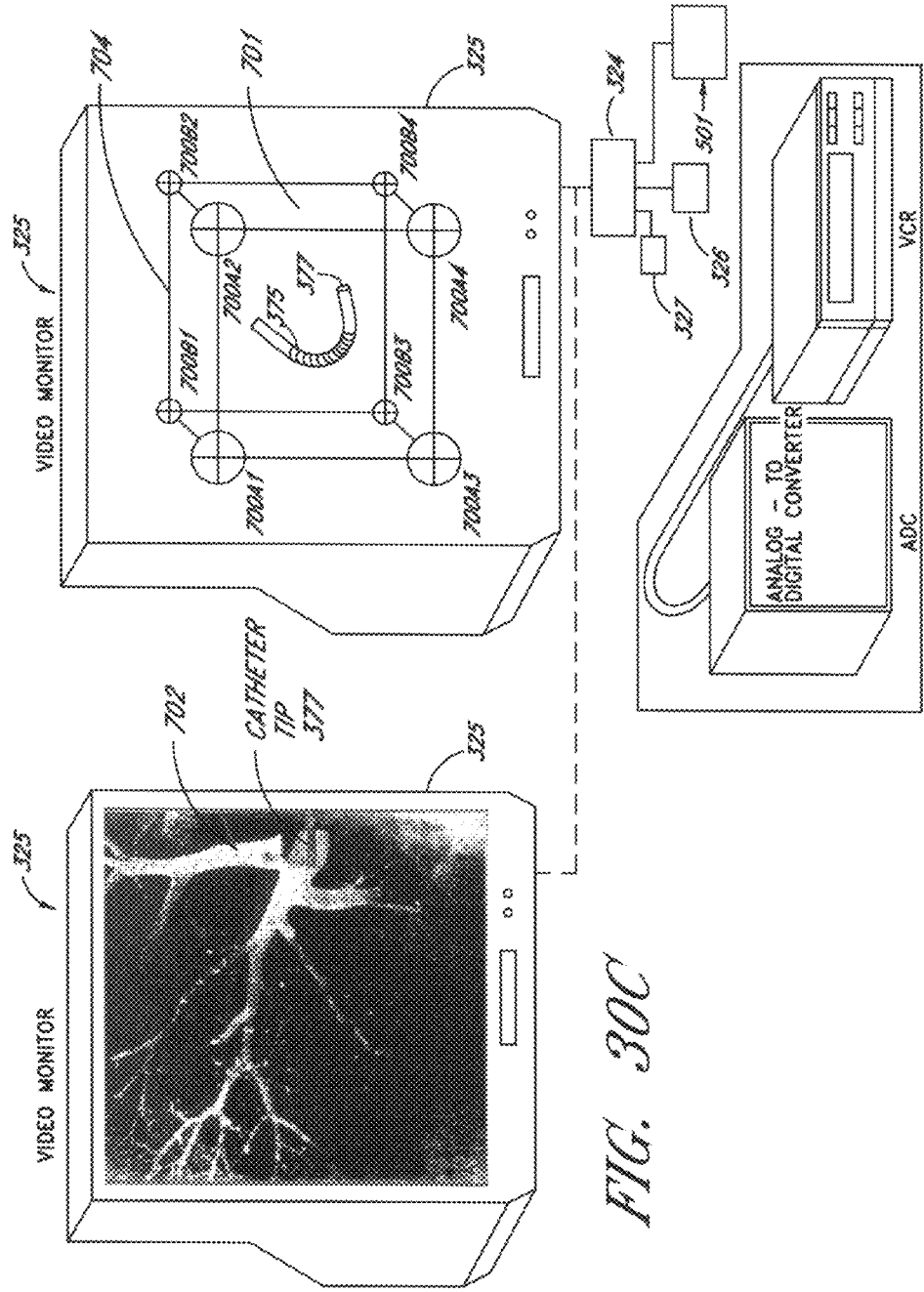

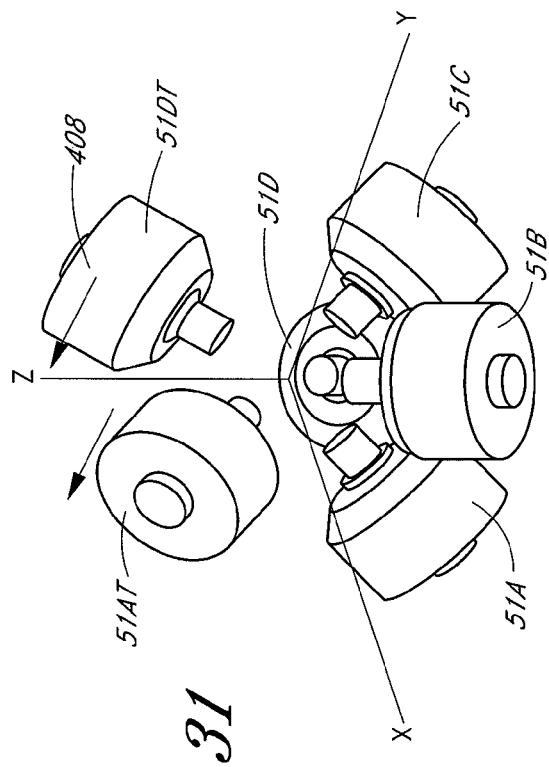
FIG. 31
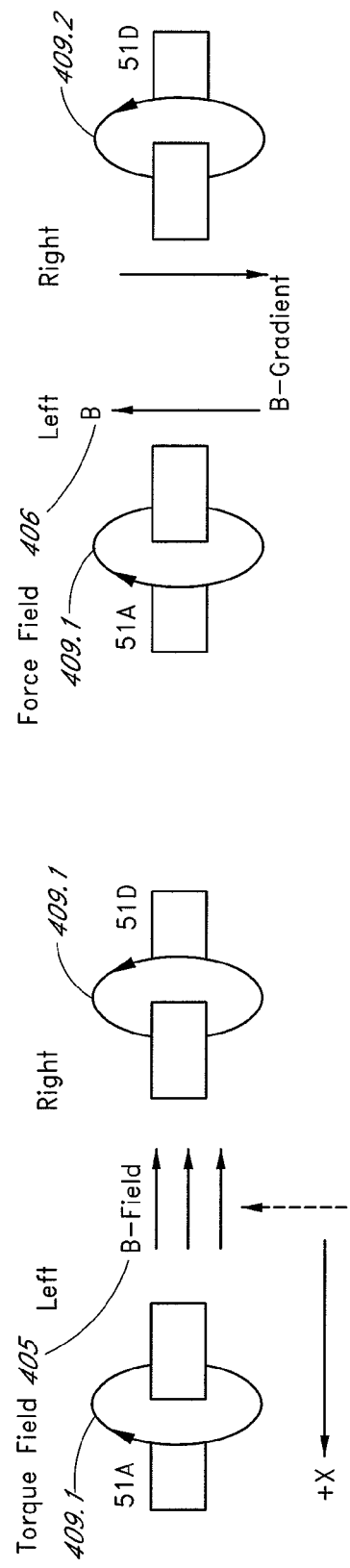
FIG. 31B
FIG. 31A

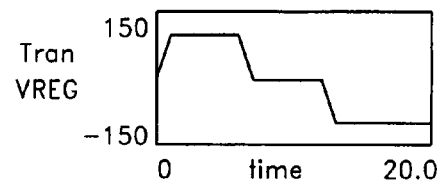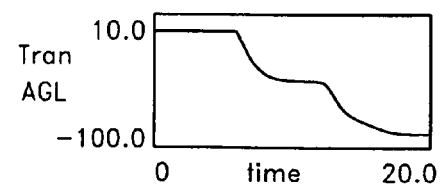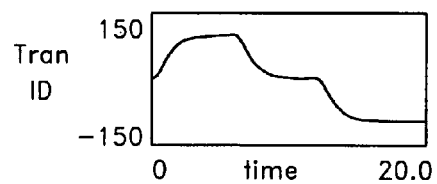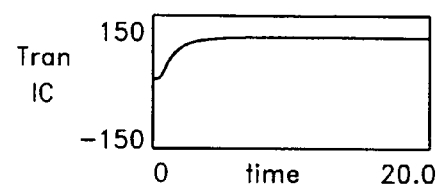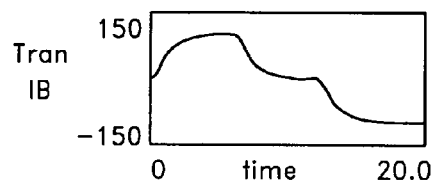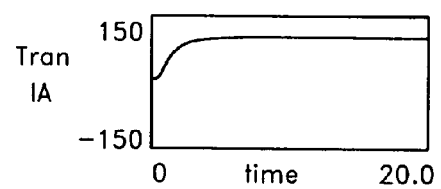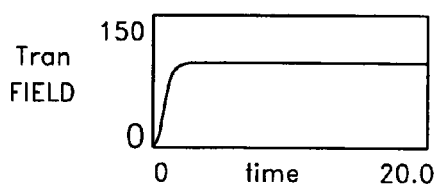
FIG. 32C

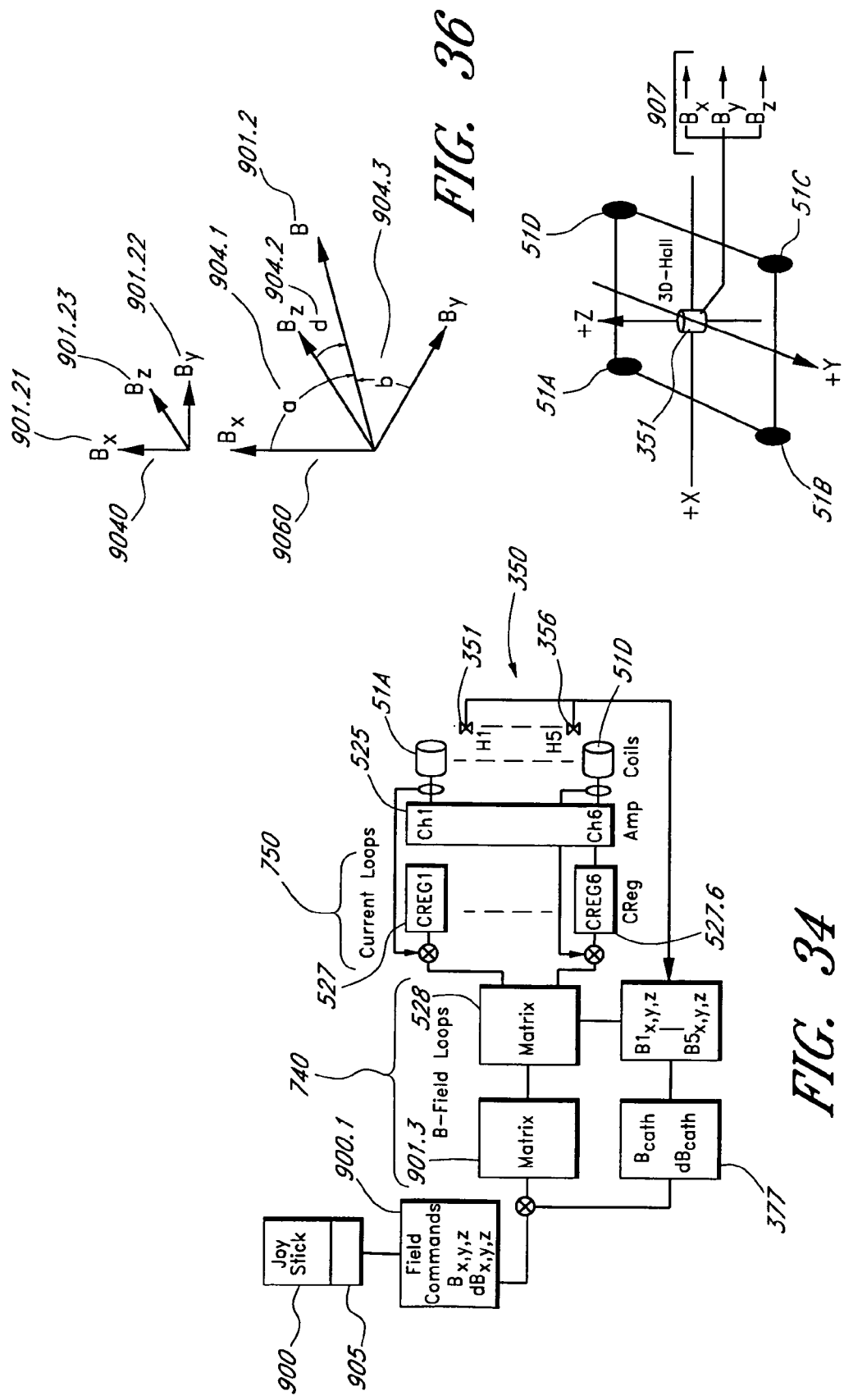

APPARATUS AND METHOD FOR SHAPED MAGNETIC FIELD CONTROL FOR CATHETER, GUIDANCE, CONTROL, AND IMAGING

REFERENCE TO RELATED APPLICATION

The entire contents of Applicant's co-pending U.S. application Ser. No. 10/690,472, titled "SYSTEM AND METHOD FOR RADAR-ASSISTED CATHETER GUIDANCE AND CONTROL", filed Oct. 20, 2003, are hereby incorporated by reference.

BACKGROUND

1. Field of the Invention

The present invention relates to magnetic guiding, steering, and advancing invasive medical devices such as catheters and catheter-type devices.

2. Description of the Related Art

Catheterization is typically performed by inserting an invasive device into an incision or a body orifice. These procedures rely on manually advancing the distal end of the invasive device by pushing, rotating, or otherwise manipulating the proximal end that remains outside of the body. Real-time X-ray imaging is a common method for determining the position of the distal end of the invasive device during the procedure. The manipulation continues until the distal end reaches the destination area where the diagnostic or therapeutic procedure is to be performed. This technique requires great skills on the part of the surgeon/operator. Such skill can only be achieved after a protracted training period and extended practice. A relatively high degree of manual dexterity is also required.

Recently, magnetic systems have been proposed, wherein magnetic fields produced by one or more electromagnets are used to guide and advance a magnetically-tipped catheter. The electromagnets in such systems produce large magnetic fields that are potentially dangerous to medical personnel and that can be disruptive to other equipment.

Therefore, there is a great and still unsatisfied need for an apparatus and method for guiding, steering, and advancing invasive devices and for accurately controlling their positions for providing positioning of magnetic fields and field gradient, for providing a fields configured to push/pull, bend/rotate, and by further enabling apparatus to align the distal end of the catheter tip so as to achieve controlled movement in 3D space and ability of apparatus to control the magnetic field characteristics without the customary power and field intensities seen in the prior art.

SUMMARY

These and other problems are solved by a magnetic catheter guidance system that uses moveable electromagnets to configure a magnetic field for guiding a catheter or other device through a body.

In one embodiment, a magnetic circuit is configured to generate a desired magnetic field in the region of a multi-coil cluster of electromagnets. In one embodiment, one or more poles of the cluster are moveable with respect to other poles in the cluster to allow shaping of the magnetic field. In one embodiment, one or more magnet poles can be extended or retracted to shape the magnetic field. In one embodiment, the electromagnets can be positioned to generate magnetic fields that exert a desired torque on the catheter, but without advancing force on the tip (e.g., distal end of the catheter). This affords bend and rotate movements of the catheter tip toward a selected direction. In one embodiment, the multi-coil cluster is configured to generate a relatively high gradient field region for exerting a moving force on the tip (e.g., a push-pull movement), with little or no torque on the tip.

In one embodiment, the catheter guidance system includes a closed-loop servo feedback system. In one embodiment, a radar system is used to determine the location of the distal end of the catheter inside the body, thus, minimizing or eliminating the use of ionizing radiation such as X-rays. The catheter guidance system can also be used in combination with an X-ray system (or other imaging systems) to provide additional imagery to the operator. The magnetic system used in the magnetic catheter guidance system can also be used to locate the catheter tip to provide location feedback to the operator and the control system. In one embodiment, a magnetic field source is used to create a magnetic field of sufficient strength and orientation to move a magnetically-responsive catheter tip in a desired direction by a desired amount.

In one embodiment, the multi-coil cluster is configured to generate a magnetic field gradient for exerting an orthogonal force on the tip (side-ways movement), with little or no rotating torque on the tip. This is useful for aligning the tip at narrow forks of artery passages and for scraping a particular side of artery or in treatment of mitral valve stenosis.

In one embodiment, the multi-coil cluster is configured to generate a mixed magnetic field to push/pull and/or bend/rotate the distal end of the catheter tip, so as to guide the tip while it is moving in a curved space and in cases where the stenosis is severe or artery is totally blocked.

In one embodiment, the multi-coil cluster is configured to move the location of the magnetic field in 3D space relative to the patient. This magnetic shape control function provides efficient field shaping to produce desired magnetic fields for catheter manipulations in the operating region (effective space).

One embodiment includes a catheter and a guidance and control apparatus that allows the surgeon/operator to position the catheter tip inside a patient's body. The catheter guidance and control apparatus can maintain the catheter tip in the correct position. One embodiment includes a catheter and a guidance and control apparatus that can steer the distal end of the catheter through arteries and forcefully advance it through plaque or other obstructions.

One embodiment includes a catheter guidance and control apparatus that displays the catheter tip location with significantly reduced X-ray exposure to the patient and staff.

One embodiment includes a catheter guidance and control apparatus that is more intuitive and simpler to use, that displays the catheter tip location in three dimensions, that applies force at the catheter tip to pull, push, turn, or hold the tip as desired, and that is configured to producing a vibratory or pulsating motion of the tip with adjustable frequency and amplitude to aid in advancing the tip through plaque or other obstructions. One embodiment provides tactile feedback at the operator control to indicate an obstruction encountered by the tip.

In one embodiment, the Catheter Guidance Control and Imaging (CGCI) system allows a surgeon to advance, accurately position a catheter, and to view the catheter's position in three dimensions by using a radar system to locate the distal end of the catheter. In one embodiment, the radar data can be combined with X-ray imagery to produce a composite display that includes radar and X-ray data. In one embodiment, the radar system includes a Synthetic Aperture Radar (SAR). In one embodiment, the radar system includes a wideband radar. In one embodiment, the radar system includes an impulse radar.

One embodiment includes a user input device called a "virtual tip." The virtual tip includes a physical assembly, similar to a joystick, which is manipulated by the surgeon/operator and delivers tactile feedback to the surgeon in the appropriate axis or axes if the actual tip encounters an obstacle. The Virtual tip includes a joystick type device that allows the surgeon to guide actual catheter tip through the patient's body. When actual catheter tip encounters an obstacle, the virtual tip provides tactile force feedback to the surgeon to indicate the presence of the obstacle.

In one embodiment, the physical catheter tip (the distal end of the catheter) includes a permanent magnet that responds to the magnetic field generated externally to the patient's body. The external magnetic field pulls, pushes, turns, and holds the tip in the desired position. One of ordinary skill in art will recognize that the permanent magnet can be replaced or augmented by an electromagnet.

In one embodiment, the physical catheter tip (the distal end of the catheter) includes a permanent magnet and two or more piezoelectric rings, or semiconductor polymer rings to allow the radar system to detect the second harmonics of the resonating signal emanating from the rings.

In one embodiment, the CGCI apparatus provides synchronization by using a radar and one or more fiduciary markers to provide a stereotactic frame of reference.

In one embodiment, the electromagnetic circuit of the CGCI apparatus includes a C-Arm geometry using a ferromagnetic substance (e.g., a furous, substance, nickel substance, etc.) so as to increase the efficiency of the magnetic circuit.

In one embodiment, the CGCI apparatus uses numerical transformations to compute currents to be provided to various electromagnets and position of one or more of the electromagnet to control the magnetic field used to push/pull and rotate the catheter tip in an efficient manner.

In one embodiment, the CGCI apparatus includes a UWB impulse radar for detecting the catheter tip and body organs, and synchronizing their motions.

In one embodiment, the CGCI apparatus includes a motorized and/or hydraulic mechanism to allow the electromagnet poles to be moved to a position and orientation that reduces the power requirements desired to push, pull, and rotate the catheter tip.

In one embodiment, the CGCI apparatus is used to perform an implantation of a pacemaker during an electrophysiological (EP) procedure.

In one embodiment, the CGCI apparatus uses radar or other sensors to measure, report and identify the location of a moving organ within the body (e.g., the heart, lungs, etc.) with respect to the catheter tip and one or more fiduciary markers, so as to provide guidance, control, and imaging to compensate for movement of the organ, thereby simplifying the surgeon's task of manipulating the catheter through the body.

In one embodiment, the operator control provides the position and orientation command inputs to a servo system that controls the catheter tip position by generating and shaping the magnetic fields. A measurement of actual tip position and orientation is made via a sensory apparatus that includes a radar system. This measurement is used to provide feedback to the servo system and the operator interface.

In one embodiment, the servo system has a correction input that compensates for the dynamic position of a body part, or organ, such as the heart, thereby offsetting the response such that the actual tip moves substantially in unison with the dynamic position (e.g., with the beating heart).

In one embodiment of the catheter guidance system: i) the operator adjusts the physical position of the virtual tip, ii) a change in the virtual tip position is encoded and provided along with data from a radar system, iii) the control system generates servo system commands that are sent to a servo system control apparatus, iv) the servo system control apparatus operates the servo mechanisms to adjust the position of one or more electromagnet clusters by varying the distance and/or angle of the electromagnet clusters and energizing the electromagnets to control the magnetic catheter tip within the patient's body, v) the new position of actual catheter tip is then sensed by the radar, thereby allowing synchronization and superimposing of the catheter position on an image produced by fluoroscopy and/or other imaging modality vi) providing feedback to the servo system control apparatus and to the operator interface and vii) updating the displayed image of the catheter tip position in relation to the patient's internal body structures.

In one embodiment, the operator can make further adjustments to the virtual catheter tip position and the sequence of steps ii through vii are repeated. In one embodiment, the feedback from the servo system control apparatus creates command logic when the actual catheter tip encounters an obstacle or resistance in its path. The command logic is used to control stepper motors which are physically coupled to the virtual catheter tip. The stepper motors are engaged as to create resistance in appropriate directions that can be felt by the operator, and tactile feedback is thus provided to the user.

In one embodiment, the apparatus uses scaling factors to calculate the magnetic field generated along the effective magnetic space.

In one embodiment, the apparatus is configured to generate a maximum force of 35 grams for push/pull of the catheter tip and a 35 gram force while the coil cluster is generating dB/dS field gradients between 1.6 T/m to 3.0 T/m.

In one embodiment, the apparatus generates a maximum torque of 0.013 Newton-meter on the catheter tip, while the coil cluster is generating a magnetic field strength between B=0.04 T and 0.15 T.

In one embodiment, the coil current polarity and polarity rotation are configured to allow the coil cluster to generate torque on the catheter tip.

In one embodiment, the coil current polarity and rotation are configured to provide an axial and/or orthogonal force on the catheter.

In one embodiment, a topological transformation allows control of the magnetic field in the 2D four coil geometry to form the magnetic field desired for navigating and controlling the catheter tip.

In one embodiment, a second topological transformation allows the apparatus to operate in 3D space while creating the magnetic field desired to push/pull and rotate the catheter tip.

In one embodiment, a symmetrical transformation is provided allowing the apparatus to operate with eight coil clusters.

In one embodiment, the eight coil symmetry is reduced to a six coil symmetry allowing the CGCI apparatus to generate the desired magnetic field in an optimized pattern.

In one embodiment, the coil cluster is fitted with a parabolic shield which collects the magnetic flux from the effective space and creates a return path to decrease the need to shield the stray magnetic radiation.

In one embodiment, the magnetic circuit efficacy of the CGCI apparatus is evaluated as to its topological properties and it is measured relative to torque control field variations in the magnetic center.

In one embodiment, the magnetic circuit efficacy of the CGCI apparatus is evaluated as to its topological properties and it is measured relative to force control gradient variations in the ±100 mm region around the magnetic center.

In one embodiment, the rotational transformation and its relationship to field strength and field gradient are mathematically established.

In one embodiment, a mathematical model for topological transformations of the geometry versus magnetic field generation is established.

In one embodiment, the CGCI apparatus is fitted with at least one hydraulically-actuating extension core, for varying the magnetic pole configuration to allow shaping of the magnetic field.

In one embodiment, the shaped magnetic field is configured as a variable magnetic pole geometry to control the catheter tip. The shaped field provides for operator control of the catheter tip while reducing power and reducing field strength by tailoring the field geometry.

In one embodiment, the CGCI apparatus is fitted with a parabolic shield for flux return to reduce the emission of the radiating field outside of the effective area to less than 20 gauss.

In one embodiment, the control scheme of the CGCI apparatus includes a boundary condition controller. The controller computes the fields surrounding the catheter based on the fields on the 2D planes enclosing the magnetic chamber. Equations for computing the fields with rotated coils on the surface of the sphere are established in the magnetic chamber.

In one embodiment, the coil is controlled from a bi-polar DC power source. A six channel regulator assisted by a computer using matrix algorithms controls the six coil magnetic configuration.

In one embodiment, user control is provided by an aircraft-type joystick, wherein movement of the joystick between the torque mode and the force mode is provided by a mode switch.

In one embodiment, the mode switch allows the controller to switch from torque control to force control as well as mixed torque and force control.

In one embodiment, the coil current polarities and magnitudes are defined and cross-referenced to the desired field directions for torque and force fields.

In one embodiment, the coil polarity combinations are expressed as a set of matrices, wherein the grouping of coils is used such that four coil and three coil groups associated with the virtual tip 2D planes are established.

In one embodiment, the symmetry group is a four coil group with 16 polarity combinations. Control simulated under the four coil XY plane, and under the topological transformation allows the state of the CGCI machine torque and force to be controlled.

In one embodiment, the coils are configured using symmetry where the group is rotated 90° from the symmetry group.

In one embodiment, the rotational steps are smoothly transferred while the coil currents is oscillating from −100% to +100% through zero, and where the control slope between 0%-to-100% coil current is subject to a nonlinear inverse cosine function.

In one embodiment, the entire CGCI magnetic circuit is modeled using a low-level logic simulation of the action performed by the joystick prior to activating the power amplifiers that provide current to the coils.

In one embodiment, the magnitude control function of the CGCI controller directing the deployment as well as retraction of the piston actuated extension core is used to shape the magnetic field affording a variable magnetic field for moving the catheter tip in the desired direction.

In one embodiment, a Hall effect ring measures the boundary plane field strength as a measure of the joystick movement. This allows the CGCI to operate on the boundary planes of the field, rather than the interior of the magnetic chamber, while allowing the Hall effect sensor to operate in a range of a few hundred gauss fields.

BRIEF DESCRIPTION OF THE FIGURES

FIG. 1 is a perspective view of the magnet structure of the Catheter Guidance Control and Imaging (CGCI) system.

FIG. 3 shows a magnet assembly with retracted cores.

FIG. 3A shows the magnet assembly of FIG. 3 with an extended core.

FIG. 4 shows field directions corresponding to currents in the magnet assembly of FIG. 3.

FIG. 12 is a field map showing fields corresponding to a first coil and current configuration using a transformed magnet cluster.

FIG. 12A is a field map showing fields corresponding to a second coil and current configuration using a transformed magnet cluster.

FIG. 12B is a field map showing fields corresponding to a third coil and current configuration using a transformed magnet cluster.

FIG. 12C is a field map showing fields corresponding to a fourth coil and current configuration using a transformed magnet cluster.

FIG. 12D is a field map showing fields corresponding to a fifth coil and current configuration using a transformed magnet cluster.

FIG. 12E is a field map showing fields corresponding to a sixth coil and current configuration using a transformed magnet cluster.

FIG. 12F is a field map showing fields corresponding to a seventh coil and current configuration using a transformed magnet cluster.

FIG. 12G is a field map showing fields corresponding to a eighth coil and current configuration using a transformed magnet cluster.

FIG. 13A is a side view of the apparatus of FIG. 1.

FIG. 13B is an underside view of the apparatus of FIG. 1.

FIG. 14A is a side view of the configuration shown in FIG. 14.

FIG. 15 is an underside view of the configuration shown in FIG. 14.

FIG. 16 is an end view of the configuration shown in FIG. 14.

FIG. 19 is an isometric view of a coil assembly.

FIG. 19A shows water connections of the coil assembly.

FIG. 19B is a front view of the cylindrical coil assembly.

FIG. 19C is a side view of the cylindrical coil assembly.

FIG. 19D is a rear view of the cylindrical coil assembly.

FIG. 19E shows the hydraulic actuator for extending the magnetic core.

FIG. 19F shows the hydraulic actuator of FIG. 19E mounted to the coil cluster.

FIG. 19G is an interior view of the coil and extendable core with the hydraulic actuator.

FIG. 23A shows B fields of the 4 coil circular symmetry.

FIG. 25A shows B fields of the 8 coil spherical symmetry.

FIG. 26A shows B fields of the 6 coil cluster.

FIG. 26G shows field strength versus topology.

FIG. 26H shows field gradient versus topology.

FIG. 26I relates geometry to figure number.

FIG. 30C shows a display of a catheter inside a patient.

FIG. 30D shows position capture using radar and employing fiduciary markers.

FIG. 31 shows the six cluster system and a coordinate system for use in connection with FIGS. 31A and 31B.

FIG. 31A shows operational for the torque field.

FIG. 31B shows operation for the force field.

FIG. 32C shows plots of timer versus circuit voltages and fields.

FIG. 34 is a block diagram of the Hall effect/magnetic sensors used in the control of the magnetic chamber.

FIG. 35 is a schematic showing the Hall effect sensor array as used in measuring the boundary condition of the magnetic chamber.

FIG. 36 is a vector representation of an electro magnetic field located in a three dimensional coordinate system.

DETAILED DESCRIPTION

Figure 1B:
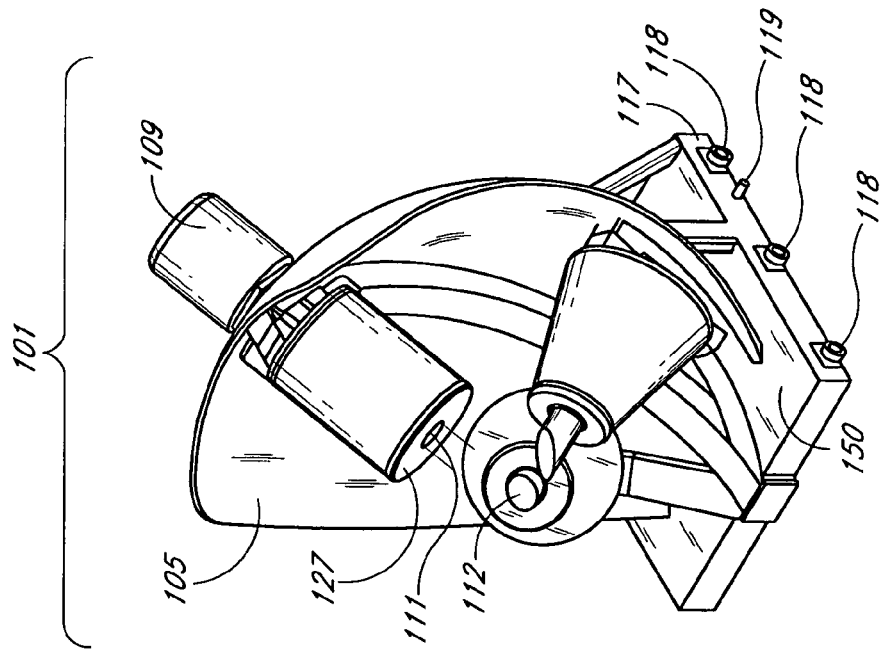
FIG. 1B is a perspective view of the CGCI right section showing the hydraulically-actuated core extracted.
Figure 1A:
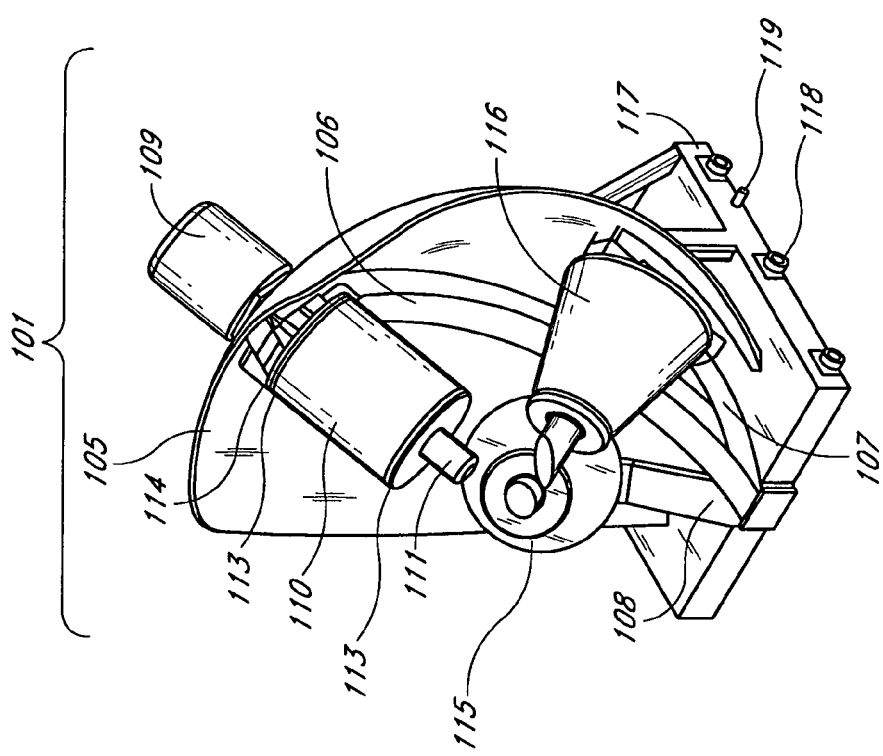
FIG. 1A is a perspective view of the CGCI right section showing the hydraulically-actuated core extended.

FIGS. 1, 1A and 1B are isometric drawings of a Catheter Guidance Control and Imaging (CGCI) system 1500, having a left coil cluster 100 and a right coil cluster 101 provided to rails 102. The rails 102 act as guide alignment devices. The CGCI system workstation 1500 includes a structural support assembly 120, a hydraulic system 140, a propulsion system 150, a cooling system 160, and a coil-driver system 170.

A central arc 106 supports an upper cylindrical coil 110 and two shorter arcs 107, 108 support two conical shaped coils 115, 116. The two shorter arcs 107, 108 are displaced from the central arc 106 by approximately 35 degrees. The angle of separation between the two smaller arcs is approximately 70 degrees.

At the end of each arc 106, 107 and 108 is a machined block of 1010 steel with a connection that provides for attachment of the coil assemblies 115, 116, 110.

Two curved shield plates 105 form a shield to at least partially contain and shape the magnetic fields. The shields 105 also provide lateral strength to the assembly. A base 117 houses the propulsion system 150 and locking mechanism 118. In one embodiment, the plates 105 are made from steel, nickel, or other magnetic material.

FIGS. 1A and 1B further show various mechanical details which form the CGCI cluster half section (right electromagnetic cluster 101). A locking hole 103, a spur-drive rail 104, cam rollers 118, and the solenoid locking pin 119, are configured to allow portions of the CGCI to move along the tracks 102. The cluster 101 includes three electromagnets forming a magnetic circuit. The left coil 116 and right coil 115 are mounted as shown and are supported by C-Arms 107 and 108. The coil 110 includes a hydraulically-actuated core 111, supported by a coil clamping disc 127 made out of stainless steel. A coil stress relief disc 113 made out of Teflon. The coil cylinder 110, is enclosed by a coil base disc 114 made out of stainless steel. The coil core 111 is actuated (extended and retracted) by a hydraulic system 109.

FIG. 1B shows the right coil cluster 101 with the hydraulically-actuated core 111 retracted by the use of the hydraulic system 109 which allows the CGCI to shape the magnetic field.

Figure 1C:
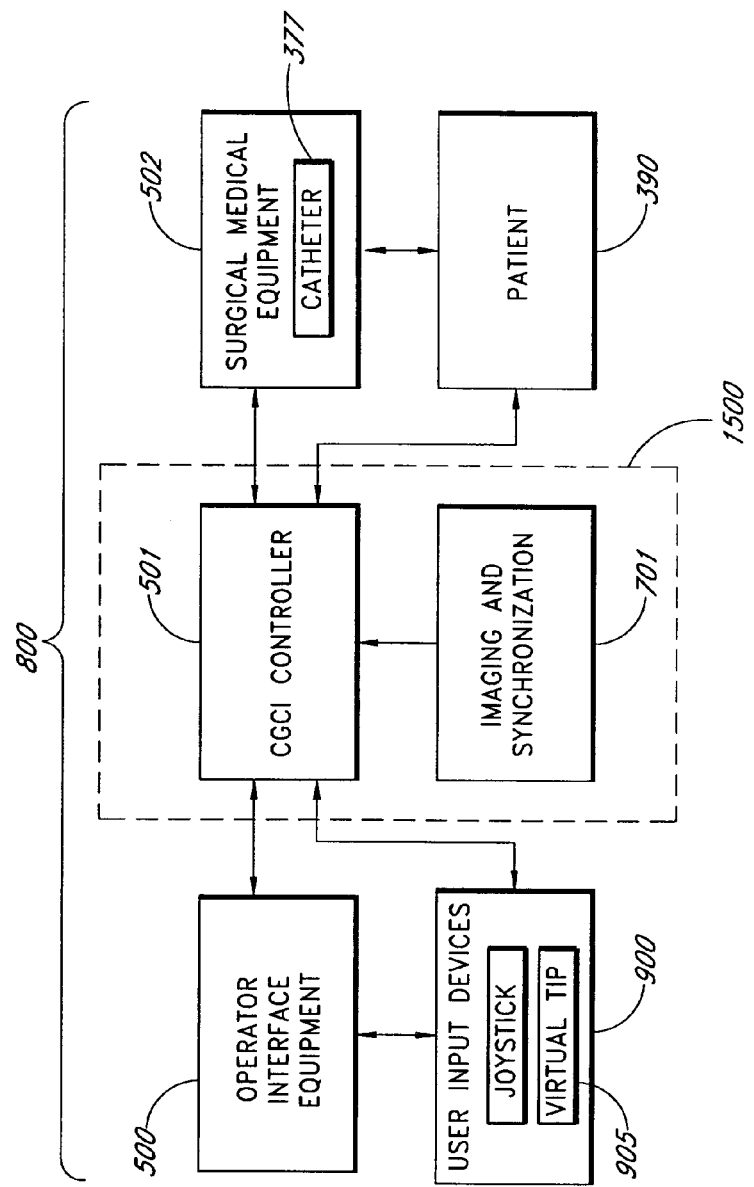
FIG. 1C is a system block diagram for a surgery system that includes an operator interface, a catheter guidance system, and surgical equipment.

FIG. 1C is a system block diagram for a surgery system 800 that includes an operator interface 500, the CGCI system 1500, surgical equipment 502 (e.g., a catheter tip 377, etc.), one or more user input devices 900, and a patient 390. The user input devices 900 can include one or more of a joystick, a mouse, a keyboard, a virtual tip 905, and other devices to allow the surgeon to provide command inputs to control the motion and orientation of the catheter tip 377.

In one embodiment, the CGCI system 1500 includes a controller 501 and an imaging synchronization module 701. The FIG. 1C shows the overall relationship between the various functional units and the operator interface 500, auxiliary equipment 502, and the patient 390. In one embodiment, the CGCI system controller 501 calculates the Actual Tip (AT) position of the distal end of a catheter as further described in the text in connection with FIGS. 30C and 30D. Using data from the Virtual Tip (VT) 905 and the imaging and synchronization module 701, the CGCI system controller 501 determines the position error, which is the difference between actual tip position (AP) and the desired tip position (DP). In one embodiment, the controller 501 controls electromagnets to move the catheter tip in a direction selected to minimize the position error (PE). In one embodiment, the CGCI system controller 501, provides tactile feedback to the operator by providing force-feedback to the VT 905.

Figure 1D:
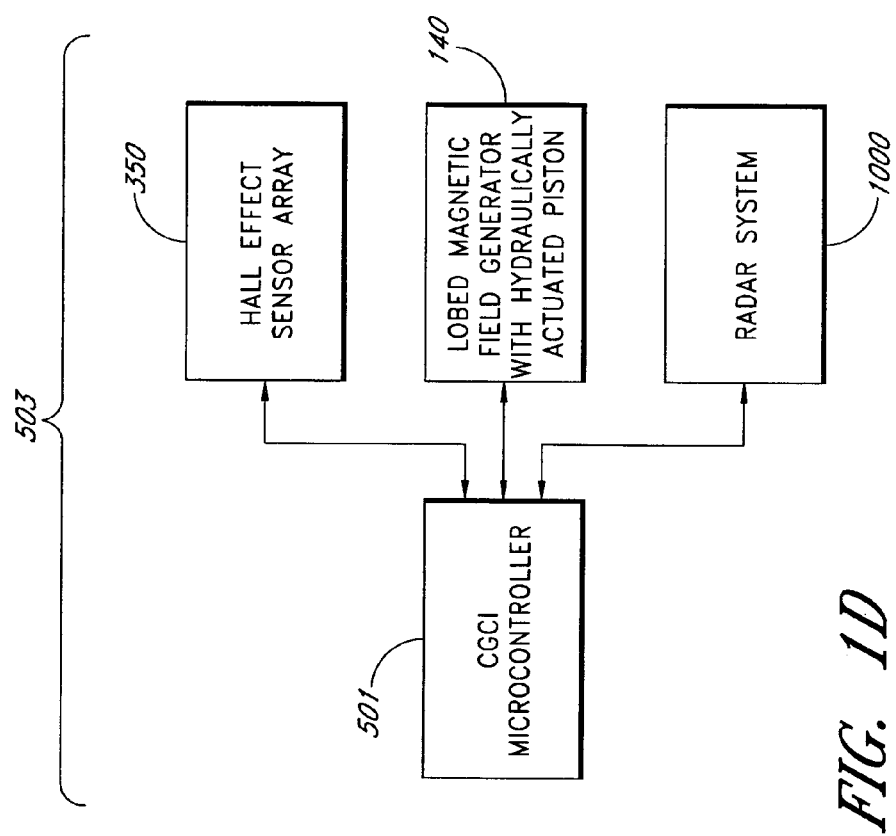
FIG. 1D is a block diagram of the imaging module for use in a CGCI surgery procedure that includes the catheter guidance system, a radar system, Hall Effect sensors, and a hydraulically actuating core extension mechanism.

FIG. 1D is a block diagram of a surgery system 503 that represents one embodiment of the CGCI system 1500. The system 503 includes the controller 501, a radar system 1000, a Hall effect sensor array 350 and the hydraulically-actuated mechanism 140. In one embodiment, the sensor 350 includes one or more Hall effect magnetic sensors as described in connection with FIG. 34. The radar system 1000 can be configured as an ultra-wideband radar, an impulse radar, a Continuous-Wave (CW) radar, a Frequency-Modulated CW (FM-CW) radar, a pulse-Doppler radar, etc. In one embodiment, the radar system 1000 uses Synthetic Aperture Radar (SAR) processing to produce a radar image. In one embodiment, the radar system 1000 includes an ultra-wideband radar such as described, for example, in U.S. Pat. No. 5,774,091, hereby incorporated by reference in its entirety. In one embodiment, the radar 1000 is configured as a radar range finder to identify the location of the catheter tip 377. The radar 1000 is configured to locate reference markers (fiduciary markers) placed on the patient 390. Data regarding location of the reference markers can be used, for example, for image capture synchronization 701. The motorized hydraulically and actuated motion control mechanism 140 allows the electromagnets of the cylindrical coils 51AT and 51DT to be moved relative to the patient 390.

In one embodiment, the use of the radar for identifying the position of the catheter tip 377 has advantages over the use of Fluoroscopy, Ultrasound, Magnetostrictive sensors, or SQUID. Radar can provide accurate dynamic position information, which provides for real-time, relatively high resolution, relatively high fidelity compatibility in the presence of strong magnetic fields. Self-calibration of the range measurement can be based on time-of-flight and/or Doppler processing. Radar further provides for measurement of catheter position while ignoring "Hard" surfaces such as a rib cage, bone structure, etc., as these do not interfere with measurement or hamper accuracy of the measurement. In addition, movement and displacement of organs (e.g., pulmonary expansion and rib cage displacement as well as cardio output during diastole or systole) do not require an adjustment or correction of the radar signal. Radar can be used in the presence of movement since radar burst emission above 1 GHz can be used with sampling rates of 50 Hz or more, while heart movement and catheter dynamics occur at 0.1 Hz to 2 Hz.

In one embodiment, the use of the radar 1000 reduces the need for complex image capture techniques normally associated with expensive modalities such as fluoroscopy, ultrasound, Magnetostrictive technology, or SQUID which require computationally-intensive processing in order to translate the pictorial view and reduce it to a coordinate data set. Position data synchronization of the catheter tip 377 and the organ in motion is readily available through the use of the radar 1000. The radar 1000 can be used with phased-array or Synthetic Aperture processing to develop detailed images of the catheter location in the body and the structures of the body. In one embodiment, the radar system includes an Ultra Wide Band (UWB) radar with a relatively high resolution swept range gate. In one embodiment, a differential sampling receiver is used to effectively reduce ringing and other aberrations included in the receiver by the near proximity of the transmit antenna. As with X-ray systems, the radar system can detect the presence of obstacles or objects located behind barriers such as bone structures. The presence of different substances with different dielectric constants such as fat tissue, muscle tissue, water, etc., can be detected and discerned. The outputs from the radar can be correlated with similar units such as multiple catheters used in Electro-Physiology (EP) studies while detecting spatial location of other catheters present in the heart lumen. The radar system 1000 can use a phased array antenna and/or SAR to produce 3D synthetic radar images of the body structures, catheter tip and organs.

In one embodiment, the location of the patient relative to the CGCI system (including the radar system 1000) can be determined by using the radar 1000 to locate a plurality of fiduciary markers. In one embodiment, the data from the radar 1000 is used to locate the body with respect to an imaging system. The catheter position data from the radar 1000 can be superimposed (synchronized) with the images produced by the imaging system. The ability of the radar and the optional Hall effect sensors 350 to accurately position the catheter tip 377 relative to the stereotactic frame allows the pole pieces to be moved by the actuators 109, 140 to optimize the location of the magnet poles with respect to the patient 390 and thus reduce the power needed to manipulate the catheter tip.

Figures 2, 2A:
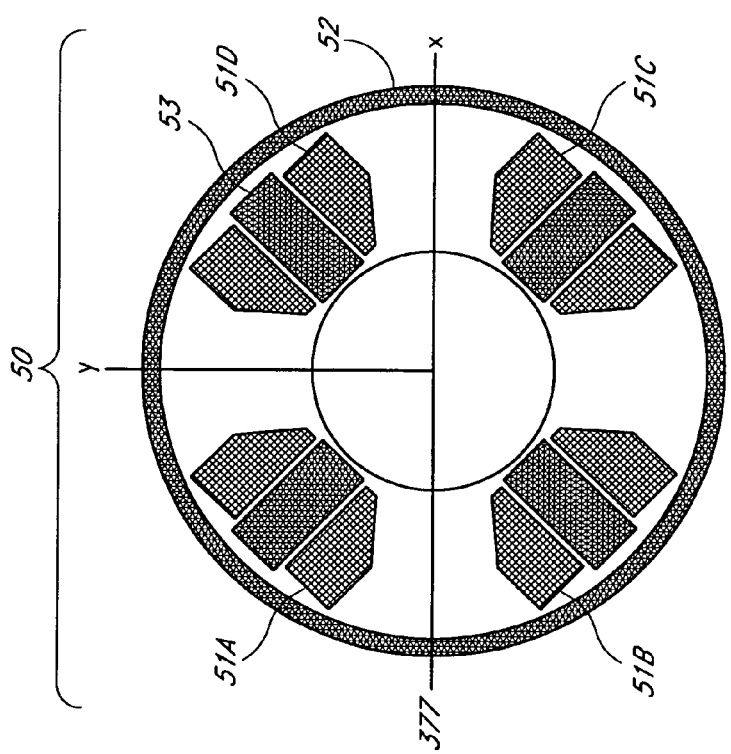
FIG. 2 shows a magnet assembly of a CGCI scale model.
FIG. 2A shows parameters of the assembly shown in FIG. 2.

FIGS. 2 and 2A show the construction of a demonstration unit 50 having an effective field region of 80 mm.

The scale model 50 is constructed using four coils 51A, 51B, 51C, and 51D in the XY plane. The 2D configuration is supplemented with a flux return ring 52. The coil 51D is provided with an extendable iron core 53. The scale model 50 is approximately one-eighth the size of the full-scale CGCI apparatus. The full size expansion is based on the four-coil XY plane (2D) scale-model 50, and a dual three plus three coil cluster XYZ (3D) 1500. The results in terms of geometry optimization as well as the topological transformation from 2D to 3D resulting in the six coil CGCI configuration 1500 is enhanced by the use of the hydraulically operated pole pieces 111,161. These movable pole pieces 111, 161 aid the magnetic shaping function by reducing coil size and power requirements. The optimization of the electromagnetic circuit is obtained as a geometrical expansion of the 2D scale model 50 further augmented by the topological transformation of the 3D model, which results in the CGCI unit 1500.

In one embodiment, the system provides a 0.15-0.3 Tesla field density for torque control and a 1.6-3.0 Tesla/m field gradient for force control within the center region. Using a 4 mm×10 mm size NbFe35 permanent magnet in the catheter tip 377, the CGCI apparatus is able to achieve a force of 35 grams for catheter movement. The six coil cluster can generate a magnetic field in the center region of the cluster to exert a torque on the catheter tip 377 in the desired direction, without an advancing force on the tip. This torque force is used to bend and rotate the tip toward the selected direction. The magnetic field can also be configured to generate a relatively high field gradient in the center region for exerting a moving force on the tip (e.g., push-pull force), but without rotating torque on the tip.

The magnetic field can also generate a relatively high field gradient in the region for exerting a orthogonal force on the tip (sideways movement), without rotating torque on the tip. This is useful, for example, to align the tip at narrow forks of artery passages and for cleaning the sides of an artery.

The magnetic field can also generate a mixed relatively high field strength and field gradient to push/pull and/or bend/rotate the tip simultaneously. This is useful, for example, to guide the tip while it is moving in curved arteries.

In one embodiment, the 80 mm scale model 50 shown in FIG. 2 is expanded to a full scale CGCI machine 1500 (600 mm diameter) by using the scaling equation:

$$AT(r) = \left(2*\sqrt{3}\right)^{\frac{ln(r)}{ln(2)}} \quad \text{where} \quad r = \frac{D_{scale}}{D_{Demo}} = \frac{D_{scale}\text{mm}}{80 \text{ mm}} \quad (1)$$

Scaling the demonstration unit 50 pole face diameters (PF) of the scale model SO to the CGCI full scale (600 mm) follows the pole face diameter scaling multiplier.

$$PF(r) = \left(2*\sqrt{2}\right)^{\frac{ln(r)}{ln(2)}} \quad (2)$$

Forces on the catheter tip 377 permanent magnet (NbFe35) shown in FIG. 2A (2 mm radius and 10 mm length) are calculated as the force on a dipole in a magnetic field.

$$F_M = \nabla(B \cdot M) \quad (3)$$

Where M is the dipole magnetization vector and B is the field density vector around the dipole. Calculating B along axis S of the dipole, using the scalar derivative 404 gives $$F_S = M \cdot A_m \cdot L_m \cdot \frac{\partial B}{\partial s}, \quad (4)$$

where $A_m$ is the magnetic cross section and $L_m$ is its length. For $$\frac{\partial B}{\partial s} = 1.6 \, \frac{Tesla}{m} \quad \text{and} \quad M = 980,000 \, \frac{amp}{m}, \quad \text{then} \quad F_s + 20.1 \text{ gram.}$$

For a maximum gradient of $$\frac{\partial B}{\partial s} = 3 \frac{Tesla}{m}$$

and when deploying the extractable core 53, the force generates is $$F_S = 37 \text{ gram.}$$

The torque on the same size catheter tip 377 is calculated as the torque on the permanent magnet in field B is $T_m = M \cdot B \cdot A_m \cdot L_m \cdot \sin(\theta)$, where θ is angle between the magnet axis and B.

For B=0.15 Tesla and an operating angle of θ=45°, $T_m$=0.013 Newton·m, and the torque on a 10 mm arm with a 35 gram force is $T_{35g}$=0.0034 Newton·m.

In one embodiment, the field strength for this torque is B=0.04 Tesla. Using B=0.15 Tesla yields a bending arm of 38 mm.

Using the scale factors in Equations 1 and 2 along with Equations 3 and 4 allows the design of CGCI apparatus 1500 to accomplish the desired tasks of control and navigation of the catheter tip 377.

Figure 2D:
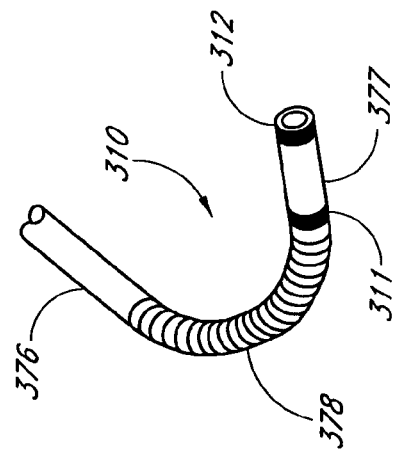
FIG. 2D shows a catheter assembly with piezoelectric rings.
Figure 2C:
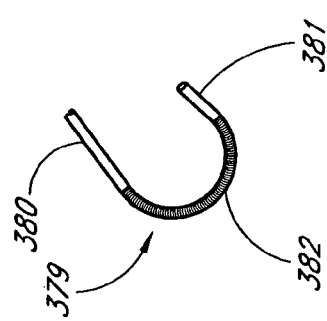
FIG. 2C is a second view of the catheter assembly.
Figure 2B:
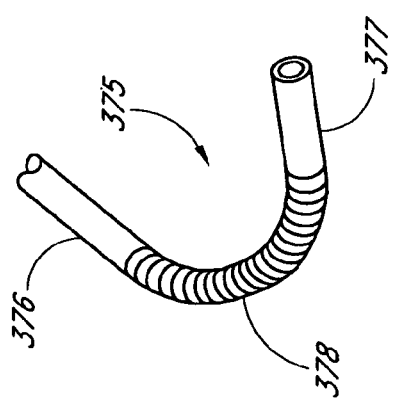
FIG. 2B is a first view of the catheter assembly.

FIGS. 2B and 2C shows one embodiment of a catheter assembly 375 and guidewire assembly 379 to be used with the CGCI apparatus 1500. The catheter assembly 375 is a tubular tool that includes a catheter body 376 which extends into a flexible section 378 that possesses sufficient flexibility for allowing a relatively more rigid responsive tip 377 to be steered through the patient.

In one embodiment, the magnetic catheter assembly 375 in combination with the CGCI apparatus 1500 reduces or eliminates the need for the plethora of shapes normally needed to perform diagnostic and therapeutic procedures. During a conventional catheterization procedure, the surgeon often encounters difficulty in guiding the conventional catheter to the desired position, since the process is manual and relies on manual dexterity to maneuver the catheter through a tortuous path of, for example, the cardiovascular system. Thus, a plethora of catheters in varying sizes and shapes are to be made available to the surgeon in order to assist him/her in the task, since such, tasks require different bends in different situations due to natural anatomical variations within and between patients.

By using the CGCI apparatus 1500, only a single catheter is needed for most, if not all patients. The catheterization procedure is now achieved with the help of the CGCI system 1500 that guides the magnetic catheter and guidewire assembly 375 and 379 to the desired position within the patient's body 390 as dictated by the surgeon's manipulation of the virtual tip 905. The magnetic catheter and guidewire assembly 375, 379 (i.e. the magnetic tip 377 can be attracted or repelled by the electromagnets of the CGCI apparatus 1500) provides the flexibility needed to overcome tortuous paths, since the CGCI apparatus 1500 overcomes most, if not all the physical limitations faced by the surgeon while attempting to manually advance the catheter tip 377 through the patient's body.

In one embodiment, the catheter tip 377 includes a guidewire assembly 379, a guidewire body 380 and a tip 381 response to magnetic fields. The Tip 377 steered around sharp bends so as to navigate a torturous path. The responsive tips 377 and 381 of both the catheter assembly 375 and the guidewire assembly 379, respectively, include magnetic elements such as permanent magnets. The tips 377 and 381 include permanent magnets that respond to the external flux generated by the electromagnets 110, 115, 116 and its symmetric counterpart 100.

In one embodiment, the responsive tip 377 of the catheter assembly 375 is tubular, and the responsive tip 381 of the guidewire assembly 379 is a solid cylinder. The responsive tip 377 of the catheter assembly 375 is a dipole with longitudinal polar orientation created by the two ends of the magnetic element positioned longitudinally within it. The responsive tip 381 of the guidewire assembly 379 is a dipole with longitudinal polar orientation created by two ends of the magnetic element 377 positioned longitudinally within it. These longitudinal dipoles allow the manipulation of both responsive tip 377 and 381 with the CGCI apparatus 1500, as the electromagnet assemblies 100, 101, and will act on the tips 377 and 381 and "drag" them in unison to a desired position as dictated by the operator.

FIG. 2D shows a catheter assembly 310 with two piezoelectric rings 311, and 312, located as shown. An ultrasonic detector in combination with the apparatus 1500 provides an additional detection modality of the catheter tip wherein an ultrasonic signal is used to excite the two piezoelectric rings and provide a measure of rotation of the catheter tip relative to the North Pole axis of the magnet 377. With aid of the computer 324, the CGCI apparatus 1500 is configured to determine an angle of rotation of the tip 377. The piezoelectric rings 311, 312 can also provide additional position information to determine the position, orientation, and rotation of the catheter tip 377 relative to the stereotactic framing available from the fiduciary markers described in connection with FIGS. 30D and 30E.

FIGS. 3, 3A, and 4 are orthographic representations of the scale model 50 shown in FIGS. 2 and 2A. In the scale model 50, the coil assemblies 51A, 51B, 51C, and 51D are combined with the coil the direction rule in Equation 9 and the resultant B field direction in Equation 8 in combination allow the operator interface equipment 500 and its user input devices to direct and navigate the catheter tip 377 to its desired position (DP).

Using the scaling rules in Equations 8 and 9, one can expand the 80 mm scale model 50 to its CGCI 1500 scale of 600 mm or more. The scale model 50 is defined on the XY plane 2D configuration shown in FIGS. 3 and 3A. Coil assemblies 51A, 51B, 51C, and 51D are mounted as shown on the XY 2D plane and each includes a coil with its associated core made of 1018 iron. The cores are provided to an actuator that can extend or retract the cores.

In one embodiment, each pole core is tangential to the 80 mm inner circle identified as the operating region/effective magnetic space 419. The core extension 53 is deployed by moving the hydraulically-actuated piston toward the operating table. FIG. 3A shows a deployed core extension.

Depending on the current directions and magnitudes in the coils, the center region can be set up for magnetic fields producing just torque, just force, or mixed torque and force. In the Torque Mode, four combinations of coil current directions in A, B, C, and D magnets produce an approximately uniform B field in the center region 419. The main B field vector directions (90° rotations) follow a rotational rule shown in FIG. 4.

Figure 5:
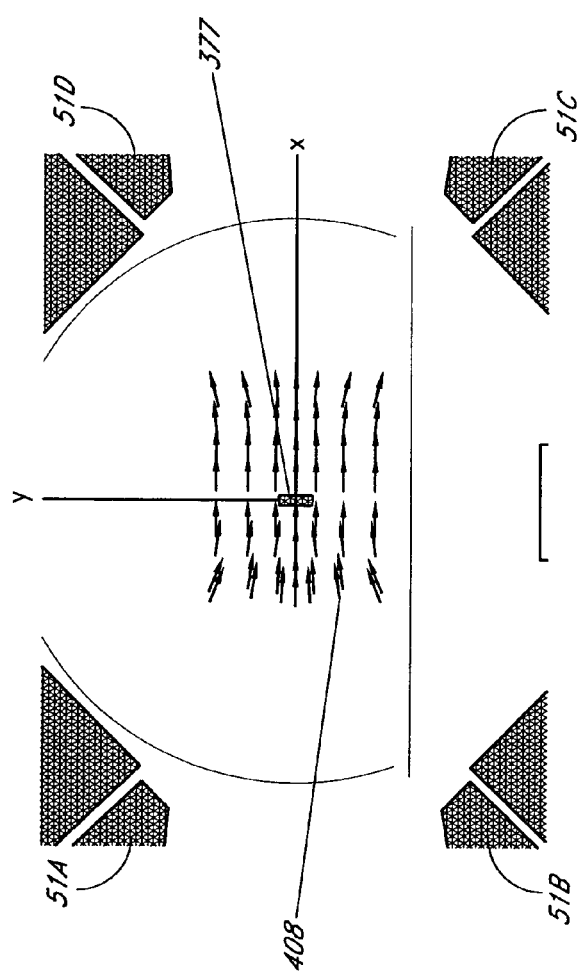
FIG. 5 is a vector field plot of the B fields in a central region of the magnet assembly of FIG. 3 with a first current configuration where the B-vector is parallel to the X-axis.
Figure 5A:
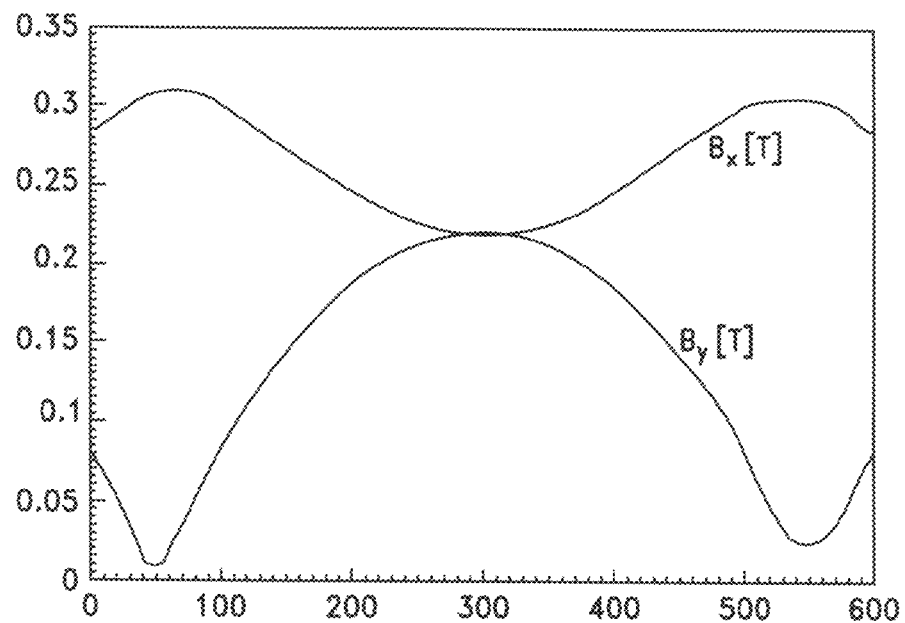
FIG. 5A is a field intensity plot corresponding to FIG. 5.
Figure 5B:
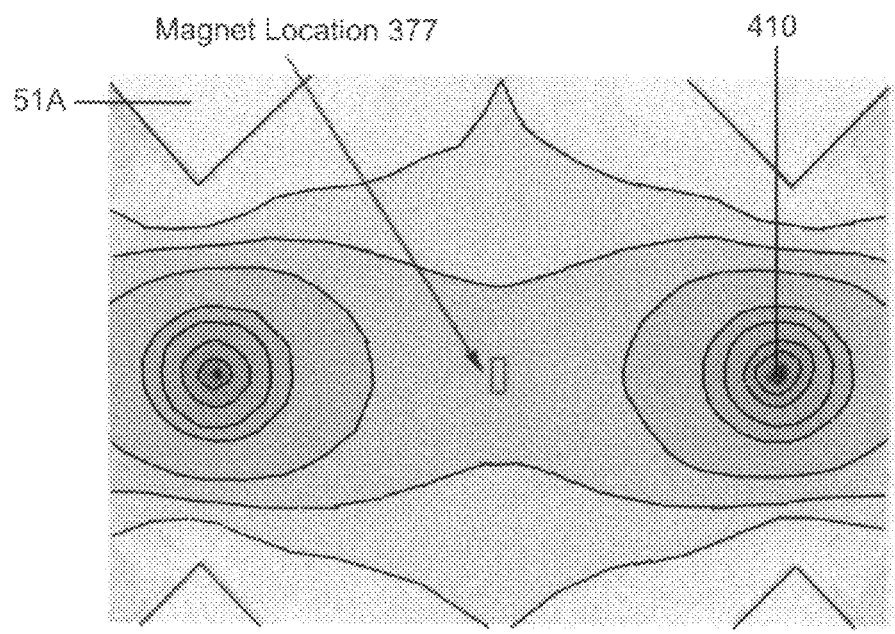
FIG. 5B is a field contour plot corresponding to FIG. 5.

FIGS. 5, 5A, and 5B illustrate the scalability equations 1-4 as applied to the coil current direction and the resultant B field direction.

The B vector is parallel to the +X axis and within the central region B is about 0.23 Tesla. The torque at a 45° angle between B and the magnet is 0.03 Newton meters.

In FIG. 5, the case +X shows application of the coil current direction. The B field direction and the resultant position of the catheter tip 377, in the effective region 419 are shown. FIG. 5B shows the field intensity as a gradation from black to white on a scale of 0.02-0.4 Tesla. The electromagnetic circuit formed by coils 51A, 51B, 51C, and 51D applied in the effective region 419 and manipulated by the coil current direction and the B field direction generates the torque as well as force predicted by Equations 3 and 4.

Figure 6:
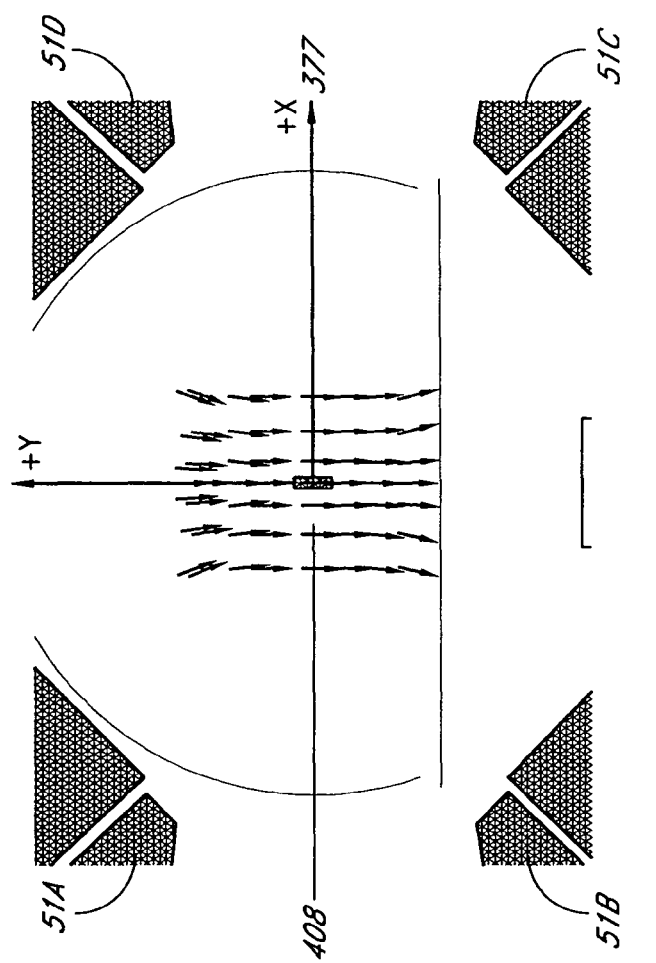
FIG. 6 is a vector field plot of the B fields in a central region of the magnet assembly of FIG. 3 with a second current configuration where the B-vector is parallel to the Y-axis.
Figure 6A:
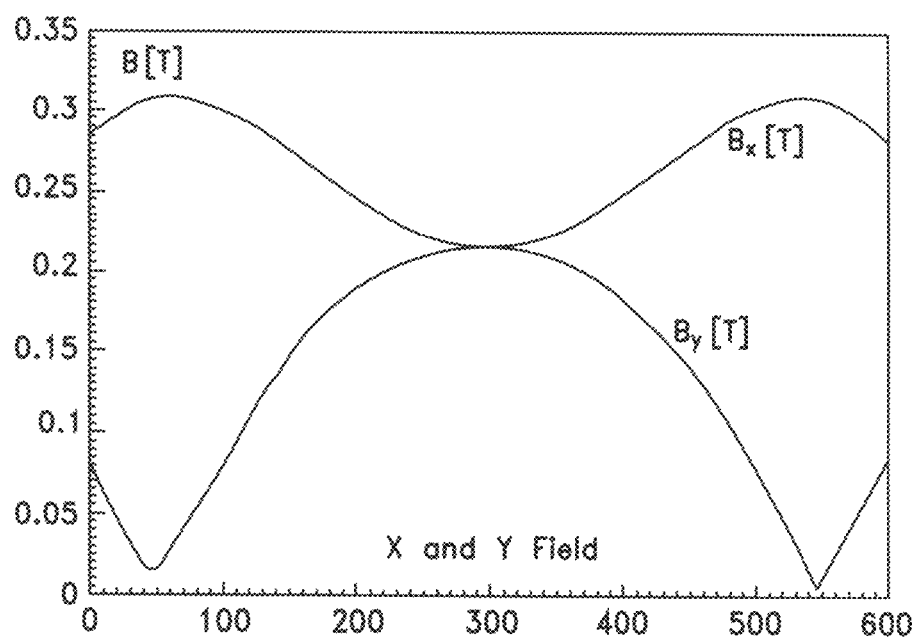
FIG. 6A is a field intensity plot corresponding to FIG. 6.
Figure 6B:
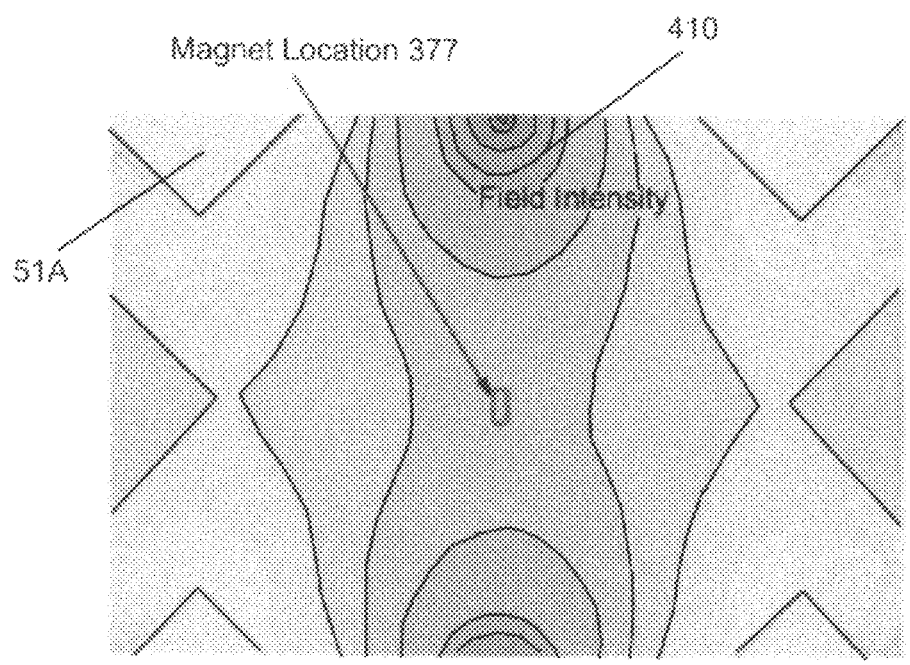
FIG. 6B is a field contour plot corresponding to FIG. 6.

FIGS. 6, 6A, and 6B show the predicting capability of the scaling Equations 1 and 2 as to the behavior of the electromagnetic circuit and the scale model 50. FIG. 6 further shows a case where the B vector is parallel to the −Y axis and within the central region/effective space 419 (±50 mm around the 300 mm mark). B is about 0.23 Tesla, the torque is at a 45° angle between B and the magnet 377 is 0.03 Newton meters. FIGS. 6, 6A, and 6B further confirm the accuracy of the scaling Equations 1 and 2.

Figure 7:
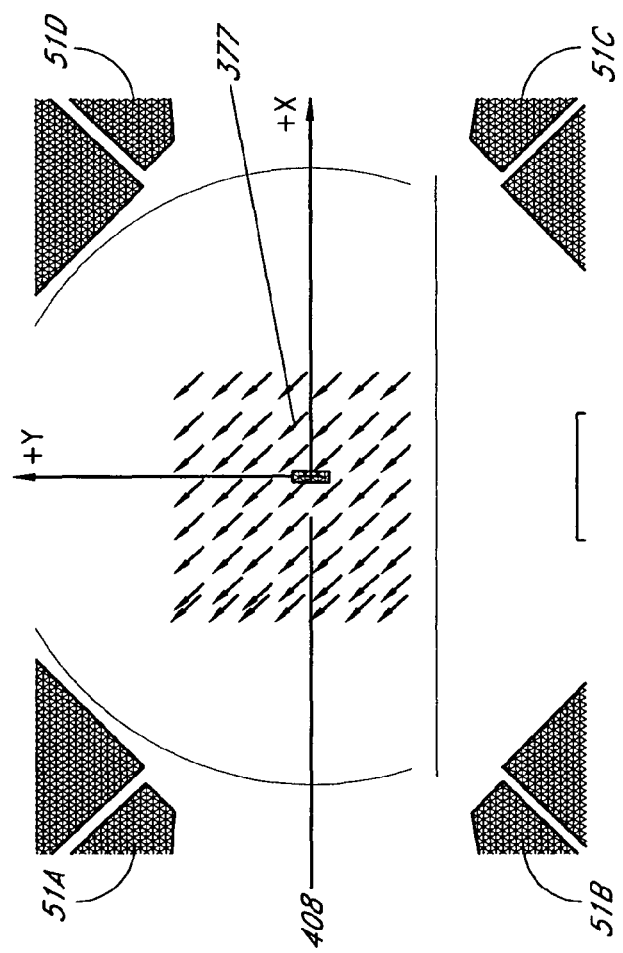
FIG. 7 is a vector field plot of the B fields in a central region of the magnet assembly of FIG. 3 with a third current configuration where the B-vector direction is 135°.
Figure 7A:
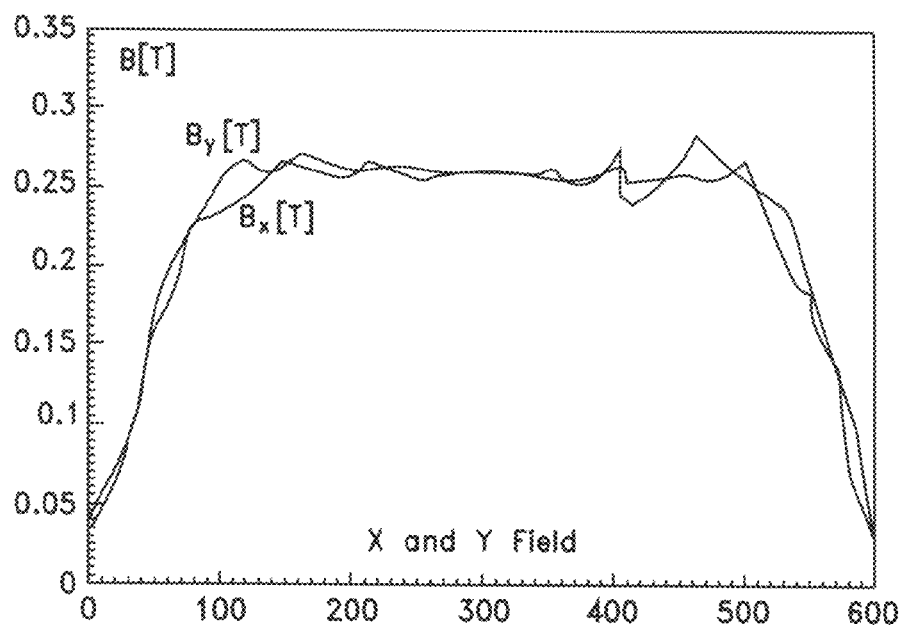
FIG. 7A is a field intensity plot corresponding to FIG. 7.
Figure 7B:
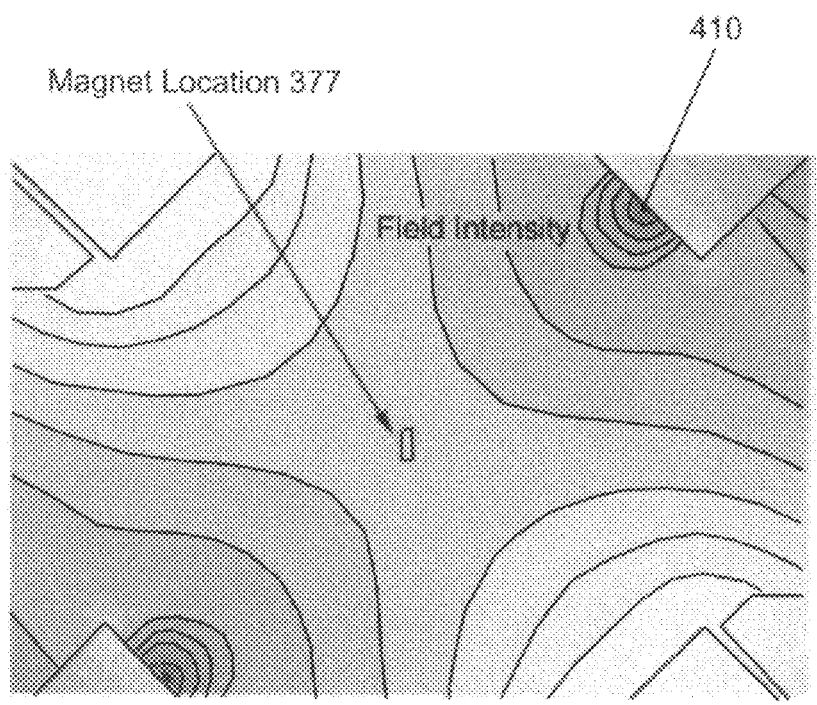
FIG. 7B is a field contour plot corresponding to FIG. 7.

FIGS. 7, 7A, and 7B show the scaling Equations 1 and 2 in a boundary condition where the B vector is pointing to the coil pole face 51A within the central region/effective space 419. B is about 0.195 Tesla. This 135° B vector direction is accomplished by setting the scale model 50 such that current in the coil 51A is directed as CCW, the current direction in the coil 51C is CW and the coil current of coils 51B and 51C are set at zero.

Figure 8:
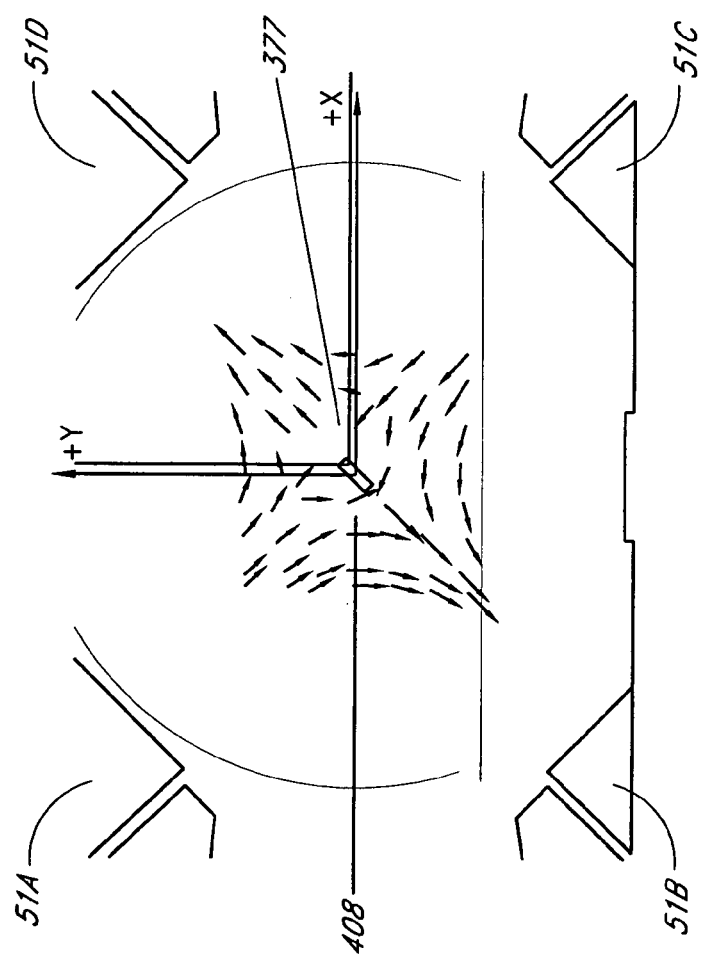
FIG. 8 is a vector field plot of the B fields in a central region of the magnet assembly of FIG. 3 with a fourth current configuration corresponding to the force control mode.
Figure 8A:
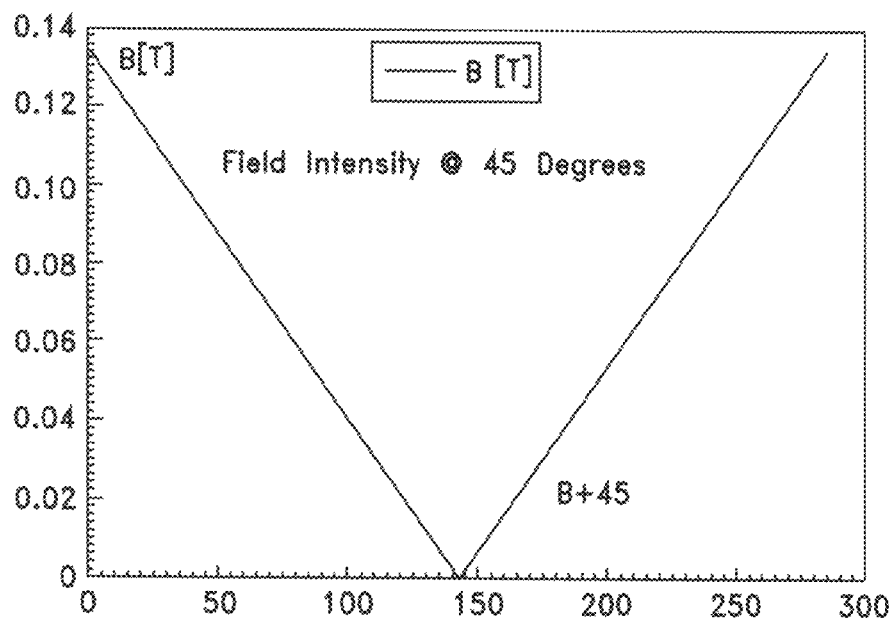
FIG. 8A is a field intensity plot corresponding to FIG. 8.
Figure 8B:
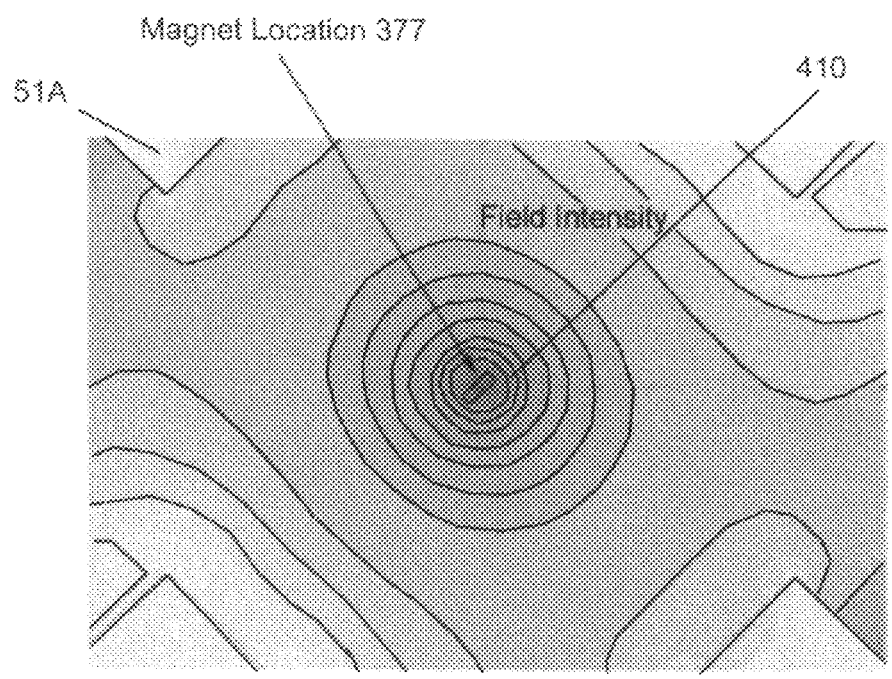
FIG. 8B is a field contour plot corresponding to FIG. 8.

FIGS. 8, 8A, and 8B illustrate the behavior of the scale model 50 in a force control mode along the magnet axis with zero torque on the tip 377. In this case, coil 51D in a CCW current direction, coil 51B has CCW current, and coils 51A and 51C are set to zero current. The resultant force is 12 grams.

Figure 9:
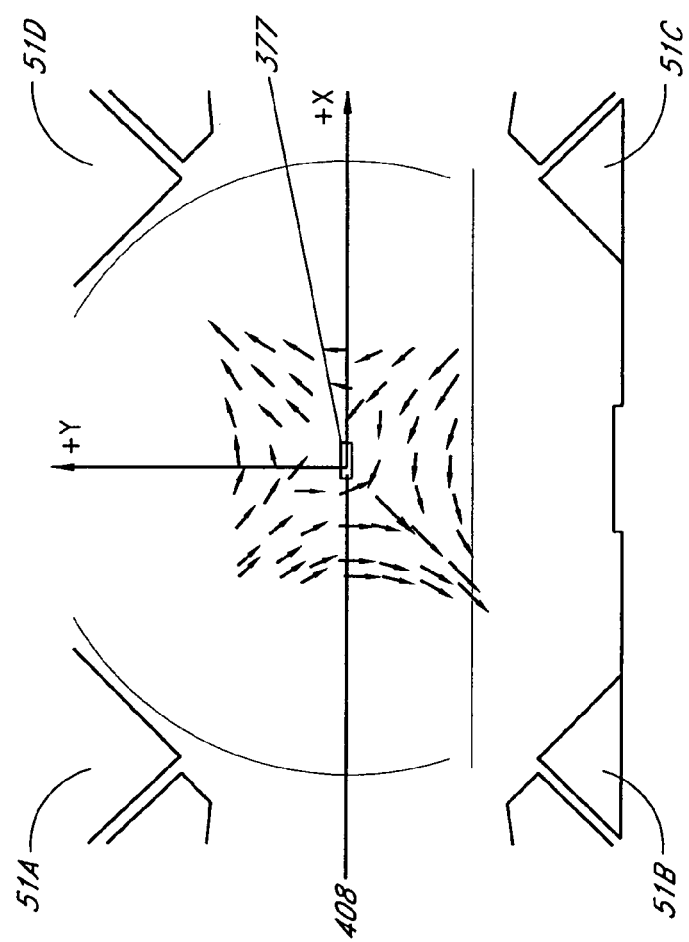
FIG. 9 is a vector field plot of the B fields in a central region of the magnet assembly of FIG. 3 with a fifth current configuration in the force control mode where the B vector is orthogonal to the magnetic tip axis.
Figure 9A:
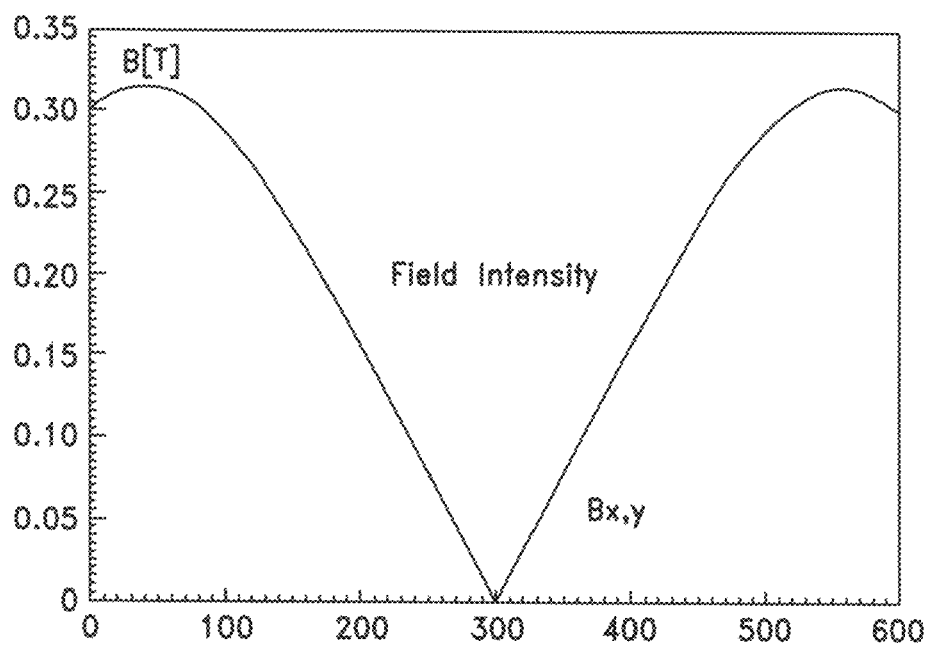
FIG. 9A is a field intensity plot corresponding to FIG. 9.
Figure 9B:
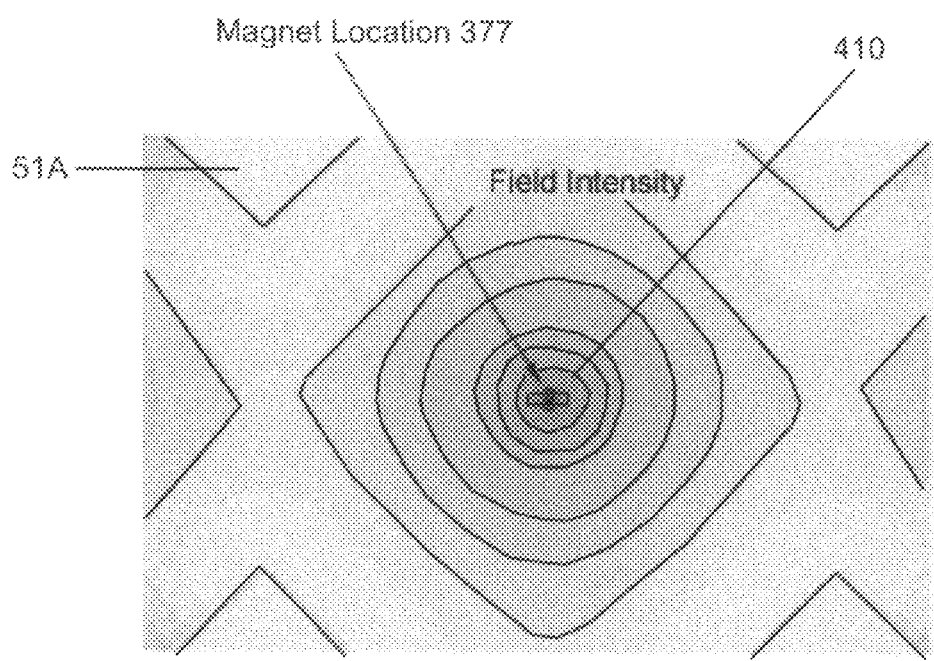
FIG. 9B is a field contour plot corresponding to FIG. 9.

FIGS. 9, 9A, and 9B illustrate the force control mode 406, orthogonal to the magnet axis with a substantially zero torque on the catheter tip 377. In this case, the coil 51A is set at CW, and the coil 51B is set at CCW, the coil 51C at CW direction, and the coil 51D direction is CCW. The force is 22 grams.

Figure 10:
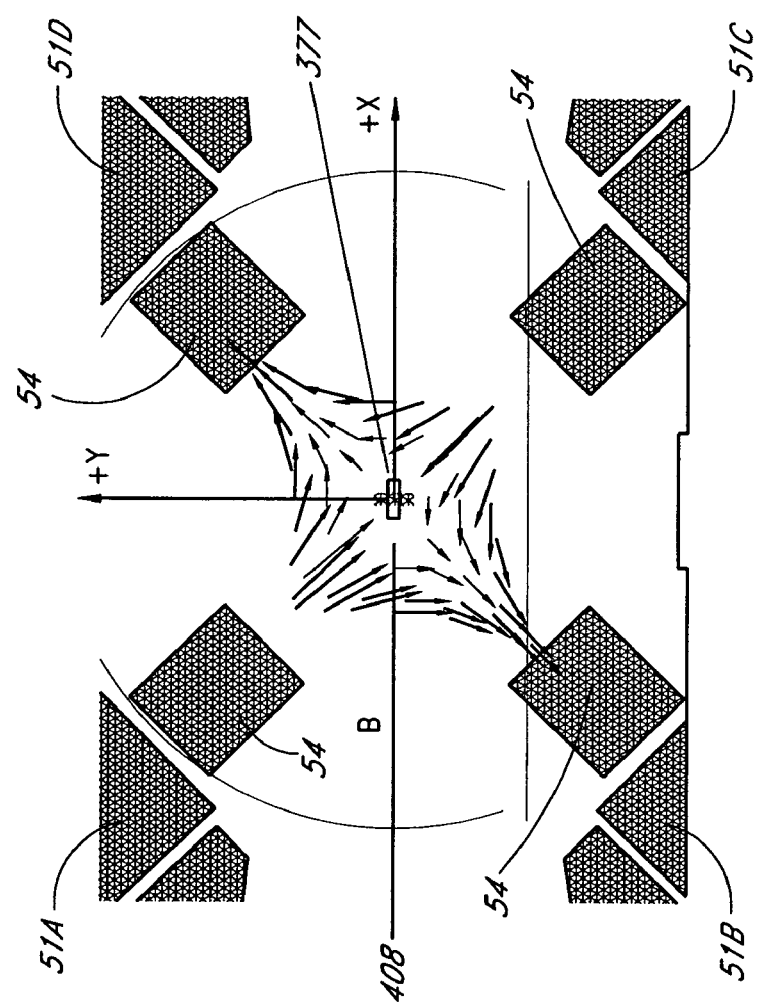
FIG. 10 is a vector field plot of the B fields in a central region of the magnet assembly of FIG. 3 with a sixth current configuration with a hydraulically extended core.
Figure 10A:
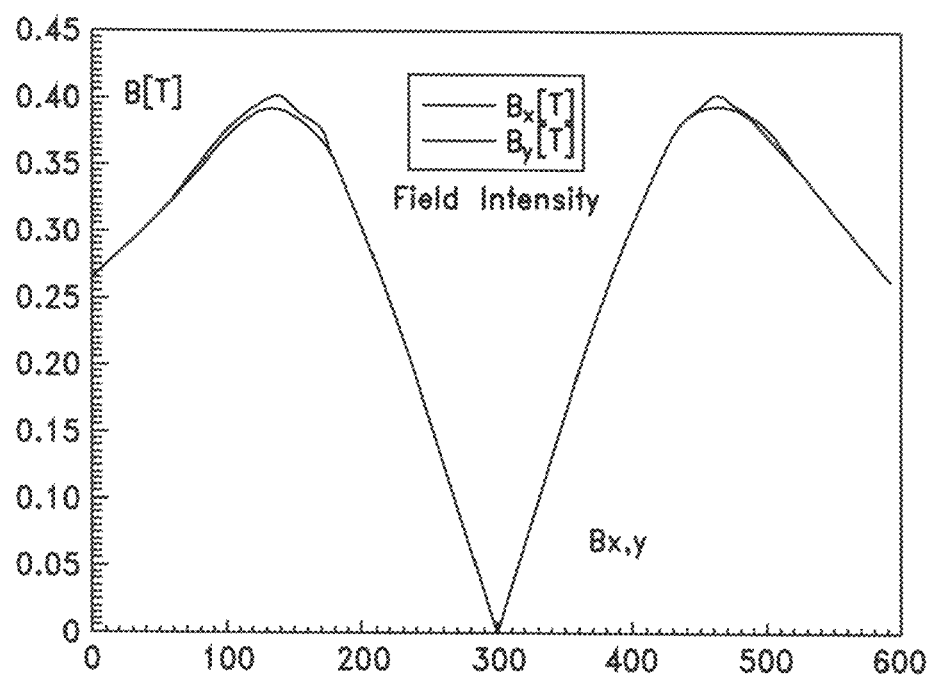
FIG. 10A is a field intensity plot corresponding to FIG. 10.
Figure 10B:
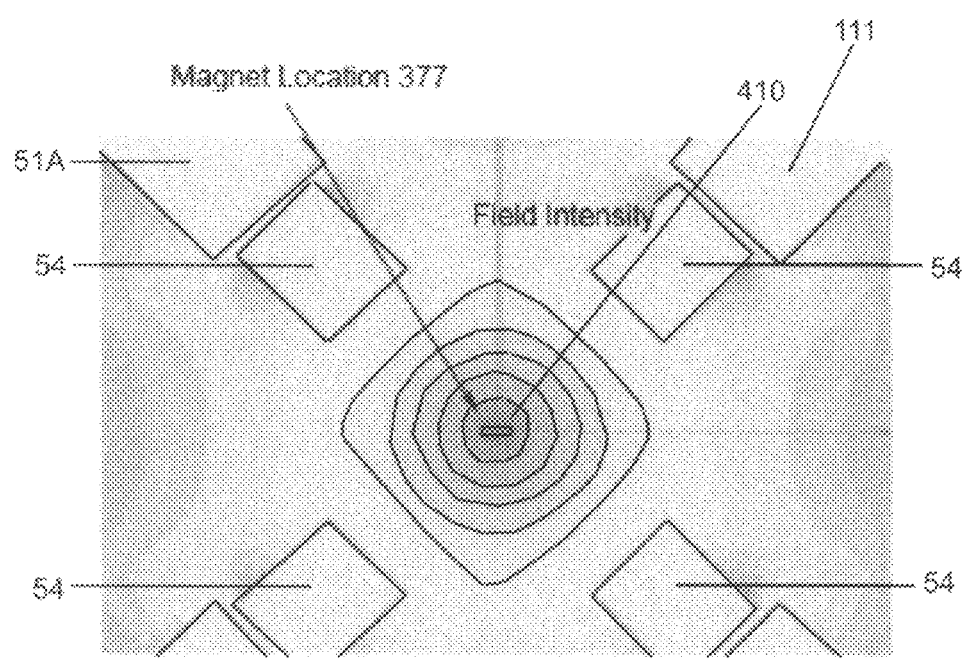
FIG. 10B is a field contour plot corresponding to FIG. 10.

FIGS. 10, 10A and 10B show the scale model 50 as it is set for the force control mode. This case illustrates the use of the hydraulically extended piston with its core extension rod 53. The core extension 53 varies the magnetic field characteristics as disclosed below. FIGS. 10, 10A and 10B illustrate the model 50 in the force control mode when the four cores are extended into the effective space 419 and where the coil 51A is set to CW, the coil 51B set to CCW, the coil 51C to CW and the coil 51D is set to CCW. The resultant field geometry produces a force of 37 grams on the catheter tip 377.

Figure 11:
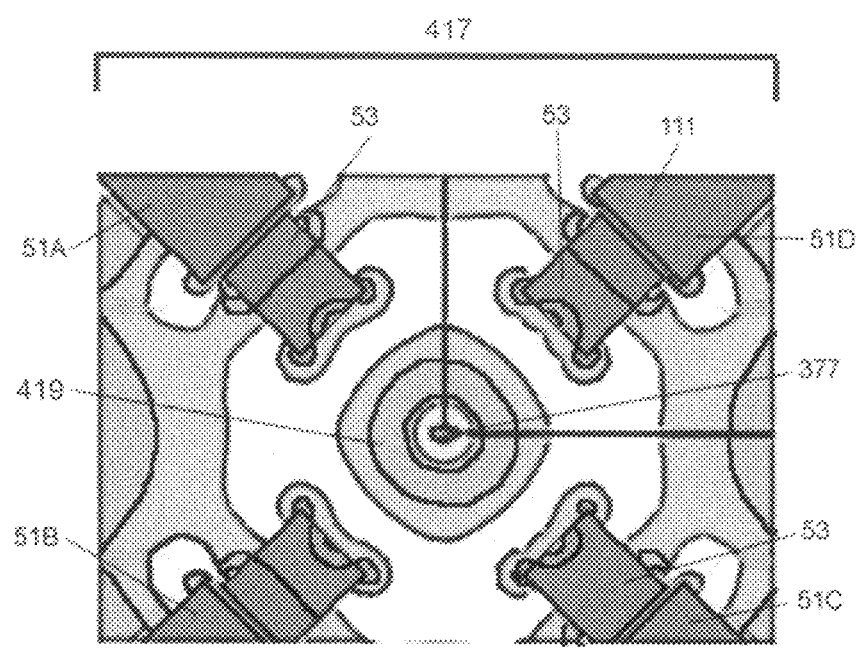
FIG. 11 shows the magnetic fields with a first core extension configuration.

FIG. 11 shows the four-coil formation 51A, 51B, 51C and 51D when the magnetic core extensions 53 are deployed into the effective region 419. FIG. 11 further shows that by deploying the magnetic core extensions, the magnetic field is shaped. FIG. 11 also shows the resulting magnetic field is relatively symmetrical around the catheter tip 377.

Figure 11A:
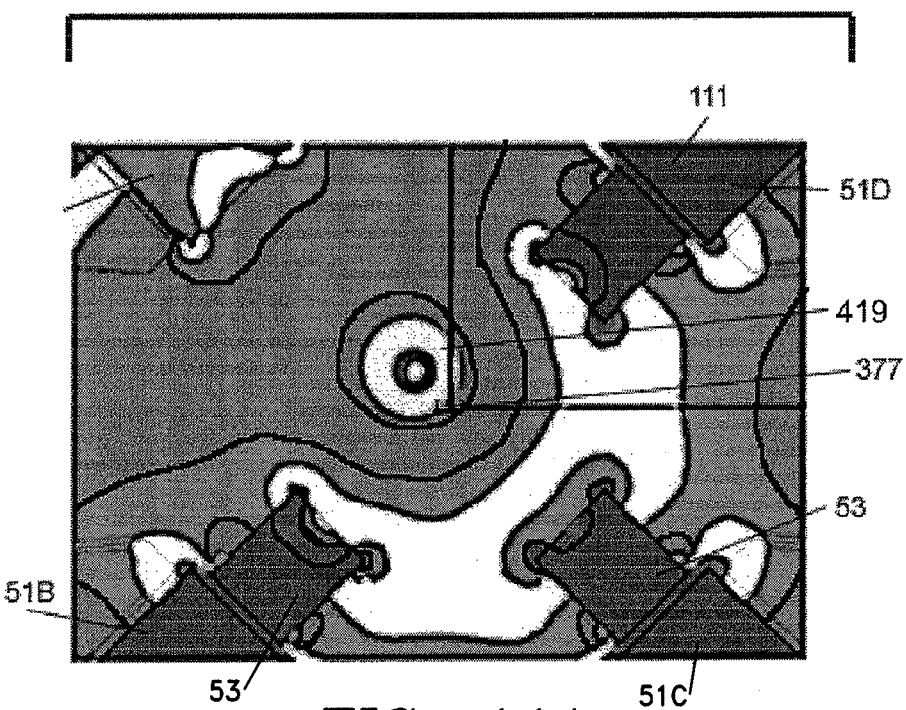
FIG. 11A shows the magnetic fields with a second core extension configuration.

FIG. 11A shows the core coil 51A with its core withdrawn, hence forming a new geometry configured to generate a shaped magnetic field for better control of the catheter movements in the effective space 419.

Figure 11B:
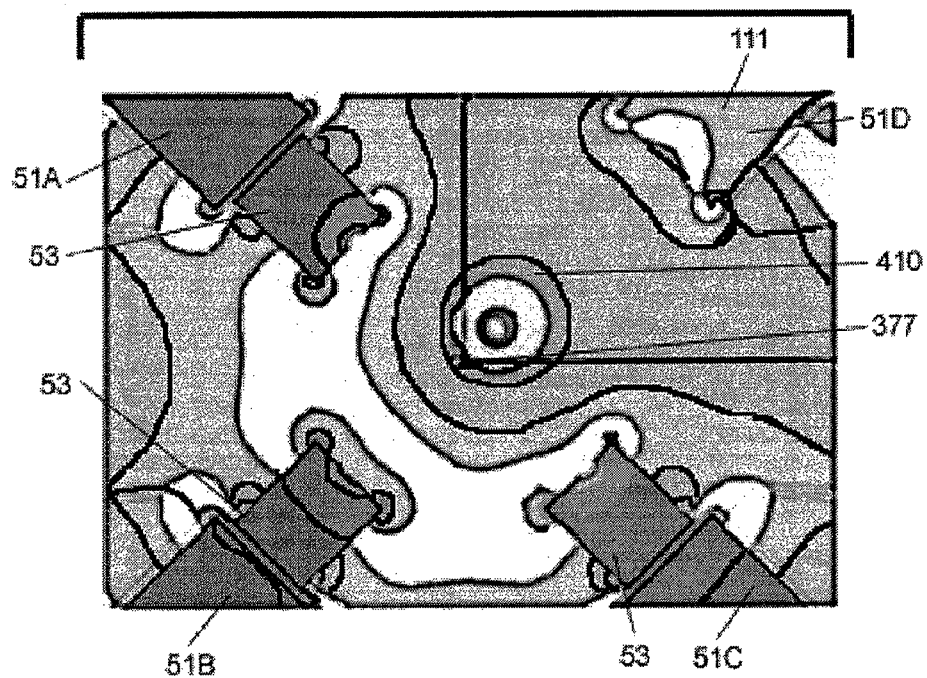
FIG. 11B shows the magnetic fields with a third core extension configuration.

FIG. 11B shows the shaped magnetic field when the core on coil 51D is retracted.

FIGS. 12 and 12A show the CGCI apparatus 1500 and magnetic field where the magnetic field is generated by actuating and deploying the core extensions. As shown in FIG. 12, when the current on coil 51C is set at zero, the field has a similar geometry to that in FIGS. 11A and 11B, respectively. In the case of FIGS. 12 and 12A, when the current of coils 51B and 51C are set at substantially zero, the magnetic extension core 53 and its associated hydraulic actuating piston can vary the deployment distance and hence vary the field geometry relative to its respective position. The shaped magnetic field using the actuator-deployed variable-length extension cores allows the creation of an effective magnetic field geometry for control and navigation of the CGCI catheter tip 377.

FIGS. 12B, 12C, 12D, 12E, 12F and 12G show the CGCI apparatus 1500 wherein a combination of the cores and current control are used in shaping the magnetic field characteristics. The resultant magnetic field geometry allows the CGCI apparatus 1500 to shape the magnetic field by varying the magnetic circuit characteristics by extending and/or retracting the cores while varying the PWM duty cycle on the power supply. The cores are identified as 51AT through 51DT respectively. FIG. 12B shows a condition wherein the core 51AT is deployed while core 51DT is retracted. The magnetic field is measured along the XZ plane.

FIG. 12C shows the cores 51AT and 51DT fully extended. The magnet current is set at 1%.

FIG. 12D shows the coils 51B and 51C where current control is set at 1% along the YZ plane.

FIG. 12E shows a condition wherein core 51AT is retracted. The forces are shown on the XZ plane.

FIG. 12F shows the coils 51B and 51C at a current of 1% on the XZ plane where the geometry accommodates the catheter tip control as shown.

FIG. 12G is a graphic representation of coil currents 51A and 51B at +100%, coils 51C and coil 51D are at −100% and 1% respectively along the XY plane.

Figure 14:
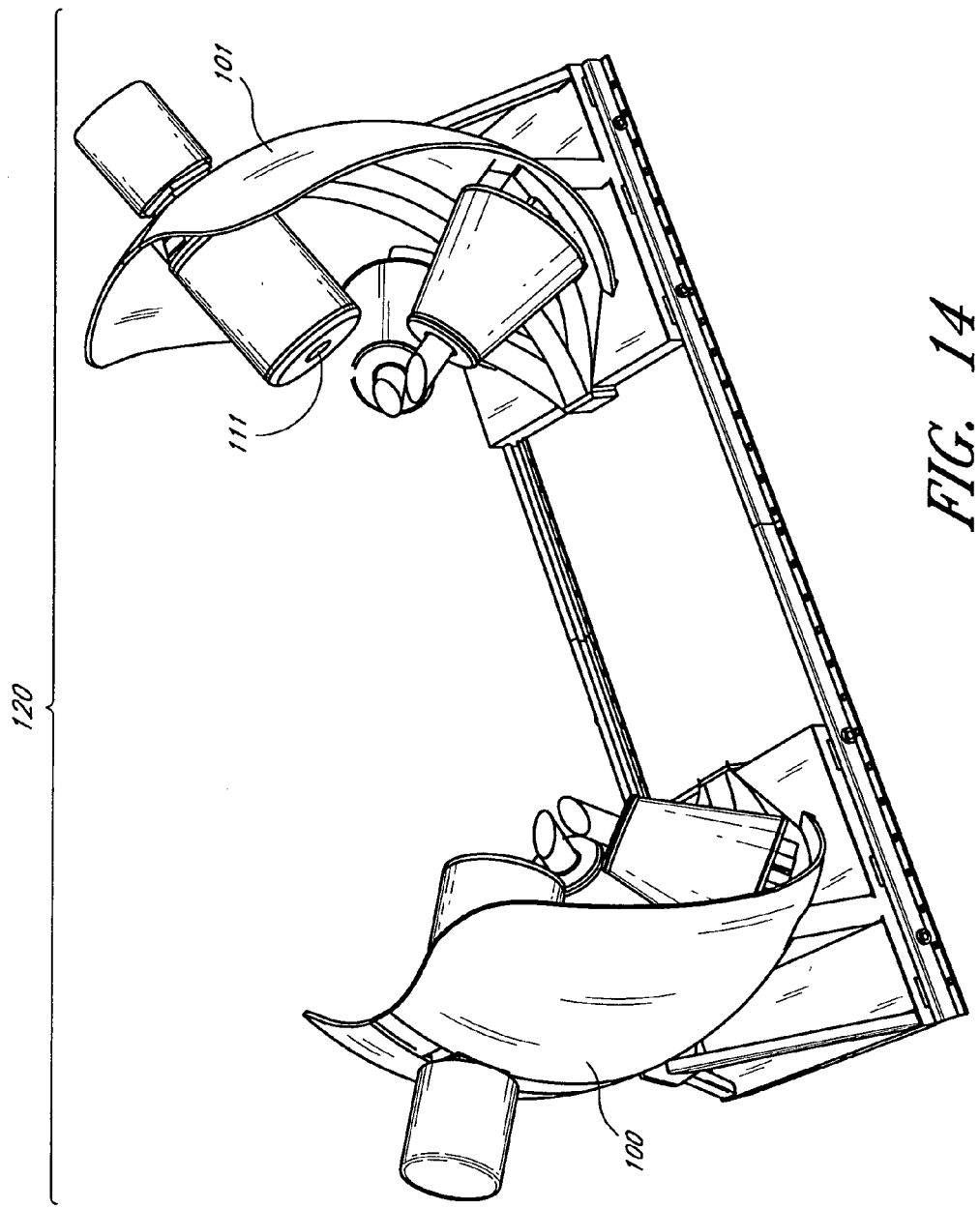
FIG. 14 is an isometric view showing the apparatus of FIG. 1 in an open mode where the left and right clusters are separated.

FIGS. 13A and 13B show the CGCI apparatus 120. The CGCI is configured so as to facilitate the use of X-Ray and/or other surgical medical equipment 502 in and around the patient during operation. The two symmetrical left 100 and right 101 electromagnetic clusters are mounted on the stainless steel guide rails 102, allowing the two sections 100 and 101 to move away from each other as shown in FIGS. 14, 14A and 15. The rails 102 are bolted to a floor or mounting pad. The cluster on the CGCI structure 120 rolls inside the rails 102, under relatively tight tolerance to prevent lateral or vertical movement during a seismic event. In one embodiment, the rails 102 are designed to withstand the forces of a Zone 4 seismic event without allowing the CGCI structure to escape containment.

A stainless steel spur toothed rail 104 is bolted to the floor or mounting pad under the CGCI structure 120. A Servo Dynamic model HJ96 C-44 brushless servomotor 128 (max 27 lb.-in torque) with its associated servomotor amplifier model 815-BL 129 are provided to move the clusters 101, 100. The motor has a reduction gearbox with a ratio of 100:1. A stainless steel spur gear attached to the reduction gear shaft meshes with the spur toothed rail 104. The propulsion system 150 is configured to exert up to 2700 lbs. of force to move the CGCI sections 100 and 101.

Two Ledex model 175 solenoids 118 are mounted in the base of the CGCI structure. The solenoid shafts extend into the c-channel rails. Normally the solenoids are de-energized and the shafts are pushed out by an internal spring 119. This ensures that in case of a power outage or equipment failure, the CGCI does not roll out of the rails because the solenoid shafts engage into the solenoid locking shaft holes automatically. When moving the CGCI sections, the solenoids 118 retract the shafts from the holes. The motor then engages and the sections 100, 101 begin to move. Once the shafts have moved away from the holes, the solenoids are de-energized and the shaft tips (e.g., ball bearing tips) roll against the inner side of the channel. When the shafts reach the next locking hole the shafts are pushed into the holes by the springs and the motor (by interlocks) is disengaged.

In one embodiment, the control of the propulsion system 150 is performed remotely at the CGCI control room.

FIG. 13 further shows the CGCI 120 assembly when the system is set in "operational mode." The two symmetrical clusters 100 and 101 are engaged as described above. FIGS. 13A and 13B show the location of the spur toothed rail 104 and the brushless servo motor 128.

FIGS. 14, 14A, 15, and 16 are isometric views of the CGCI apparatus 120 when its main two symmetric left 100 and right 101 coil clusters are in a fully open mode (non operational) and the magnetic cores are retracted.

The rear view of the symmetrical one half of the CGCI, shows the parabolic flux collector shields 105 with the C-Arm upper cylinder coil support 106.

In one embodiment, the CGCI apparatus 120 is configured to meet the structural as well as safety considerations associated with the generation of a magnetic field of 2 Tesla.

Figure 17:
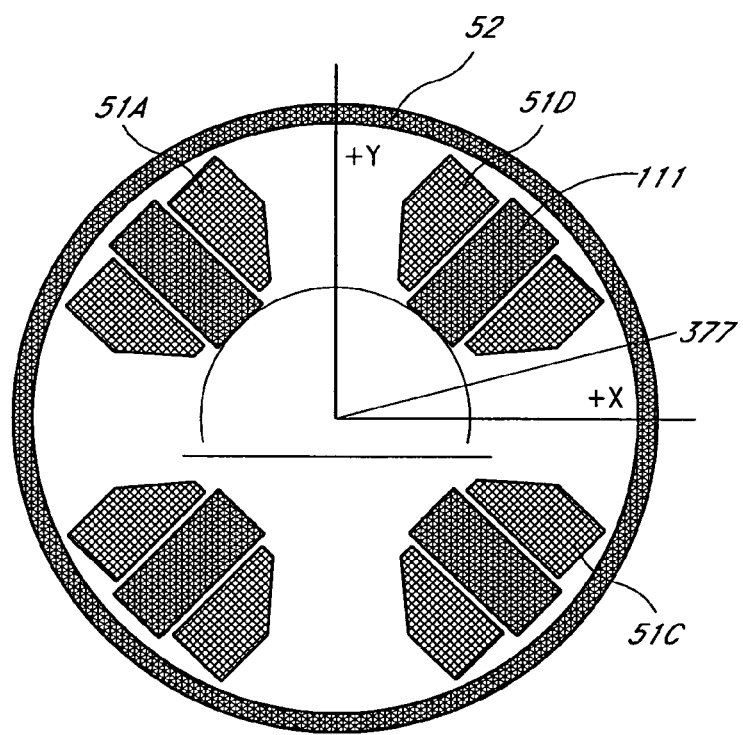
FIG. 17 shows a magnet cluster of a full-scale system.
Figure 17A:
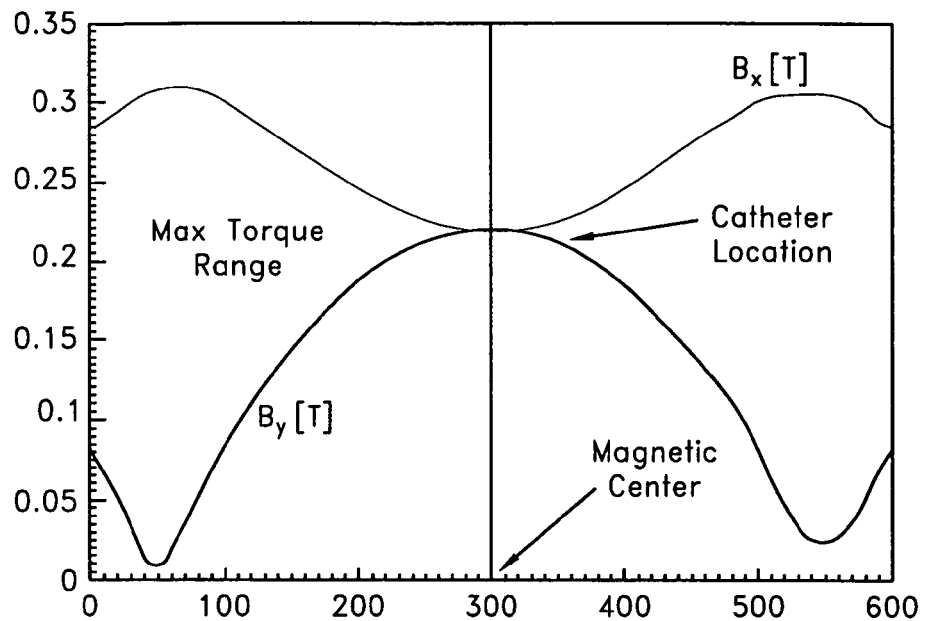
FIG. 17A is a graph of torque range of the full-scale system.
Figure 17B:
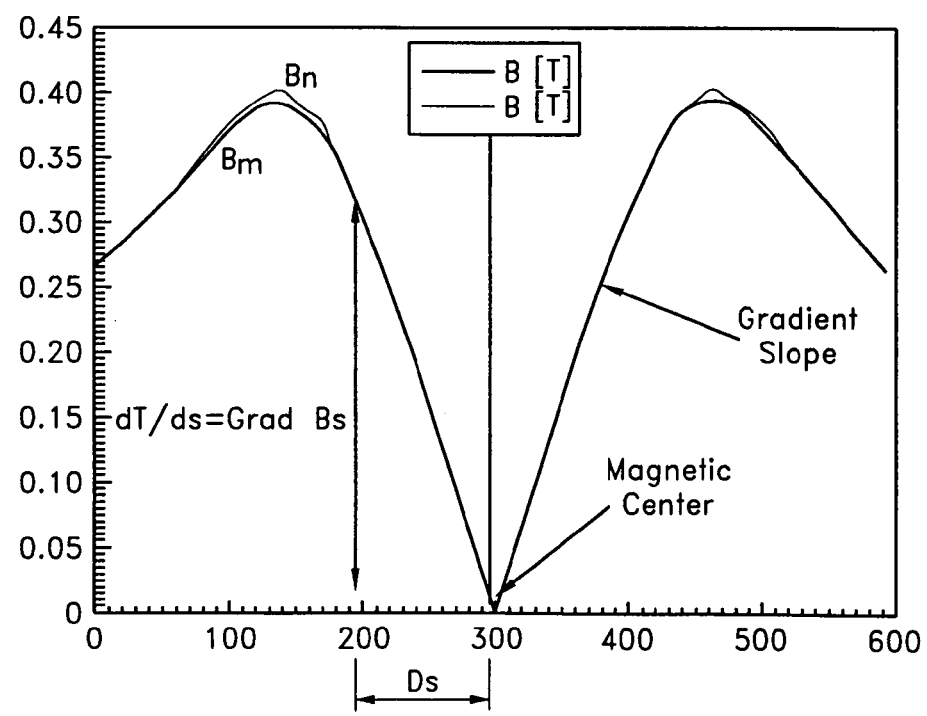
FIG. 17B is a graph of field gradients for the full-scale system.

FIGS. 17, 17A, and 17B illustrate the scaling factors and rules of interpretation of the scale model 50 and its electrical as well as mechanical characteristics, as noted in FIG. 3A. The scaling factors; AT(r), Eq(1), and PF (r), Eq(2) allow the design of coils 51A, 51B, 51C, and 51D and the core sizes for the multi-coil CGCI magnetic field generators. FIG. 17B further summarizes the magnetic force equation ($F_m$) as it is applied to a permanent magnet catheter tip 377 (in one embodiment, the catheter tip is configured as a 4 mm diameter×10 mm NdFeB35 magnet) and the field needed to push/pull the catheter tip 377 with 20-35 grams of force. The coil clusters 110, 115, and 116 of the CGCI half section 101 and its counterpart assembly 100 generate dB/ds field gradients between 1.6 T/m to 3.0 T/m. FIG. 22A shows that according to the magnetic torque equation, the desired maximum torque is 0.013 Newton meters. The 101 coil cluster and its symmetrical counterpart 100 generate a maximum magnetic field strength between B=0.04 T and 0.15 T.

Figure 18A:
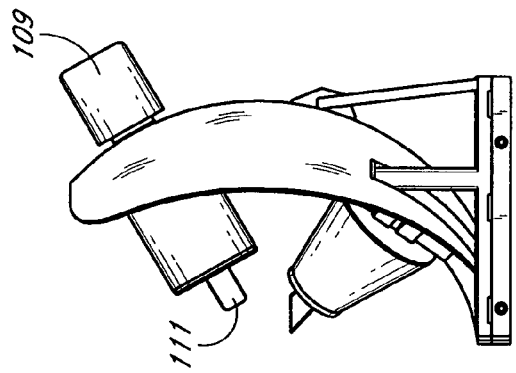
FIG. 18A is a side view of a magnet cluster of the CGCI apparatus.
Figure 18B:
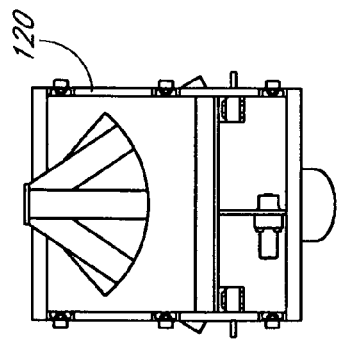
FIG. 18B is a underside view of a magnet cluster of the CGCI apparatus.
Figure 18:
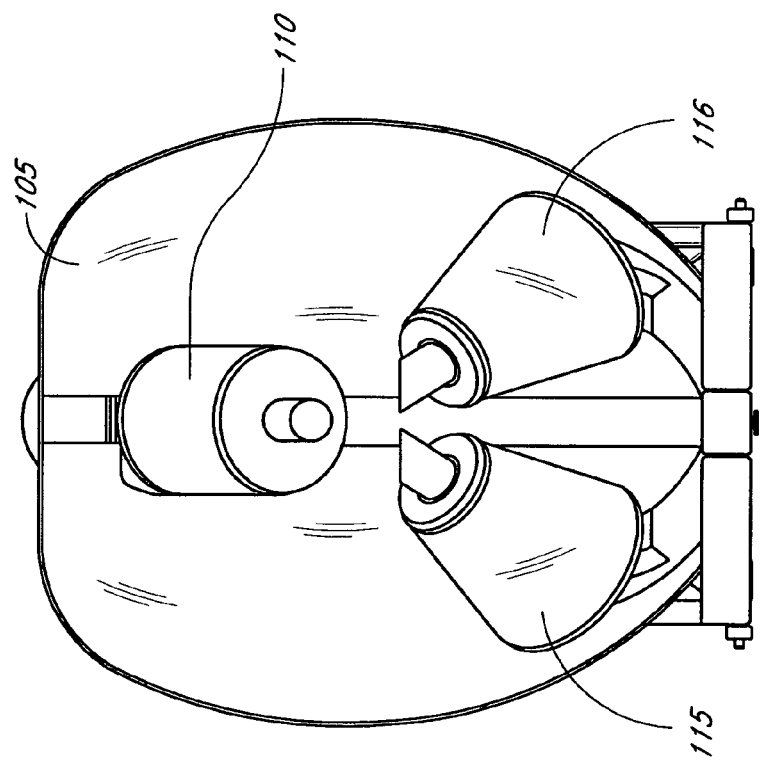
FIG. 18 is a front view of a magnet cluster of the CGCI apparatus.
Figure 21:
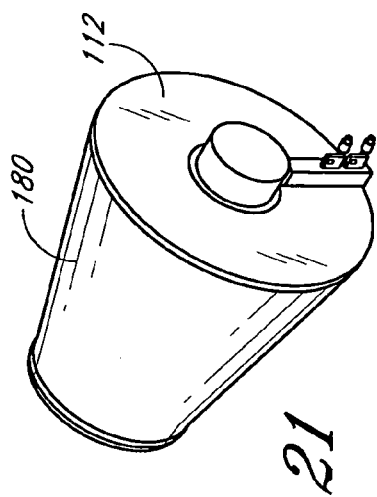
FIG. 21 is an isometric view of the tapered coil assembly.
Figure 20C:
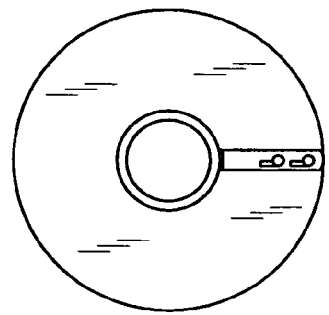
FIG. 20C is a rear view of the tapered coil assembly.
Figure 20A:
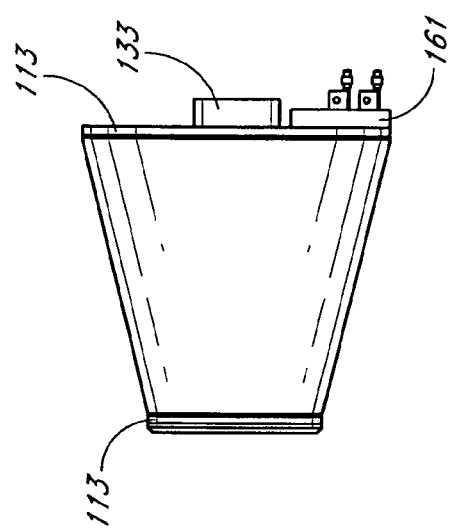
FIG. 20A is a side view of the tapered coil assembly.
Figure 20B:
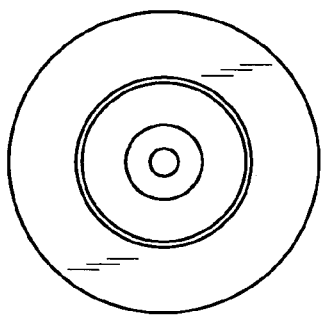
FIG. 20B is a front view of the tapered coil assembly.

FIGS. 18, 18A, and 18B are CAD-generated machine drawings showing the dimensional envelope of the CGCI apparatus 120. FIG. 18 shows the orientation of coil cluster 101 and its symmetrical counterpart 100 including angular orientation of the conical coils 115 and 116 respectively relative to the coil cylinder 110. FIG. 18A is an orthographic side view of the right coil cluster 101 describing the angular relationship between coil 115, 116, and 110.

FIG. 18B is a top view of the structural assembly and rail system of the CGCI apparatus 120.

FIGS. 19, 19A, 19B, 19C, 19D, 19E, 19F and 19G are orthographic representations of the coil assemblies 130, identified as item 110.

In one embodiment, the Coil Assemblies include two different geometry assemblies that contain the coils that generate the magnetic fields. The two base coils 115 and 116 are conical and the top coil 110 is cylindrical. Their construction is similar except the top coil assembly includes the hydraulically-activated piston 109.

In one embodiment, the coils are constructed with an inner core made of 1010 low carbon steel. The core is 134 mm in diameter and 450 mm long. Both ends are threaded to provide for attachment of the core to the base block and attaching a 0.5" thick 440 stainless steel end plate is used to hold and compress the coil.

In one embodiment, a representative coil is wound using 0.162"×1.162" hollow copper tube 123 with a 0.090 inner diameter. The tube is wrapped with 5 mil Nomex 124. The bobbin for the coil is made of Kevlar reinforced resin with a Nomex inner sheath. A total of 1487 turns are wound onto the bobbin with a layer of 20 mil Kevlar cloth placed every 4 layers of tubing. A final layer of 20 mil Kevlar is wound on the coil with Kevlar straps wound toroidally. Copper bus bars and hose fittings 161 are braised to the ends of the copper tubing. The coil is vacuum-impregnated with resin and placed in a prefabricated mold filled with resin.

In one embodiment, the core is screwed onto the mounting block 122 on arc 106. A notched 0.50" thick 440 stainless steel disk is then slid onto the core, a 0.50" thick Teflon compression disk 113 slides on top of the stainless steel plate 127. The Teflon disk helps distribute the forces of the coil onto the stainless steel plate 114. The finished coil 110 then slides on top with the Teflon disk placed on top. The end disk made of stainless steel 112 is screwed onto the core and tightened to compress the coil.

In one embodiment, the coils are water-cooled with a water flow of 0.4 gpm. Water is provided by medium pressure hoses. Three separate water lines from the three coils feed into inlet and outlet manifolds 161 located in the base structure. Cooled water is fed by an umbilical harness.

In one embodiment, the coil assemblies are designed to withstand the stresses caused by the coil's magnetic field. When the coils are energized, the magnetic forces attempt to shoot the coil off of the core. The end plates are subject to a force of up to 4500 lbs. and are designed to withstand many times this value.

FIGS. 19, 19A, 19B, 19C and 19D further show the hydraulic system 140 used in the CGCI assembly. The hydraulic system is used to position the cores to reduce the power needed for the coils of the cluster 101 and its left symmetrical counterpart 100. The core 111 of the upper cylinder coil 110 is hydraulically moved closer to the effective magnetic space of the CGCI assembly 120. The core 111 is made of two parts, a center core 111, and a hydraulically-actuated piston 142. During operation, the piston 142 can be subjected to 2200 lbs. of force, pushing and pulling on the core 111 and housing 109. The hydraulic system 140 includes the cylinder 141, a servo valve 143, and a pump 144. In one embodiment, the pump is an Eaton/Vickers vane pump model VMQ125. The pump generates an oil pressure of 1000 PSI with flow rate of 12 L/min. An Eaton Vickers model SM4-10 servo valve electronically regulates the oil flow to the cylinder. The cylinder 141 is an Eaton N5J-2 cylinder with a stainless steel shaft. The use of stainless steel or other substantially non-magnetic material (e.g., aluminum, titanium, etc.) prevents the conduction of additional magnetic fields in the vicinity of the assembly. The cylinder 141 provides a pushing force of 4900 lbs. and a pulling force of 4100 lbs. The hydraulic system 140 is shown by FIG. 19G, where the cylinder 141 is mounted on the rear of the central arc 106. The servo valve 143 and vane pump 144 are located near the CGCI base support 117.

FIGS. 20A, 20B, 20C and 21 show the construction of the coils 51A, 51B, 51C and 51D respectively.

In one embodiment, the four base coils are conical. Their construction is similar to the cylinder coils 51AT and 51DT except for the top coil assembly which has a hydraulically-activated core.

In one embodiment, the coils 180 are constructed with an inner core made of 1010 low carbon steel. The core is 134 mm in diameter 450 mm long both ends are threaded to provide a method of attaching the core to the base block and attaching a 0.5" thick 440 stainless steel end plate to hold and compress the coil.

In one embodiment, the coils are constructed of 0.162"× 1.162" hollow copper tube with a 0.090 inner diameter. The tube is wrapped with 5 mil 440 Nomex. The bobbin of the coil is made of Kevlar reinforced resin with a Nomex inner sheath. A total of 1487 turns are wound onto the bobbin with a layer of 20 mil Kevlar cloth placed every 4 layers of tubing. A final layer of 20 mil is wound on the coil with Kevlar straps wound toroidally. Copper bus bars and hose fittings are braised to the ends of the copper tubing. The coil is vacuum-impregnated with resin and heat curved. The coil is then placed in a prefabricated resist mold which is filled with pigmented epoxy and heat curved.

In one embodiment, the core is screwed onto the mounting block on arc 107 and 108. A notched 0.50" thick 440 stainless steel disk 127 is then slid onto the core. A 0.50" thick Teflon compression disk 113 slides on top of the stainless steel plate. The Teflon disk helps distribute the forces of the coil onto the stainless steel plate. The finished coil slides on top with a similar Teflon disk placed on top. The last piece is the end disk 133 made of stainless steel that is screwed onto the core and tightened to compress the coil.

In one embodiment, the coils are water cooled with a water flow of 0.4 gpm. Water is provided by medium pressure hoses that run through a hose way running along the side of the arc tube. Three separate water lines from the three coils are fed into inlet and outlet manifolds located in the base structure. Cooled water is fed by the umbilical harness.

Low resistance I/O copper welding cables attach to the coil bus bars. The cables run from the base of the structure to an isolated connector 166.

In one embodiment, the two conical coils have extension rods screwed onto their ends 112. The extensions are made of 1010 steel and their ends are cut at an angle.

In one embodiment, the coil assemblies are configured to withstand the stresses caused by the magnetic fields. The end plates 127 and 133 are subjected to a force of up to 4500 lbs. and are designed to withstand five times this value.

FIGS. 22A, 22B, 22C, 22D and 22E are isometric representations of the use of the scaling Equations (1), (2), (3), (4) and (6) as applied while expanding the scale model 2D four-coil geometry from 80 mm to the 3D full scale six-coil geometry.

The scaling Equations (1) and (2) and the magnetic force equations (5) and (6) are used in combination with coil current polarity and polarity rotation equations (8) and (9) design the magnetic circuit 400 performance.

Figure 22D:
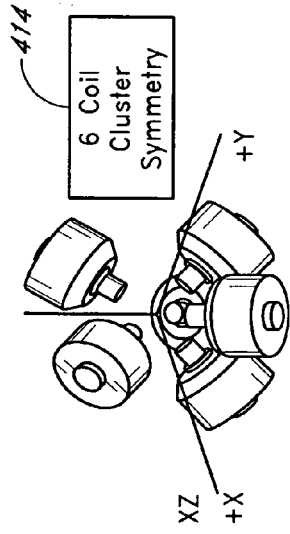
FIG. 22D shows 6 coil cluster symmetry.
Figure 22E:
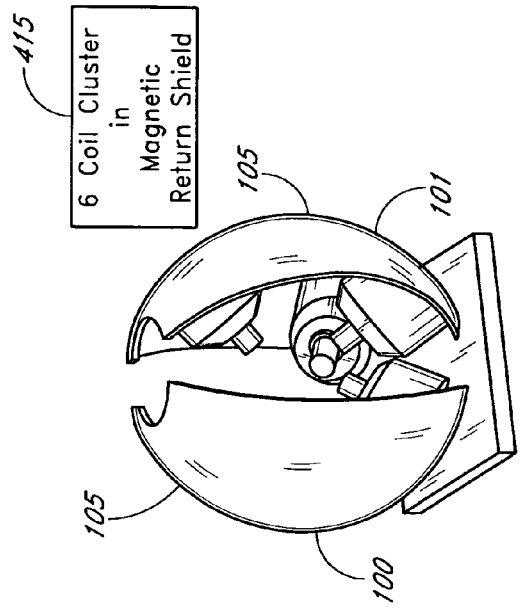
FIG. 22E shows 6 coil cluster symmetry in a magnetic shield.
Figure 22A:
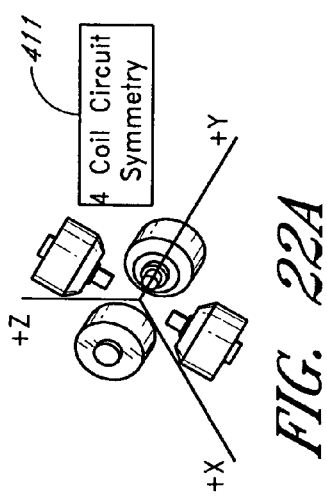
FIG. 22A shows 4 coil circular symmetry.
Figure 22B:
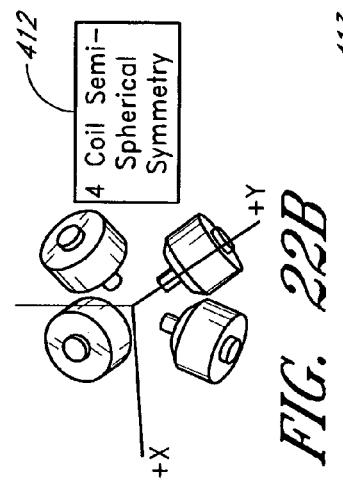
FIG. 22B shows 4 coil semi-spherical symmetry.
Figure 22C:
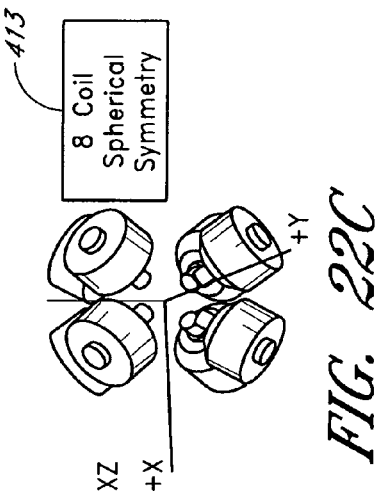
FIG. 22C shows 8 coil spherical symmetry.

FIG. 22C is an isometric representation of the first order expansion from the 2D (600 mm) scale model 50 showing a four coil cluster 411.

FIG. 22D is an isometric representation of the second order expansion of FIG. 22C to four coils rotated 45° in the +Y direction on a surface of a sphere to give a four coil semi-spherical symmetry cluster 412.

FIG. 22E is an isometric representation of the third iteration of FIG. 22C wherein the four coils shown in the cluster 412 are mirror imaged on the XY plane to produce an eight coil spherical symmetry cluster 413.

FIG. 22F is an isometric representation of the fourth iteration under the topological transformation wherein the coil structure is reduced to a six coil cluster 414.

FIG. 22G is a graphic rendition of the CGCI apparatus 120 wherein the configuration coil cluster shown in FIG. 22F is encased with parabolic flux return antennas 105 and is tilted under its transformation encasement of the six coil cluster into the YZ symmetrical magnetic return shield 415.

In one embodiment, the topological iterations from 411 through 415 under the boundary conditions set forth by the scalability Equations (1) and (2) are possible because the 2D scale model 50 space is continuous and the homeomorphism one-to-one correspondence is preserved and as defined by the Euler-Poincare characteristics for such locally equivalent space of the same dimension.

Figure 23:
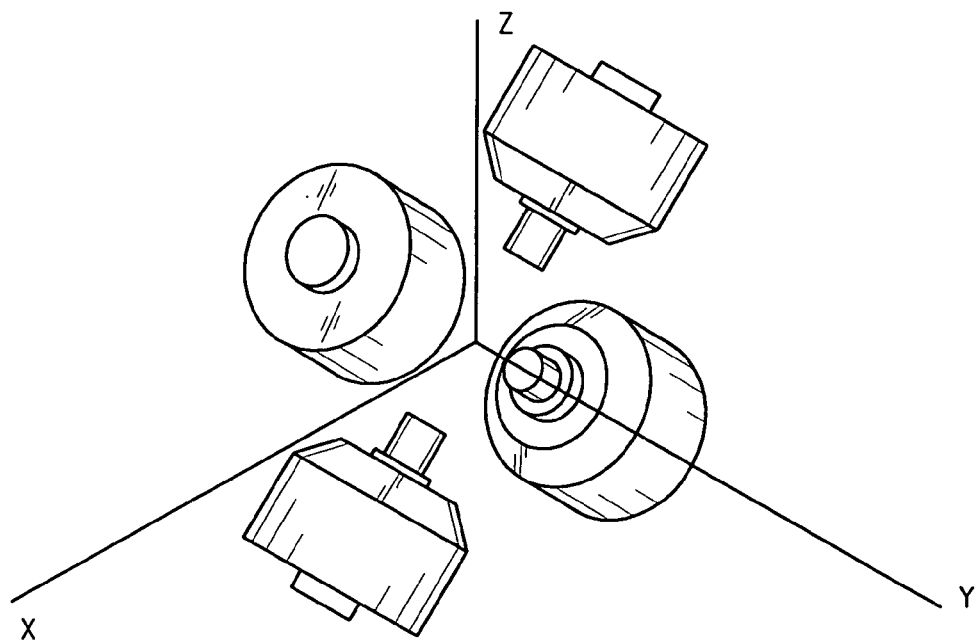
FIG. 23 shows 4 coil circular symmetry and a reference coordinate system.
Figure 24:
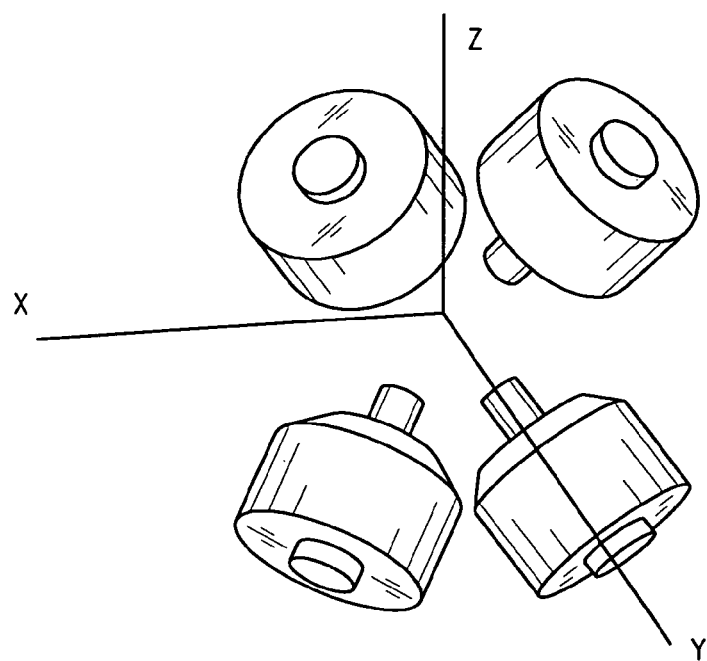
FIG. 24 shows 4 coil semi-spherical symmetry and a reference coordinate system.
Figure 23B:
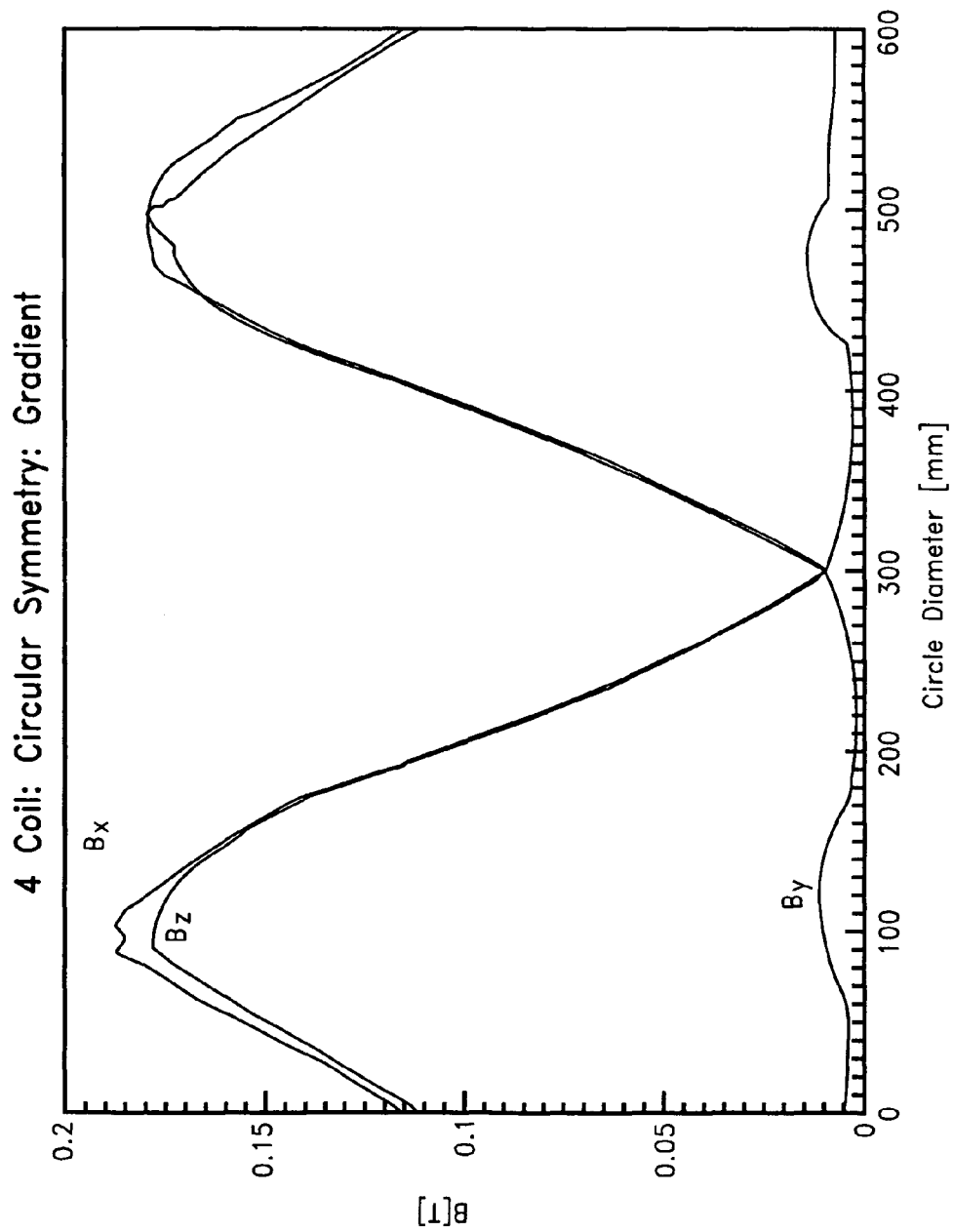
FIG. 23B shows field gradients of the 4 coil circular symmetry.
Figure 24A:
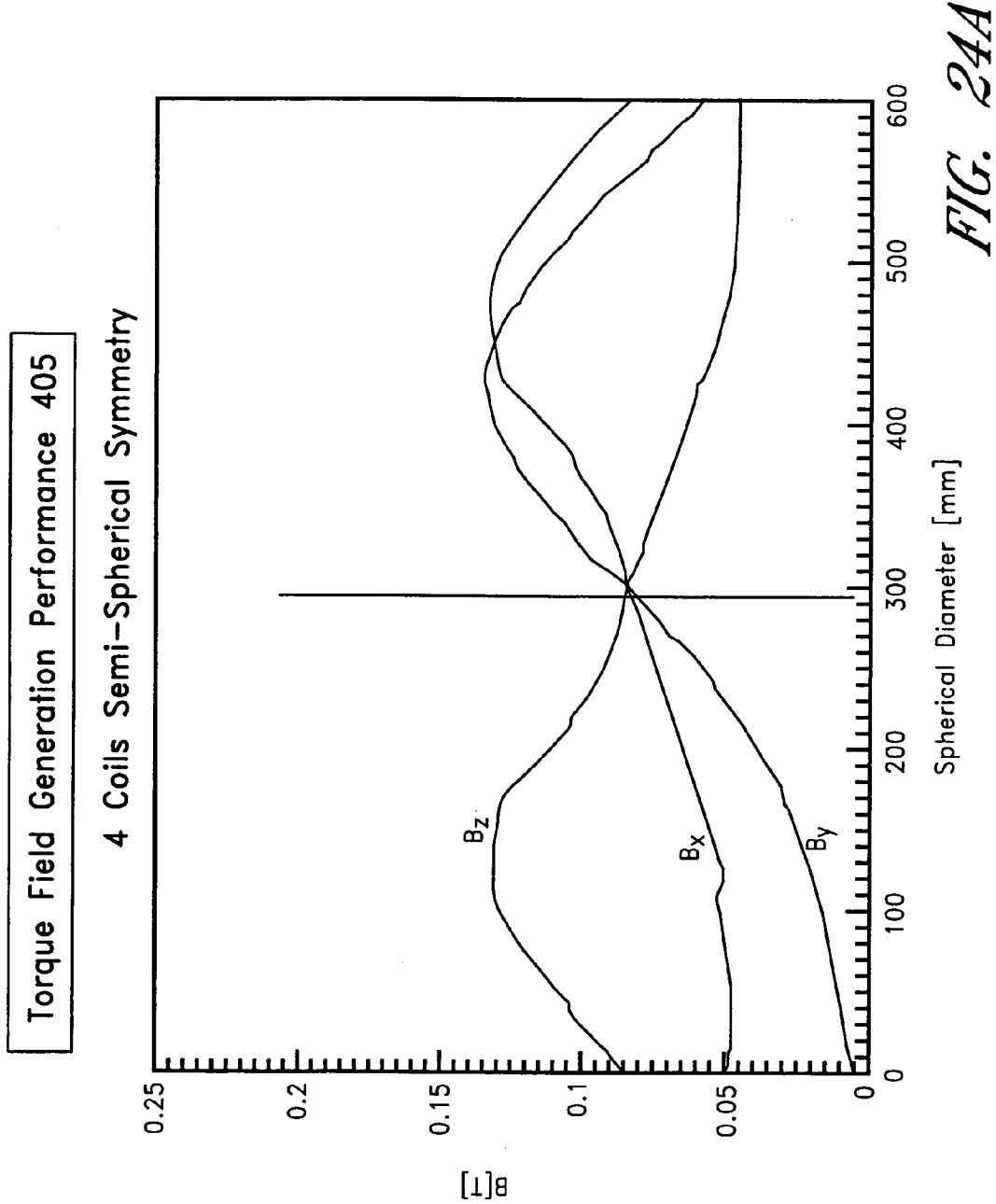
FIG. 24A shows B fields of the 4 coil semi-spherical symmetry.
Figure 24B:
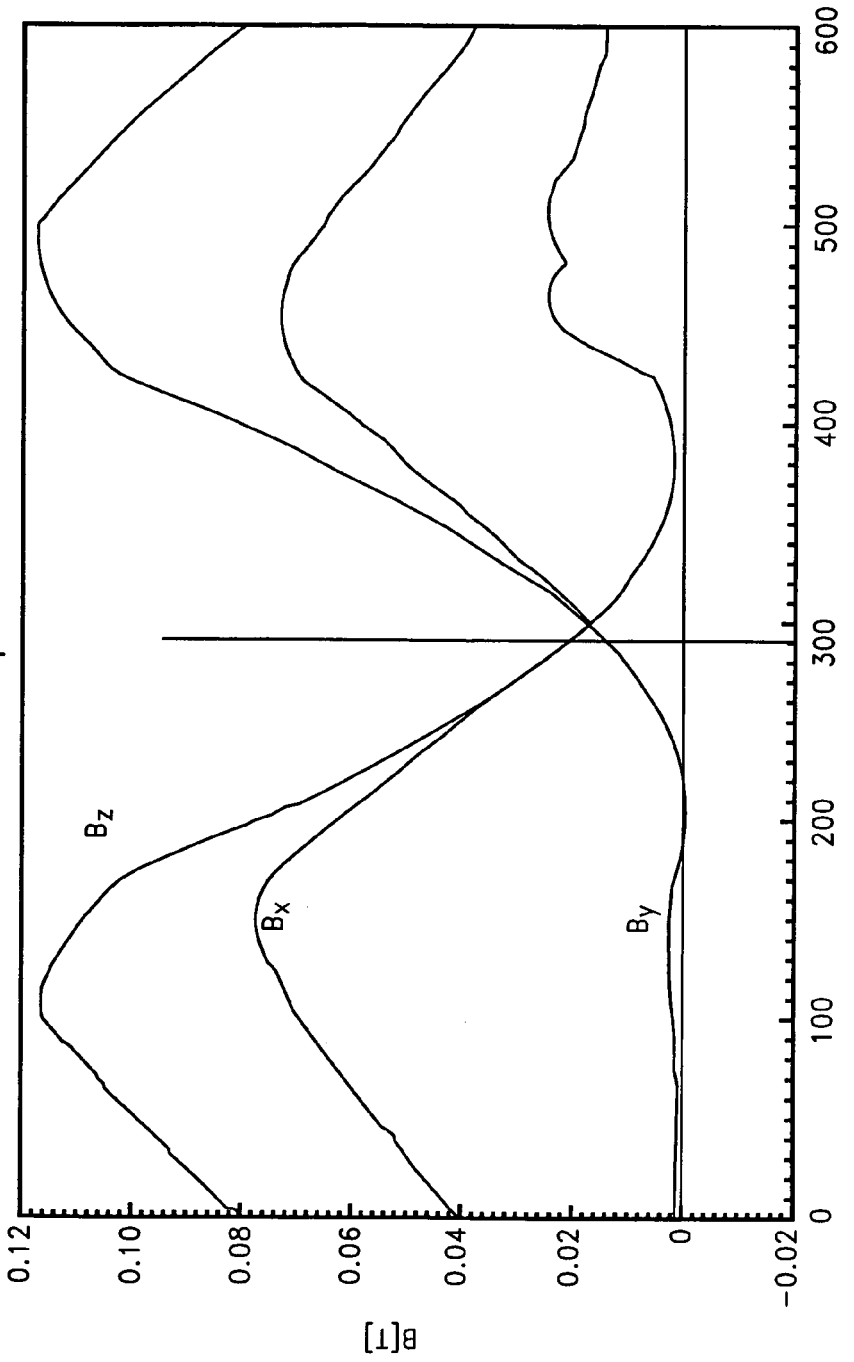
FIG. 24B shows field gradients of the 4 coil semi-spherical symmetry.

FIG. 22C and its simulation shown in FIGS. 23 and 23A shows the resultant torque field generation performance. FIGS. 23 and 23B show the gradient field performance, where the field is shown for torque $T_M$=0.12 T and where gradient for force central is $F_m$=1.20 T/m.

FIGS. 22D, 24, 24A and 24B illustrate the topological transformation from the geometry configuration of the four coil circular symmetry (FIG. 22C) to its topologically homeomorphic four coil semi-spherical symmetry cluster 412. (The transformation is a rotation of the four coils 45° in the +Y direction on the surface of the sphere generated from the 600 mm circle with the center at X, Y, Z=0). The orientation of the coils 51A, 51B, 51C and 51D are placed on a semi-circular topology. The transformation allows evaluation of the performance of the 2D model 50 relative to orientation. The resultant data from the transformation 412 is shown in FIG. 22A for torque control $T_m$=0.085 T and in FIG. 24B for gradient for force control ($F_m$)=0.85 T/m.

Figure 25:
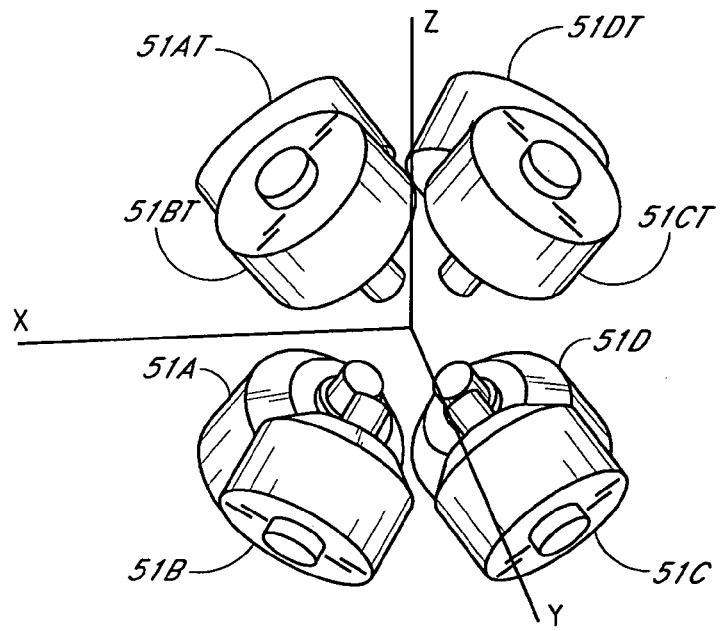
FIG. 25 shows 8 coil spherical symmetry and a reference coordinate system.

FIGS. 22E, 25, 25A and 25B show the topological transformation 413. (The transformation is an XZ plane mirror duplicate of the four coils). The four coil semi-spherical symmetry is duplicated to generate an XZ axial return path for the magnetic field. The physical configuration is shown in FIG. 22E and the field for torque control $T_m$=0.265 T is shown in FIG. 25A, where the gradient field performance $F_m$=1.65 T/m. The symmetrical arrangement of the coils does not violate the predictable magnetic relationship identified in FIGS. 2, 2A, 3, 3A and 4.

Figure 26:
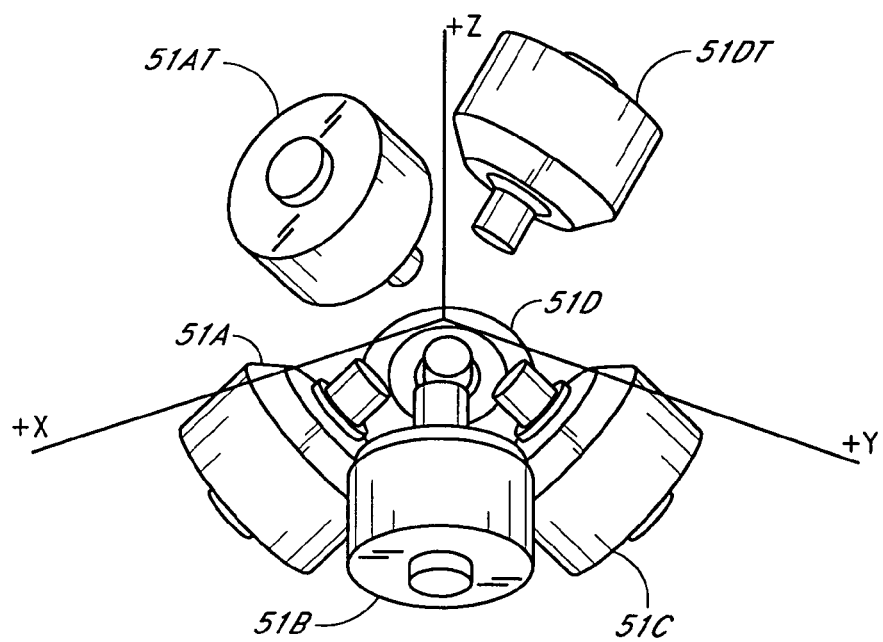
FIG. 26 shows the 6 coil cluster and a reference coordinate system.
Figure 25B:
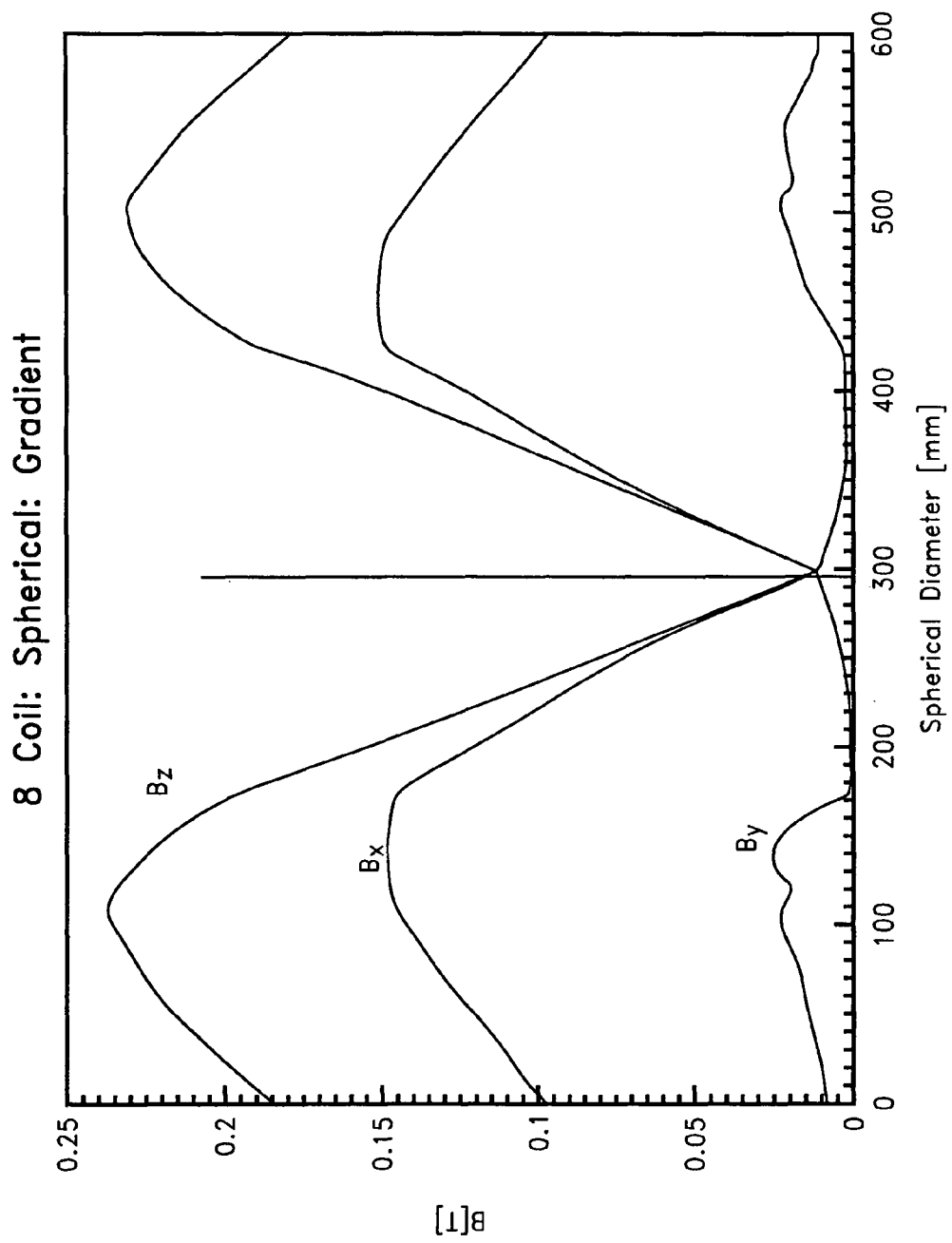
FIG. 25B shows field gradients of the 8 coil spherical symmetry.
Figure 26B:
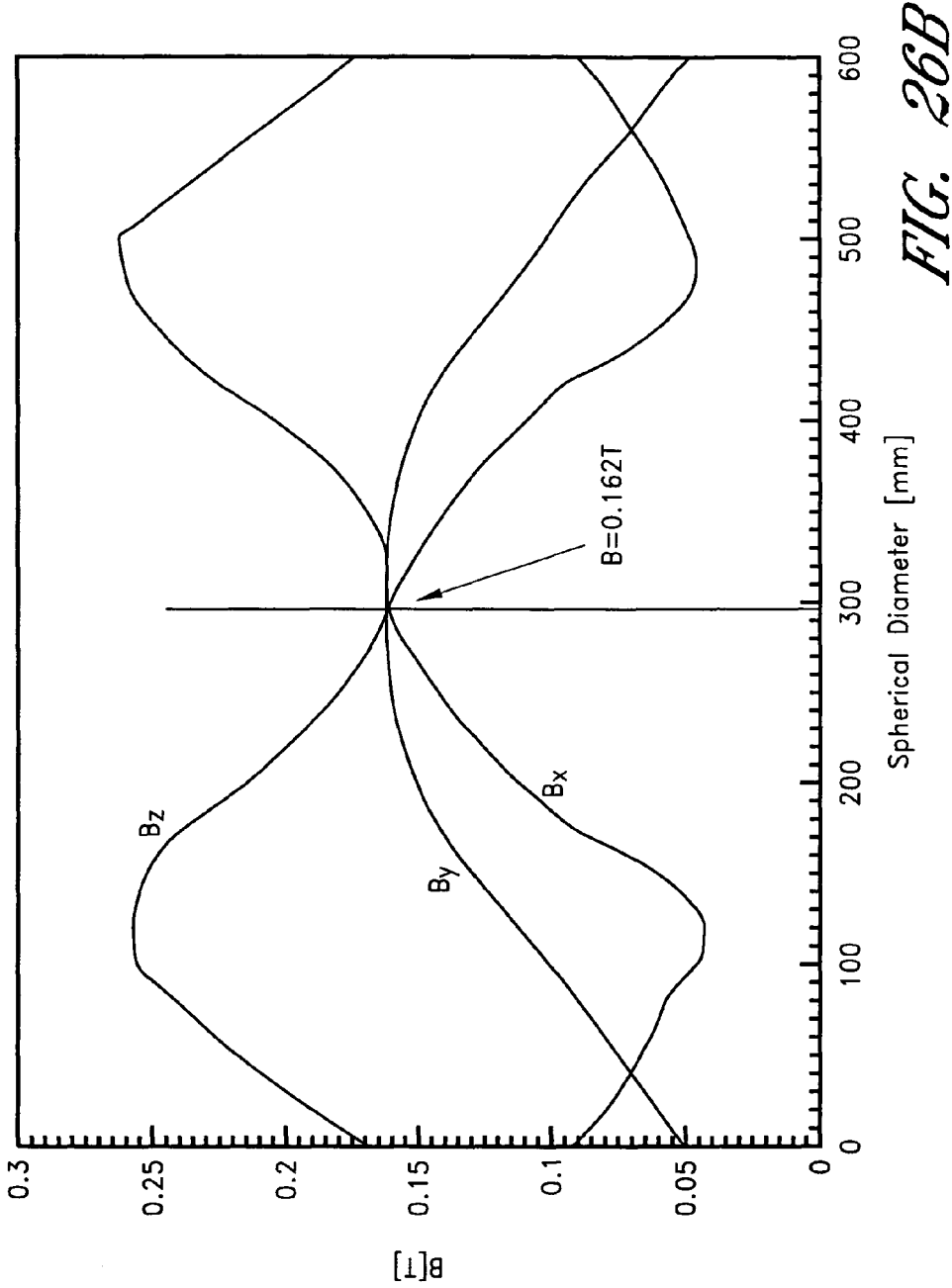
FIG. 26B shows B fields of the 6 coil cluster with double ampere-turns on the upper coils.
Figure 26C:
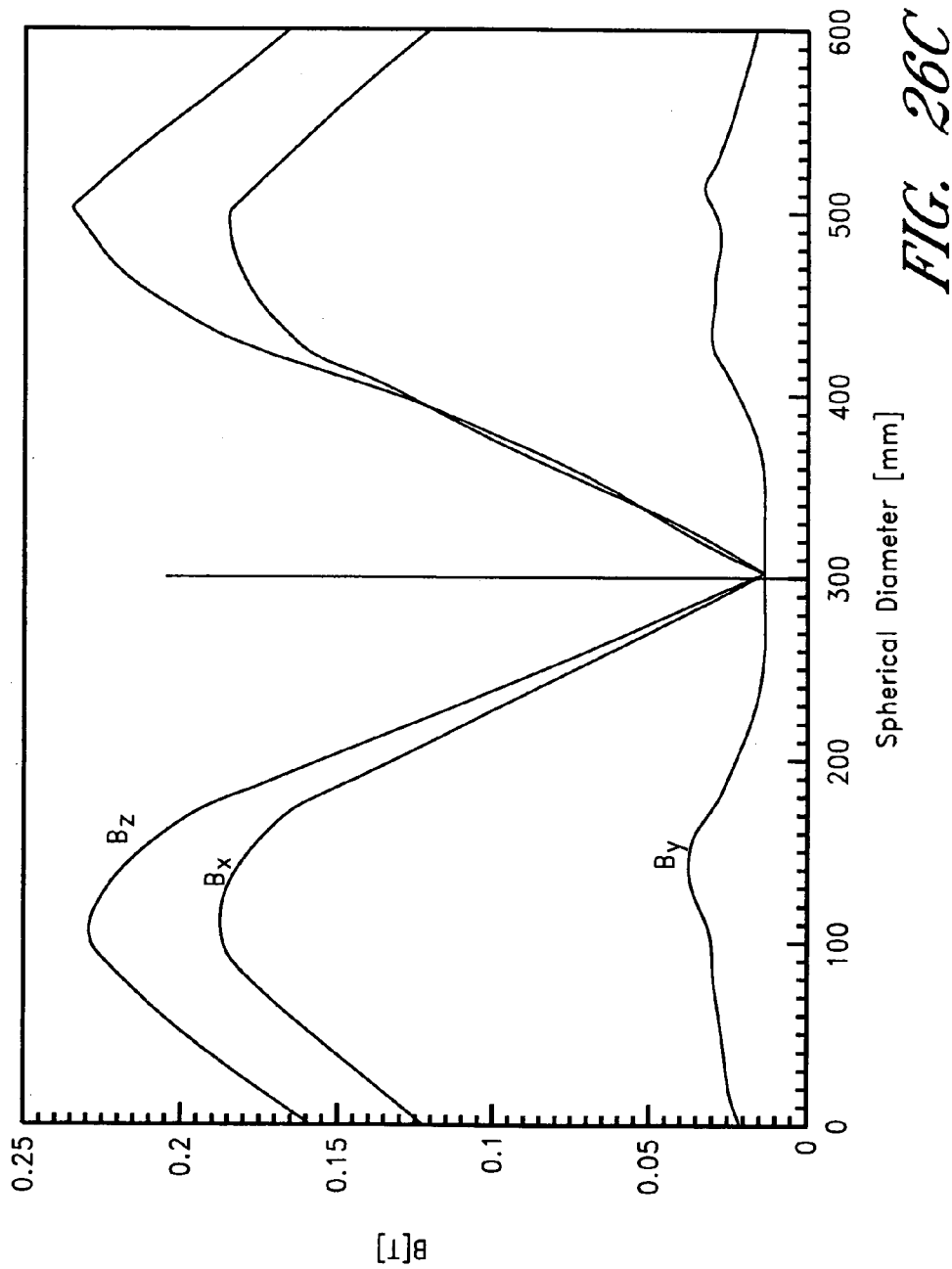
FIG. 26C shows field gradients of the 6 coil cluster.

FIGS. 22F, 26, 26A, 26B and 26C show the topology transformation 414 wherein the upper cluster top left 51AT and top right 51DT coils are rotated 45° back to the XZ plane and combined into a left and right top coil respectively. The resultant geometry is shown in FIG. 26A where the performance is measured with coils of equal Ampere-turns (AT) and found to be symmetrical where B<0.15 Tesla. The geometry is further investigated where coils 51AT and 51DT are fitted with twice as many Ampere-turns. FIG. 26B shows symmetrical performance on the centerline and B=0.162 T. The symmetrical geometry performance shown in FIG. 26B is further confirmed by FIG. 26C where the gradients are symmetrical and dB/dS=1.7 T/m.

In one embodiment, the cylindrical upper coils 51AT and 51DT are provided with twice the Ampere turns (AT) of separate lower coils so as to allow a symmetrical force and force gradient as shown.

Figure 26D:
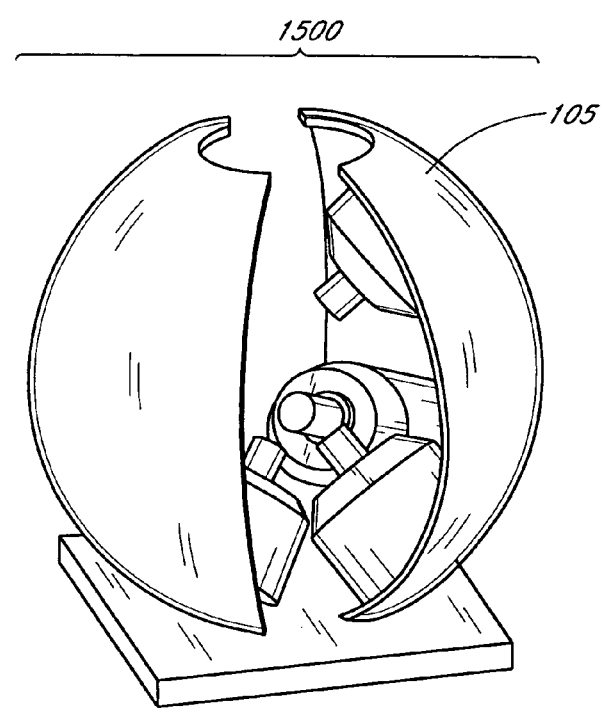
FIG. 26D shows the 6 coil cluster with a shield.
Figure 26E:
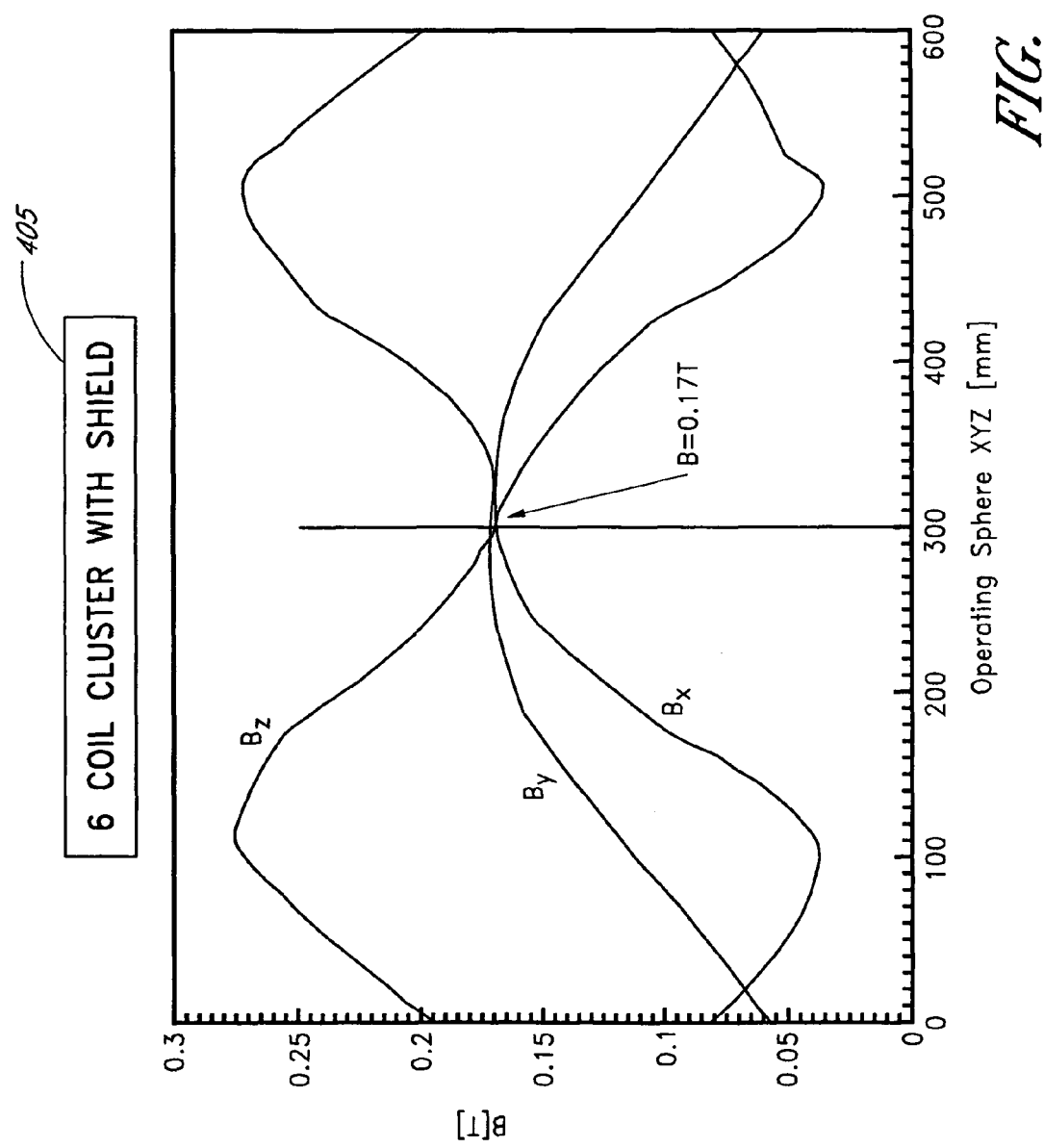
FIG. 26E shows B fields of the 6 coil cluster with the shield.
Figure 26F:
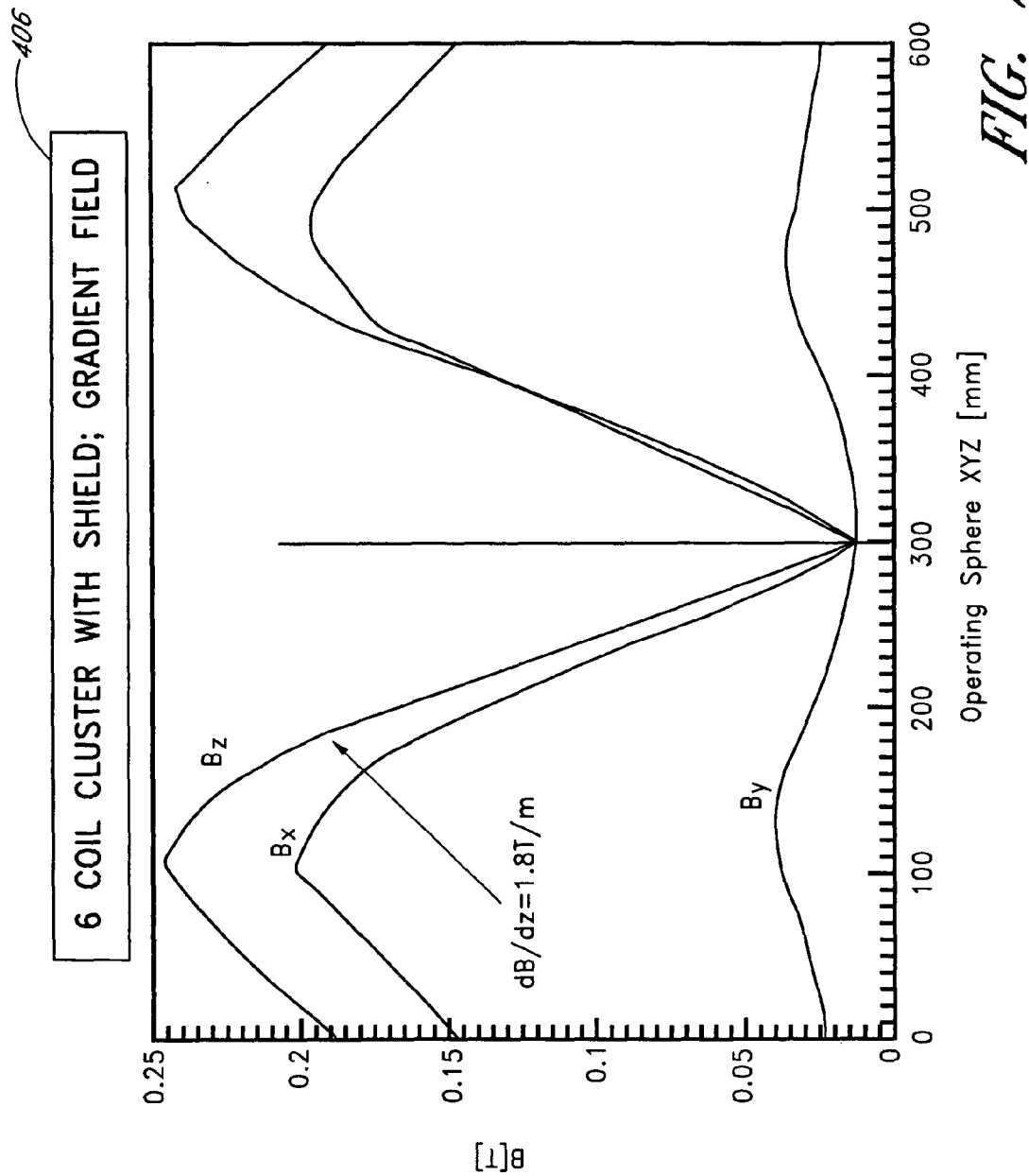
FIG. 26F shows field gradients of the 6 coil cluster with the shield.

FIGS. 26D, 26E and 26F illustrate the CGCI configuration when the coil clusters 100 and 101 are fitted with the parabolic flux return shields 105. The six-coil configuration and magnetic circuit is further enhanced by the use of such parabolic shields to collect the magnetic flux radiated above and beyond the effective boundaries. As shown in FIG. 26E, in the six coil cluster with shield 105, the magnetic B 405 field is symmetric and B=0.173 Tesla. FIG. 26F shows that in the six coil cluster configuration with shield, the gradient field mode 406 is symmetric and dB/dz=1.8 Tesla/m. The shielding produced by the parabolic antennas 105 is such that with a B field of 20 gauss to 2 Tesla, the effective perimeter magnetic field is less than 20 gauss 12" away from the CGCI apparatus 120. The effective mass of the shield 105 further improves the overall magnetic circuit and improves the magnetic circuit.

FIGS. 26G, 26H and 26I illustrate the topological transformations as they alter the maximum field strength and field gradient. The transformation from one iteration to the next assumes similar conditions as to power and coil size and evaluates the transformations relative to torque control field variations in the magnetic center. The steps of the transformation are shown in percentage where the scale model 50 is set as the base configuration shown in FIG. 3 respectively.

FIG. 22H shows measured field strength and field gradient parameters. Power optimization is a measure of efficiency. One performance benchmark is the power consumption of the CGCI apparatus 120.

The graph in FIG. 26G shows the similarity between performance of the eight coil chapter (FIG. 22E) and the six coil cluster (FIG. 22G). Each topology includes the use of retractable cores for field control.

FIG. 26H further illustrates the force control gradient variations in the ±100 mm region. The effective field around the magnetic center, over the steps of the transformation is shown in FIGS. 22I, 3A and rule 409 for coil current direction and its resultant B-field direction 408. The figure further shows the performance of the eight coil FIG. 22E and six coil FIG. 26B topologies.

Figure 27:
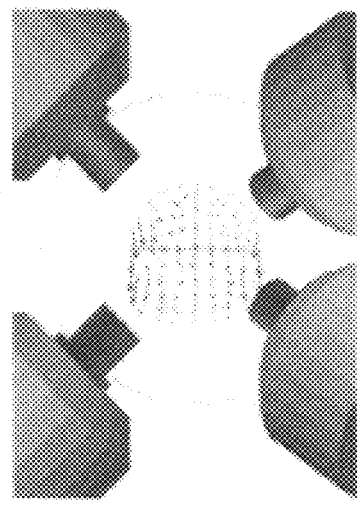
FIG. 27 shows the torque control field vector diagram on the XZ plane (B-vector).
Figure 27A:
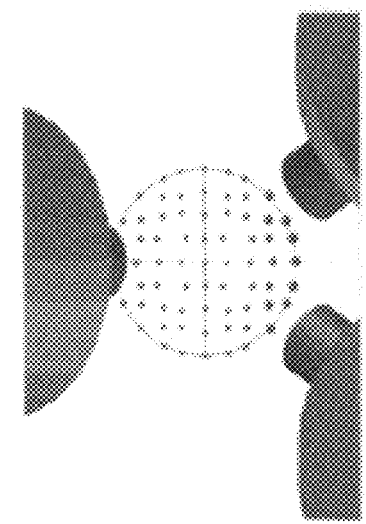
FIG. 27A shows simulation of the torque control field diagram in the YZ plane (B-vector).
Figure 27B:
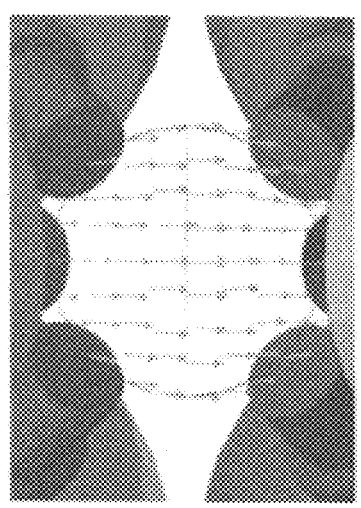
FIG. 27B shows the behavior of the B-vector in the XY plane

FIGS. 27, 27A and 27B show the common topological characteristics which allow the transformation from the 2D four coil configuration 50 to the 3D eight coil spherical configuration. The homeomorphism characteristics of the 2D 50 to 3D geometry and the four coil cluster to the eight coil cluster are expressed by the fact that various transformations of the CGCI apparatus include the following relationship:

$$B_{T_q} = B_{XY} \cos(\theta) \tag{405.1}$$

for torque control fields and $$\frac{dB}{ds} = \frac{dB_{XY}}{ds} \cdot \cos(\vartheta) \tag{406.1}$$

for force control fields, where $B_{XY}$ is the field in the XY plane, and θ is angle of spherical rotation of the coils from the XY plane.

In one embodiment, the use of the relationship shown by 405.1 and 406.1 is established by the eight coil spherical configuration. FIG. 22E demonstrates that the eight coil cluster doubles B and Grad B fields as configured to the four coil 45° semi-spherical configuration. The relationships shown by expressions 405.1 and 406.1 are further shown in the six coil cluster configuration. FIG. 26B reproduces the eight coil performance by doubling the ampere-turns of the top coils 51AT and 51DT in the XY plane.

The field strength for torque control in the magnetic center and the field gradient for force control have the following relationship for various configurations in the topological transformation steps:

$$\left|\frac{dB_s}{ds}\right| = 10 \cdot |B_{TQC}|, \text{ where } \left|\frac{dB_s}{ds}\right|$$

is the scalar absolute value of the gradient along line S and $|B_{TQC}|$ is the scalar value of the field in the magnetic center.

FIG. 27 shows the torque-control field vector diagram on the XZ plane (B-vector). FIG. 27A is a result of the simulation of the torque control field diagram on the YZ plane (B-vector). FIG. 27B shows the behavior of the B-vector on the XY plane.

Figure 28:
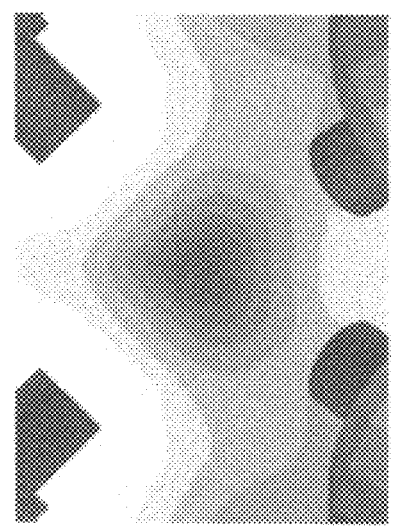
FIG. 28 shows the B-field gradient in the XZ plane.
Figure 28A:
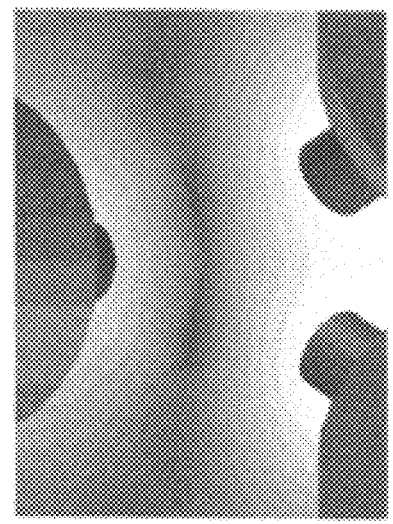
FIG. 28A shows the B-field gradient in the YZ plane.
Figure 28B:
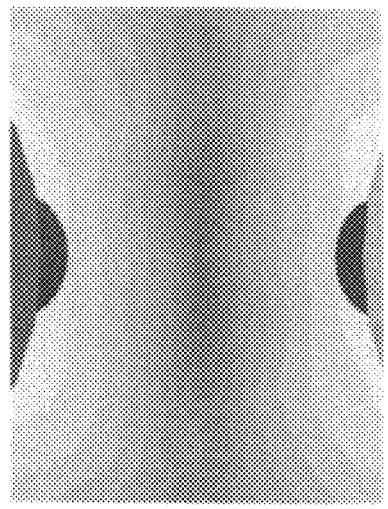
FIG. 28B shows the B-field showing gradient in the XY plane.

FIGS. 28, 28A and 28B illustrate the principles 406.2 by showing B-field showing gradient in the XZ plane. FIG. 28A further shows the B-field showing gradient in the YZ plane. FIG. 28B demonstrates the B-field showing gradient in the XY plane.

Figure 29:
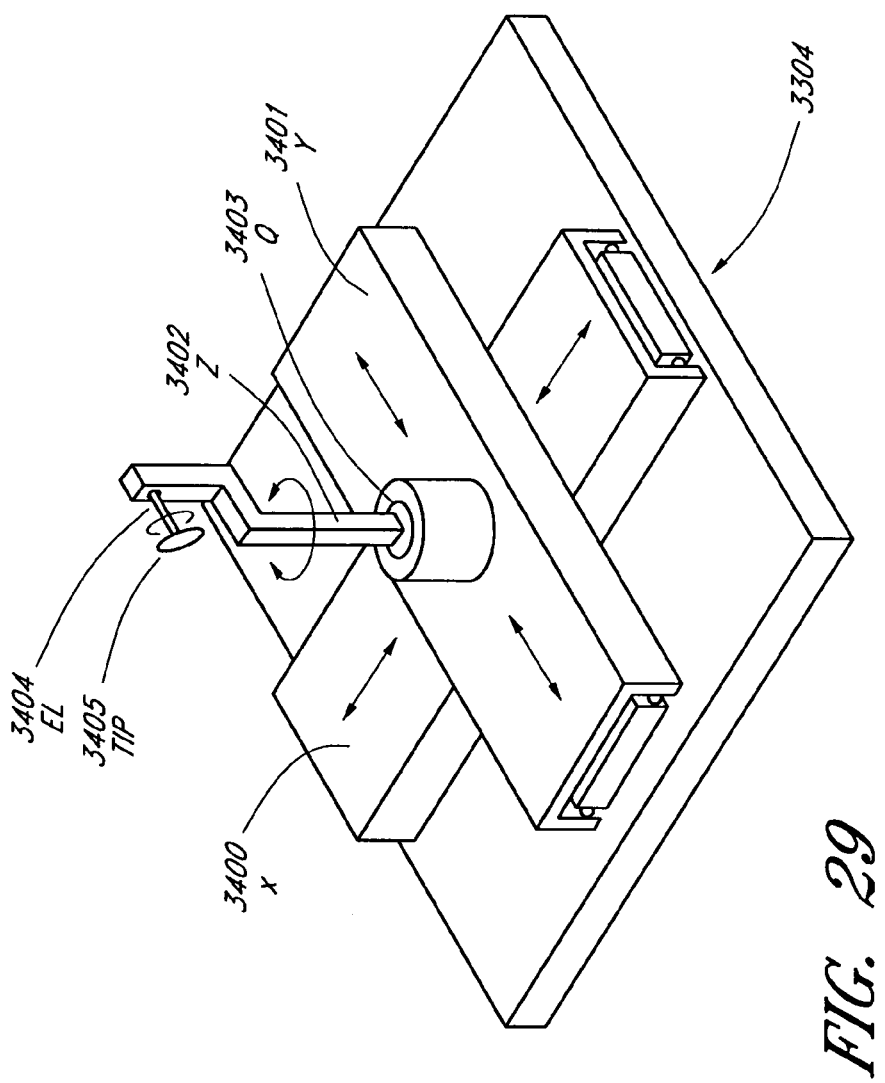
FIG. 29 is an orthographic representation of the virtual tip user input device employed by the servo closed loop control of the CGCI apparatus.

FIG. 29 is a perspective view showing one embodiment of the Virtual Tip user input device 905. The Virtual Tip 905 is a multi-axis joystick-type device that allows the surgeon to provide inputs to control the position, orientation, and rotation of the catheter tip 377.

In one embodiment, the Virtual Tip 905 includes an X input 3400, a Y input 3404, Z Input 3402, and a phi rotation input 3403 for controlling the position of the catheter tip. The Virtual Tip 905 further includes a tip rotation 3405 and a tip elevation input 3404. As described above, the surgeon manipulates the Virtual Tip 905 and the Virtual Tip 905 communicates the surgeon's movements to the controller 501. The controller 501 then generates currents in the coils to effect motion of actual catheter tip 377 to cause actual catheter tip 377 to follow the motions of the Virtual Tip 905. In one embodiment, the Virtual Tip 905 includes various motors and/or actuators (e.g., permanent-magnet motors/actuators, stepper motors, linear motors, piezoelectric motors, linear actuators, etc.) to provide force feedback to the operator to provide tactile indications that the catheter tip 377 has encountered an obstruction of obstacle.

Figure 30:
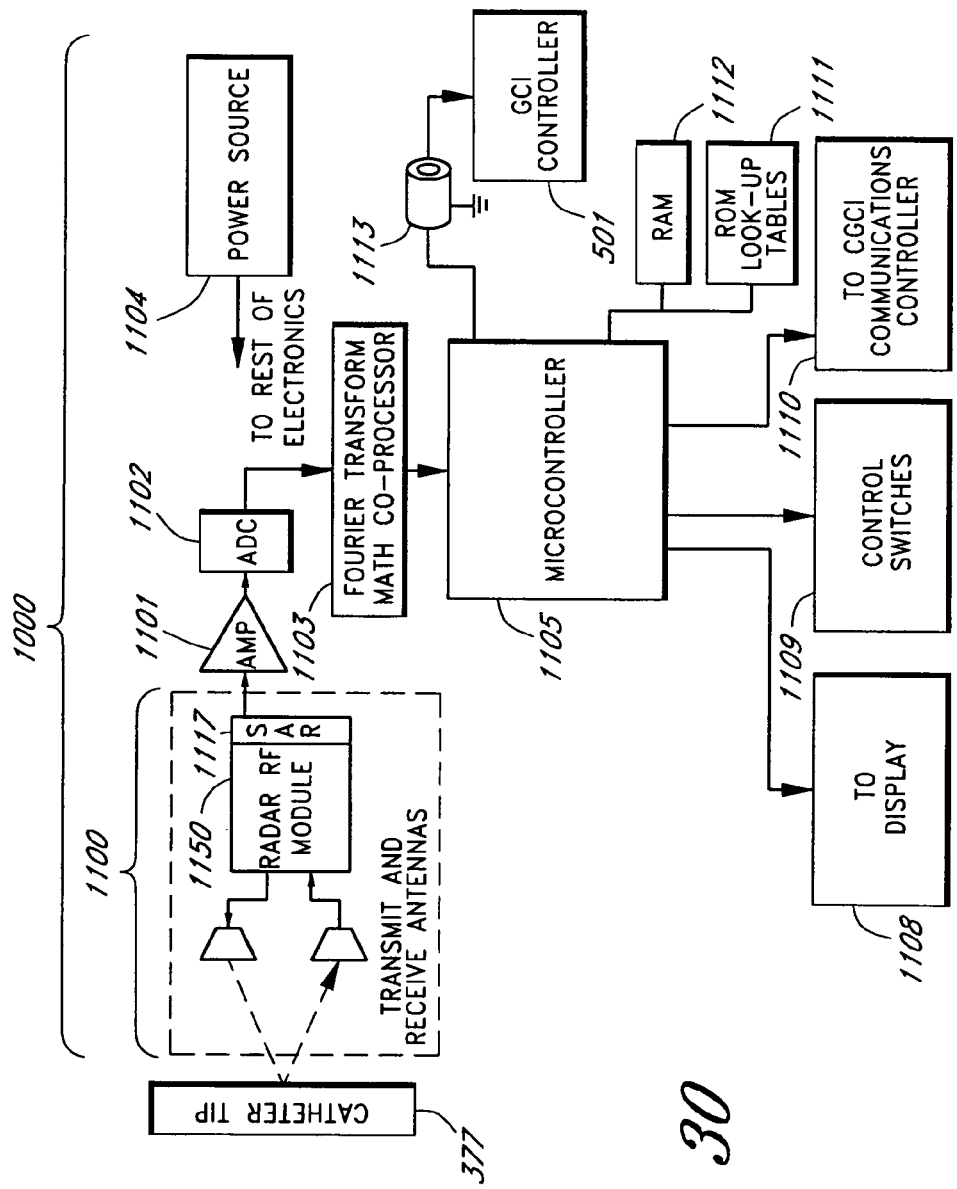
FIG. 30 is a block diagram of the radar used in capturing the position of the catheter tip and fiduciary markers.

FIG. 30 is a block diagram of a radar system 1000. The radar 1000 shown in FIG. 30 includes a phased-array radar module 1100 having transmit/receive antenna elements and a Radio Frequency (RF) module 1150. The radar system 1000 includes an amplifier 1101, an A/D converter 1102, a Fast Fourier Transform module 1103, and a microcontroller 1105. The apparatus further includes a memory module in the form of RAM 1112, and a look-up table in the form of a ROM 1111. One embodiment includes a voice messaging and alarm module 1110, a set of control switches 1109, and a display 1108. The data generated by the radar system 1000 is provided to the CGCI apparatus 501 via communications port 1113.

In one embodiment, the radar system 1000 includes a phased-array and uses Microwave Imaging via Space-Time (MIST) beam-forming for detecting the catheter tip 377. An antenna, or an array of antennas, is brought relatively near the body of the patient and an ultra wideband (UWB) signal is transmitted sequentially from each antenna. The reflected backscattered signals that are received as radar echoes are passed through a space-time beam-former of the radar unit which is designed to image the energy of the backscattered signal as a function of location. The beam-former spatially focuses the backscattered signals so as to discriminate it from the background clutter and noise while compensating for frequency-dependent propagation effects. The contrast between the dielectric properties of normal tissue and the catheter tip 377 (formed out of a ferrite such as samarium-cobalt SmCo5, or neodymium-iron-boron, NdFeB, etc.), in the regions of interest produces sufficient backscatter energy levels in the image to distinguish normal tissue from the catheter tip 377, affording detection and discern ability. A data-adaptive algorithm is used in removing artifacts in the received signal due to backscatter from the body tissue interface (e.g., the skin layer). One or more look-up tables containing the known dielectric constants of the catheter tip contrasted against the background dielectric information relative to the biological tissue can be used to identify features in the radar image.

In one embodiment, the physical basis for microwave detection of the catheter tip 377 in the biological tissue is based on the contrast in the dielectric properties of body tissue versus the signature of the catheter tip 377. The contrast of the dielectric values of biological tissue versus that of the catheter tip is amplified, filtered and measured.

A typical summary of dielectric properties in living tissues for medical imaging in the range of 10 Hz to 20 GHz and parametric models for the dielectric spectrum of tissues are given up by C. Gabriel et al., "The dielectric properties of biological tissues: II. Measurements in the frequency range 10 Hz to 20 GHz" Phys. Biol., vol. 41, 1996 a, p 2251-69, which yields an (ε') of 5-60 and electrical conductivity (σ) of 0.065-1.6 Simens/m (S/m) the relative complex permittivity, $\epsilon_r$, of a material is:

$$\epsilon_r = \epsilon' + j\epsilon''$$

$$\epsilon' = \epsilon/\epsilon_0$$

$$\epsilon'' = \sigma/\epsilon_0 \omega$$

Where $\epsilon$ is the permittivity, $\epsilon_0$ is the permittivity of free space=8.854e-12 Farads/m, $\epsilon''$ is the relative dielectric loss factor and $\omega$ is angular frequency. Combining the above expression with a look-up table for material dielectric properties yields the data distinguishing between the magnetic tip 377 and tissue.

In one embodiment, the radar 1000 return waveform is provided to a computer using a software such as MATLAB. A target such as the catheter tip 377 is sampled with a transmitted pulse of approximately 100 ps in duration containing frequencies from 400 Hz to 5 GHz with a range of approximately 1 meter in air (the range of the electromagnetic coil location). The radar emits a pulse every 250 ms (4 MHz). The return signals are sampled and integrated together to form the return waveform as measured on circuit 1000. A specific window of data of the radar interaction with the target 377 is obtained and a Fast Fourier Transform (FFT) of the window of data is taken to produce the frequency response of the target $$X(k) = \sum_{j=1}^{N} x(j) W_N^{(j-1)(k-1)}$$

and by taking a Fast Fourier Transform (FFT) 1103 we are able to identify the differences between received radar waveform, such as metal 377 or human tissues. This process uses the look-up table residing in the ROM 1111 of the system. The synthetic aperture radar 1117 (SAR) aid in the signal processing, thus, making the antenna seem like it is bigger than it really is, hence allowing more data to be collected from the area to be imaged.

In one embodiment, synthetic aperture processing is using two modalities, radar processing method as noted above or time domain focusing technique, wherein propagation distance is computed by 959.

$$d = 2\sqrt{(x)^2 + (z)^2}$$

and alternatively a propagation time computed by 960.

$$t = \frac{2\sqrt{(x)^2 + (z)^2}}{v}$$

Hence, target identification and matching is performed by characterizing the target waveform of the catheter tip 377 into a vector. The dot product is taken from the identification vector and the data, wherein, perfectly aligned data and ID results in a dot product of 1, and data perpendicular to the ID results in a dot product equal to zero. The radar controller 1105 converts the results to percent match (dielectric value, conductivity measure) of the data of the identification vector.

The catheter tip 377 has a microwave scattering cross-section that is different relative to biological tissue of comparable size, relative to their dielectric properties, which is indicated by greatly different backscatter energy registered by the receiver, and processed so as to afford a pictorial representation on a monitor 325 with a significant contrast between the two mediums. The pictorial view of the catheter tip 377 generated by the radar system 1000 can be superimposed over the X-ray fluoroscopy image and its coordinate data set linked to the CGCI controller 501 for use as a position coordinate by the servo feedback loop. Hence, microwave imaging via space-time (MIST) beam-forming is used for detecting backscattered energy from the catheter tip 377 while the background is biological tissue.

In one embodiment, the radar system 1000 detects the presence and location of various microwave scatters, such as the catheter tip 377, embedded in biological tissue. The space-time beam-former assumes that each antenna in an array transmits a low-power ultra-wideband (UWB) signal into the biological tissue. The UWB signal can be generated physically as a time-domain impulse 960 or synthetically by using a swept frequency input. In one embodiment, the radar system 1000 uses a beam-former that focuses the backscattered signals of the catheter tip 377 so as to discriminate against clutter caused by the heterogeneity of normal tissue and noise while compensating for frequency dependent propagation effects. The space-time beam-former achieves this spatial focus by first time-shifting the received signals to align the returns from the targeted location. One embodiment of the phased-array radar 1000 forms a band of finite-impulse response (FIR) filters such as relatively high dielectric doping in antenna cavity, forming the reference signal, where the doping is relative to the device of interest. The signals from antenna channels are summed to produce the beam-former output. A technique such as weights in the FIR filters can be used with a "least-squares fitting" technique, such as Savitzky-Golay Smoothing Filter, (as explained, for example, in Numerical Recipes, The Art of Scientific Computing, by W. H. Press, B. P. Flannery, S. A. Teukolsky and W. T. Vettrling, Cambridge, University Press, 1992, Chapter 14.8) to provide enhancement of the received signal and to compute its energy as a function of the dielectric properties versus the scattered background noise of body tissue, thereby providing a synthetic representation of such a signal. The system can distinguish differences in energy reflected by biological tissues and the catheter tip 377 and display such energy differences as a function of location and co-ordinates relative to the fiduciary markers 700Ax through 700Bx, thereby providing an image proportional to the backscattered signal strength, which is further used by the CGCI controller 501 in computing the position co-ordinates and orientation of the catheter tip 377 relative to the stereotactic framing of the fiduciary markers. The details of the formation of the coordinate settings of the catheter tip 377 relative to the stereotactic frame and the synchronization of such image with the fluoroscopy frame 702 is further described. In one embodiment, the radar module 1000 uses an FFT algorithm 1103 which uses a filtering technique residing in look-up tables 1111 to allow the radar 1000 sensor to discern various of dielectric properties of specific objects, such as a guidewire 379 and/or a catheter 310 with piezoelectric ring 311 and 312.

Figure 30B:
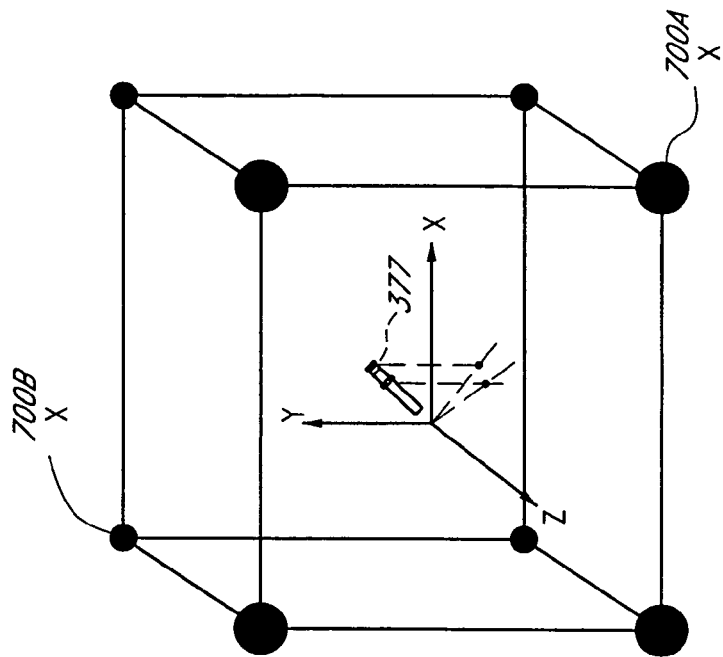
FIG. 30B is a graphic depiction of the radar forming a stereotactic frame of reference for the use in synchronizing the image such as x-ray and radar data combined with the EKG feed.
Figure 30A:
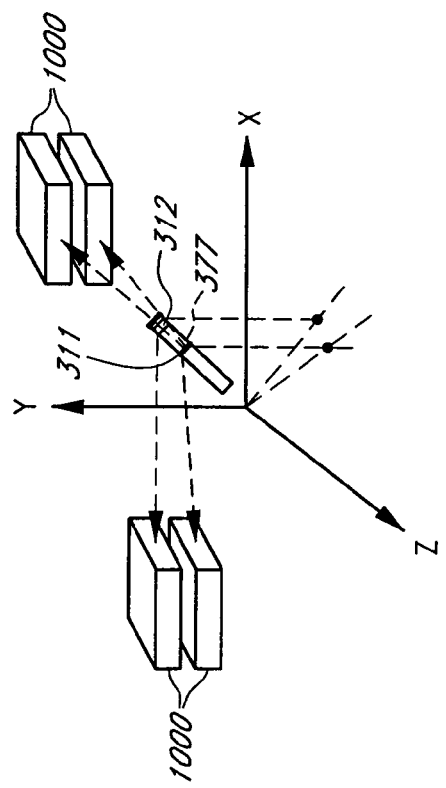
FIG. 30A is a graphical representation of the methodology used in capturing the catheter tip while using a piezoelectric ring.

FIG. 30A is a graphical representation of the catheter tip 377 embedded with one or two piezoelectric rings 311 and 312 such as Lead-Zirconate-Titanate (PZT) and/or molecularly conjugated polymers such as switchable diodes (polyacetylene). The second harmonics generated by the rings 311 and 312 provide an identifiable return signature in the second harmonic due to the non-linearity of the material. While the fundamental harmonic (e.g., 5 MHz) is transmitted by the radar, the second harmonic (e.g., 10 MHz) is distinguishable by the radar system 1000. The radar system 1000 can discern between the catheter tip (which is formed out of ferrite such as samarium-cobalt SmCo5, or neodymium-iron-boron, NdFeB, etc.) and the PZT rings 311 and 312. The ability to distinguish between the signal return from the catheter tip 377 and the PZT rings 311 and 312, allows the radar system 1000 to filter out the background clutter received from the body tissue and recognize the position and orientation of the rings 311 and 312 and the position coordinates of the catheter tip 377. The technique of using two different dielectric properties and electrical characteristics of the tip 377 versus the PZT rings 311 and 312 provides the catheter tip 377 with a radar signature that is unique and readily recognized by the radar system 1000.

FIG. 30B further shows how the radar system 1000 with its transmit and receive antennas is used to detect the position coordinates and orientation of catheter tip 377 relative to its two PZT rings 311 and 312. A geometrical manipulation is employed by the radar system 1000 and its associated FFT filter 1103 by the resident microcontroller 1105. As shown in FIG. 2D, a catheter-like device is provided with a magnetically-responsive tip 377. In one embodiment, the tip 377 includes a permanent magnet. The polarity of the permanent magnet is marked by two PZT rings where the north pole is indicated by a PZT ring 312 and the distal end of the ferrite where the semi-flexible section 310 of the catheter 376 is marked with additional PZT ring 311, also marking the south pole of the ferrite.

In one embodiment, the radar system 1000 transmits a burst of energy that illuminates the ferrite catheter tip 377. The return signal from the catheter tip 377 is received by the radar and its position is registered by observing the time of flight of the energy, thereby determining the location of the catheter tip 377 as position coordinates in a three-dimensional space. By employing the two PZT rings 311 and 312, the radar detector 1000 is also configured to discerning the location of the tip 377 relative to the two PZT rings so as to afford a measurement of PZT ring 312 relative to the second piezoelectric ring 311 with reference to the position coordinates of the catheter tip 377. The radar detector 1000 can discern the return signal from PZT rings 311 and 312 due to the non-linear characteristic of PZT material that generates a second harmonic relative to the incident wave. By comparing the strength of the fundamental frequency and the second harmonic, the radar system 1000 is able to discern the position and orientation of the two PZT rings relative to the ferrite 377, thereby providing position and orientation of the catheter tip 377.

FIG. 30B shows the technique of measuring the position and orientation of the catheter tip by the use of the radar detector 1000 and using fiduciary markers 700AX and 700BX to form a frame of reference for the catheter relative to the frame of reference of the markers. As shown in FIGS. 30B and 30F, the fiduciary markers 700AX and 700BC form a manifold 701. The locations of the markers 700AX and 700BZ are measured by the radar system 1000.

In one embodiment, the markers are electrically passive and can be made from a polymer or PZT material that allows the radar antenna to receive an RF signal return which is discernable by its harmonic structure. Criteria such as the conductivity of the body affects how much the radar signal is attenuated for a given depth (i.e., the relatively higher the conductivity the relatively higher the loss for a constant depth). An average conductivity of 1 S/m at 1 GHz signal will penetrate the human body approximately 1.8 cm.

In one embodiment, the dielectric constant of most targets will be ~1. The relative permittivity of the targets is typically of several orders of magnitude lower than that of the surrounding tissue. The conductivity of the metals is typically several orders of magnitude greater than that of the surrounding tissue. For example, the permittivity of nylon is 2-3 orders of magnitude less than that of the surrounding tissue (within a bandwidth of 1 MHz-1 GHz).

Hence, the dielectric properties as well as the conductivity measure of the target catheter tip 377 and/or its directional markers PZT rings 311 and 312 allow the radar 1000 to discern the target out of the surrounding clutter (e.g., body tissue 390) and perform the task of position definition 377 within the referential frame of fiduciary markers 700AX and 700BX.

In one embodiment, the return waveform is recorded for a static (clutter) environment, and then a target is inserted into the environment and once the clutter is subtracted from the return waveform the radar 1000 processes a target response (clutter is a general term referring to anything the radar interact with that is not a desired target).

FIGS. 30C and 30D show an image captured by monitor 325. The cineoangiographic image 702 of an arterial tree is shown with a reconstructed radar signature of the catheter tip 377. The image 702 contains a numerical grid defined and calculated by the radar 1000 and data set of coordinate or vector representation of catheter position (actual position AP) is displayed. Data on catheter position is fed to the controller 501 for the purpose of closing the loop of the servo control systems of the CGCI apparatus 1500. An illustration of the catheter tip 377 is shown in FIG. 30A, wherein monitor 325 displays the stereotactic frame formed by the fiduciary markers 700AX and 700BX obtained from the radar signature 1000. The catheter tip 377 is shown as a cube formed by the fiduciary markers 700AX and 700BX. The position data relative to the coordinates is used to form a dynamic manifold 704. The manifold 704 allows synchronization of the catheter tip position (AP) relative to the stereotactic frame 701. The process of synchronization is gated in the time domain with aid of an EKG electrocardiogram 502, where an internal clock of the controller 501 is synchronized with the EKG QRS complex so as to provide a Wiggers' diagram. The synchronization allows the CGCI controller 501 to gate the dimensional data and coordinate set of fiduciary markers so as to move in unison with the beating heart.

Synchronization of the image of the catheter tip 377 or guidewire 379, captured by the radar system 1000, is superimposed onto the fiduciary markers which are represented digitally and are linked dynamically with the image 702. This is done to create a combined manifold 701, which is superimposed onto the fluoroscopic image 702. The combined manifold moves in unison with area of interest relative to the anatomy in question. For example, the beating heart, the pulmonary expansion and contraction, and/or spasm of the patient are dynamically captured and linked together so as to achieve a substantial motion in unison between the catheter's tip and the body organs.

Synchronization 701 of the catheter tip 377 with its referential markers 700AX and 700BX, dynamically calibrate the relative position allows the CGCI 1500 to capture the data set-manifold 704 on the time domain of the patient 390 EKG signal. This allows the CGCI controller 501 to display and control the movement of the catheter tip 377 in unison with the beating heart or other body movements. Synchronization to close the servo loop modality is also used by the controller 501.

The CGCI controller can perform the data synchronization without active use of x-ray imagery since catheter position (AP) 377 data is provided independently by the radar signal 1000. In one embodiment, the radar data is used to close the servo loop.

Figure 30E:
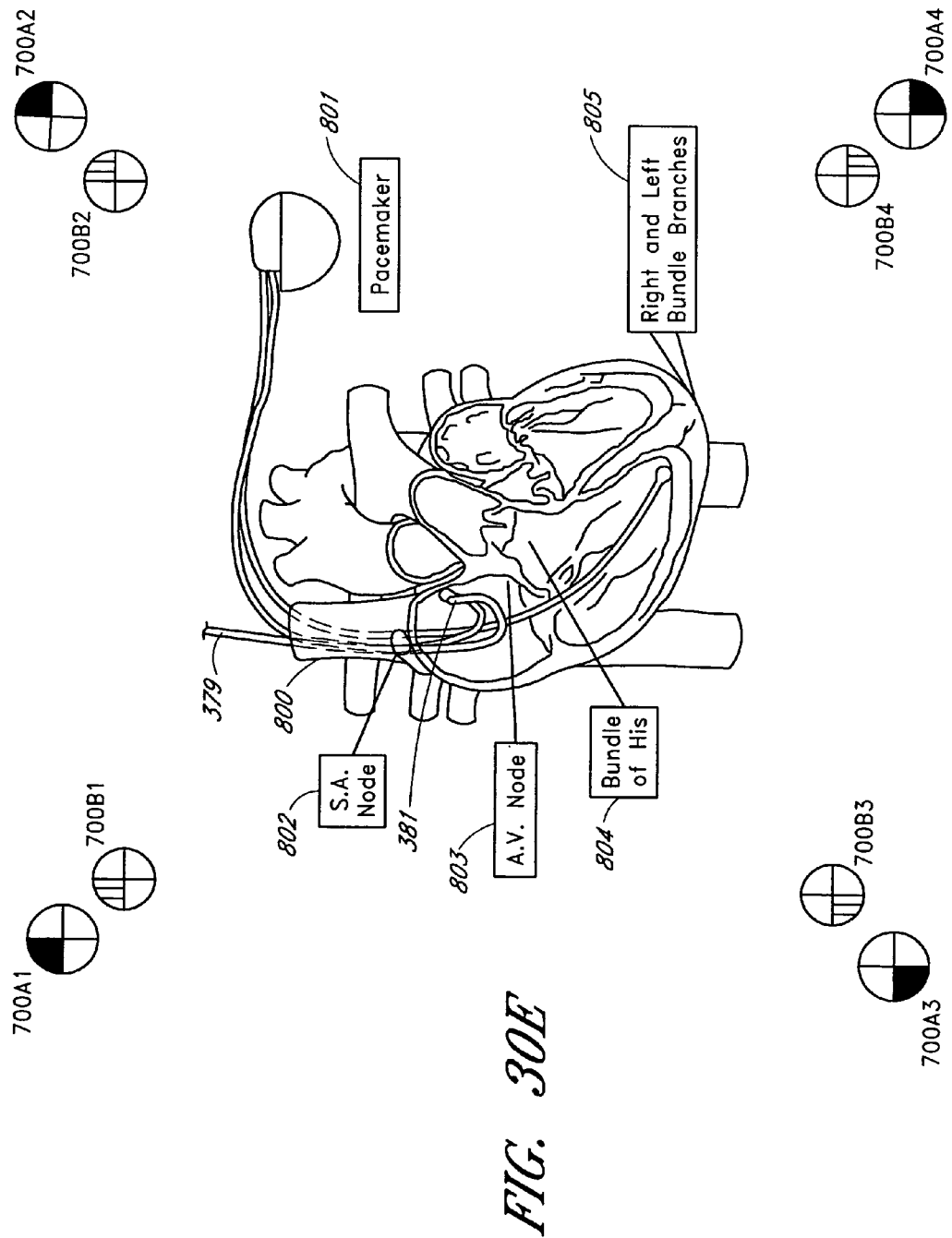
FIG. 30E shows use of a radar and fiduciary markers while performing an electrophysiological procedure.

FIG. 30E shows the use of the apparatus described in FIGS. 30C and 30D while performing a pacemaker electrode implantation. FIG. 30B further shows the implantation of cardiac pacemaker 801 with electrodes as shown, placed in an area relative to the S.A. Node 802, A.V. Node 803, and the bundle of HIS 804. Further illustrated are the right and left bundle branches 805. This procedure is performed by the implantation of a small electrode in the heart cavity wall (ventricle or atrium). The other end of the electrode is attached to an electronic device 801 which is implanted under the chest skin and which generates stimulation pulses to simulate the heart rhythm. Similar devices apply electrical shock when life-threatening heart electrical disturbances are detected by the electrodes. These electrodes are typically placed through a vein by pushing and manipulating under fluoroscopy. Through the use of the CGCI apparatus 1500, the guidewire 379 fitted with a magnetic tip 381 is used to carry and place the electrodes of the pacemaker 801 in their proper position. With the fiduciary markers 700A and 700B in place, the physician navigates the guidewire 379 through the heart lumen while having a continuous dynamic referential frame identifying the guidewire tip 381 using the position data from radar 1000 as shown in FIG. 30C and further illustrated by FIG. 30D. Often the manipulation to place the electrodes in the proper position is difficult and the results are sub-optimal due to anatomical variations. The use of the controller 501 simplifies the operation allowing the physician to place the electrodes of pacemaker 801 in desired anatomical positions. The CGCI apparatus allows the procedure to be performed accurately, with minimal exposure to ionizing radiation.

FIGS. 31, 31A and 31B show one embodiment of the CGCI 1500, where the CGCI six coil magnetic configuration is used to explain the control algorithm. The system controller 501 of the six coil magnetic configuration 400 uses a matrix of coil combinations, bipolar coil current settings 409, and piston 111 movement control. Torque control 406 is used to push and pull the tip 377 around its axis. Force control is used to push and pull the tip 377 along a path and to provide a controlled mix of torque and force for negotiating curved paths in arteries. FIG. 30 show the bottom four coils 51A, 51B, 51C and 51D and the top two coils 51AT and 51DT. The coil current polarity is defined by facing the coil pole 402 from the center region with the patient's perspective with the patient positioned along the Y axis. Polarity is positive for clockwise (CW) current flow on the "left side" for coil 51AT, 51B and 51A. Polarity is positive on the "right side" for coils 51DT, 51C and 51D in the counter clockwise (CCW) current direction (see FIG. 4 for combination settings).

Each of the coils 51A, 51B, 51C, 51D, 51AT and 51DT are separately fed and controlled from a bipolar power source 526. The power source is controlled from a central six channel regulator 525 assisted by the computer 527 containing the matrix algorithm 528 for the three modes 405 (Torque), 406 (Force), and sloped 417, 418 (L) noted above.

In one embodiment, the "man-in-loop" control is a joystick (JS) 900 and its virtual tip 905. In one embodiment, a "fire" thumb button serves as a selection between force and torque modes. The movement of the stick forward, left, back and right rotates the catheter tip 377 (using torque mode) around its axis in these directions. When the push-button is pressed, the catheter tip 377 is moved forward, left, right and back (force control). When the JS 900 "fire" push-button is not pressed, the computer 527 uses the torque matrix 528 tables (see FIG. 4) available to the regulator 527.

In one embodiment, the example below expresses a simple matrix used for regulating a full catheter 377 rotation. The matrix locks the possible current polarity combinations and sequences for the six coils for torque fields. Selection of the valid combination for the location and direction of the tip 377 is set when the joystick 900 is moved by the operator. The torque field 405 begins to rotate while the JS 900 is pressed. When the JS 900 is released, the field is held constant. A "right click" on the JS 900 button drops the field to zero. Similar matrix selections and coil current regulation setups are available for JS 900 force control 406.

Figures 31C, 31D:
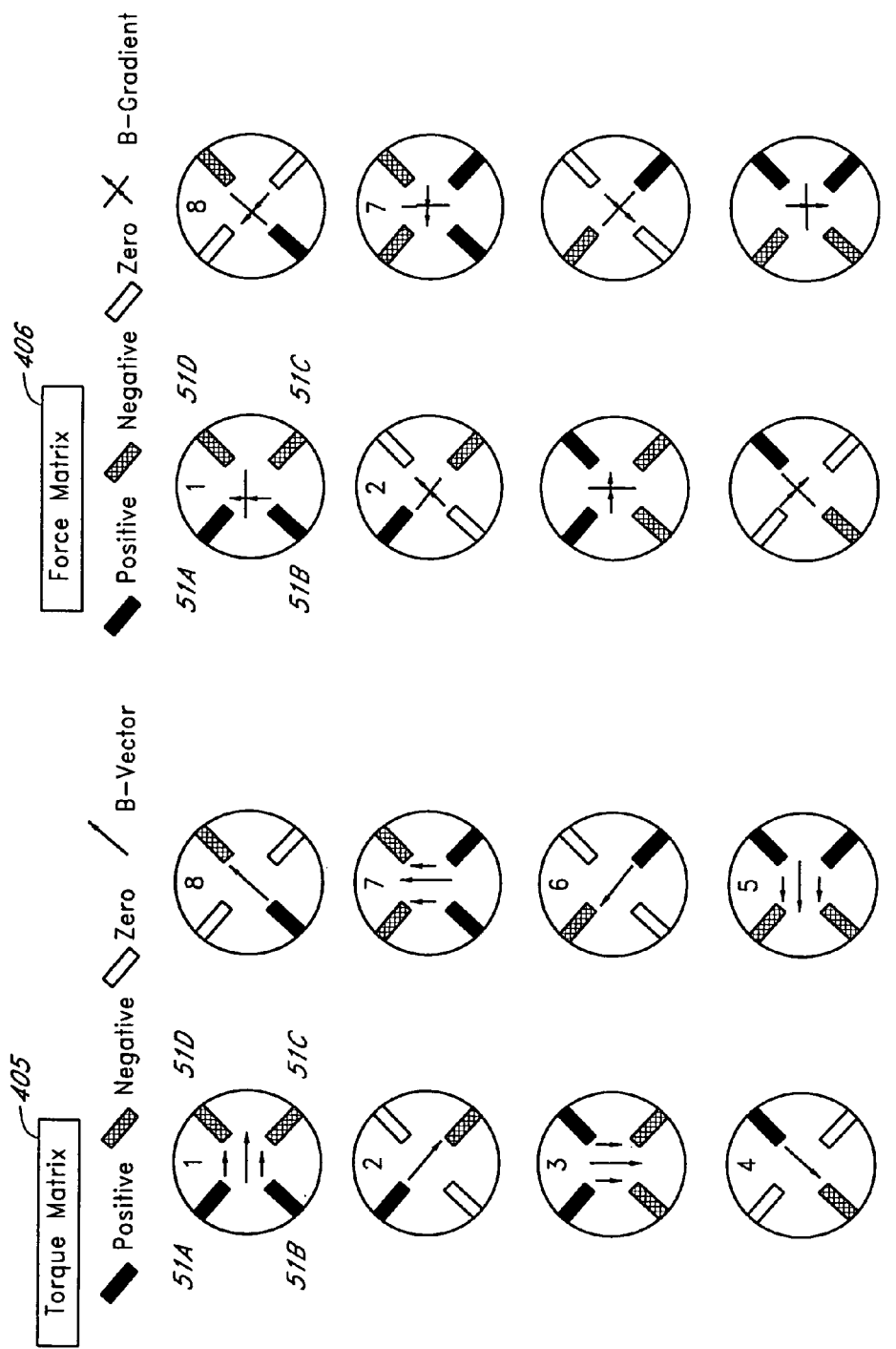
FIG. 31C illustrates the torque matrix used by the CGCI controller.
FIG. 31D illustrates force matrix used by the CGCI controller.

The coil current polarities and magnitudes are set to produce the desired field directions for the torque and force fields. The torque field generating combinations uses an adjacent coil current direction such that the B-vector flows from core to core aiding each other. The coils 51A, 51B, etc., are viewed as if connected in series linked by a common magnetic field as shown in FIG. 30A. The force field generating coil combinations uses an adjacent coil circulating their current such that they work against each other as shown in FIG. 31C. There are 64 combinations of positive and negative current flow polarities for the six coil design. The 2D baseline configurations 50 of four coils can have 16 combinations, half of them generate torque fields, the other half are force gradient configurations. Once the coil/polarity combinations are defined, they can be grouped into a set of matrixes according to above rules. Torque and force matrixes are extracted according to four coil and three coil groups associated with virtual 2D planes as follows: Coils 15AT, 51DT, 51B and 51D form a four-coil group with 16 polarity combinations. This can be considered an approximation of the four coil XY plane baseline design from which the six coil configuration through topological transformations.

The coils 51AT, 51DT, 51A, and 51D form another group on a plane rotated 90° from the group above. Again there are 16 combinations for two/two sets of torque/force matrixes. The third group is formed as two triangular "side plane" combinations of 8 and 8 combinations for two/two sets of torque/force matrixes, (shaped magnetic field 417).

Selecting the right combination of coils 51X and current polarities from each of these virtual planes is performed by the computer 527 and algorithm 528 by applying the superposition rules. The selection occurs when the JS 900 is activated. As shown by previous Figures in deriving the 3D six coil geometry, there is always a coil/polarity combination set for the desired direction within the magnetic boundary. In case of possible multiple selection for the same mode and direction, the algorithm 528 selects a single combination based on possible combinations available for anticipated movement in the same direction and in accordance with the rules of optimal power setting.

FIG. 31C shows a simplified example by using the XY plane to illustrate the control scheme of the CGCI apparatus 1500. The case illustrated by FIG. 30C is a demonstration of the control requirements of a torque field rotation of the catheter tip 377 around the XY plane. The graphic representation shows the coil current polarity selection and actual control of the coil currents to achieve a continuous rotation without changing the field intensity. The torque matrix is shown in FIG. 30C and when the "fire" push-button is released and the JS 900 is turned right, the B-vector torque field rotates clockwise going through the following steps: the catheter tip 377 located in the XY plane (shown in case 1) facing in the +X direction and if the operator wishes to rotate the tip 377 in the negative rotational −Y and continue with the rotation over 360°. To achieve such condition, the CGCI controller 501 brings the field up in the +X direction by increasing the four coil 51X currents to 100% in positive polarity shown in 30C, case 1. Reducing coil current 51B and 51D to zero causes the field to rotate toward the 45° line, and the catheter tip 377 reaches its position as shown in 30C, case 2. Reversing polarity in the coils 51B and 51D rotates the field and the catheter tip 377 toward the −90° line. When the 51D current is equal −100%, the field faces in the −Y direction, see

30C, case 3. Reducing the coil current of 51A and 51C, causes the field to rotate to −135° degree, see 30C, case 4. By increasing the current in coils 51A and 51C in the reverse direction, the field rotates to the 180° position, see 30C, case 5. By reducing the coil current 51B and 51D back to zero, the field rotates to −225°, see 30C, case 6. By increasing the coil current 51B and 51D to positive 100% the field is set to −275°, see 30C; case 7.

Reducing current 51A and 51C down to zero causes the field to point to the 315° line, see 30C, case 8. The rotational circle is completed by turning to FIG. 30C, case 1. All the rotational steps are reached smoothly with continuous control of the coil current oscillating from −100% to 100% through zero, the central slope between the 0 to ±100% coil currents is not a linear function of the coil current but follows an inverse cosine function.

$$\theta = \frac{1}{2}\cos^{-1}\frac{I_{Coil}}{I_{100\%}} \quad (420)$$

where θ is the B vector rotation angle, I coil is actual coil current, and I 100% is the coil current of full field strength.

FIG. 31D shows the control scheme used in the force mode as described in connection with FIG. 30C. The force matrix used for setting a coil/polarity combination shown above in describing 30C apply and the same regulation circuits can control the current magnitudes.

Figure 32:
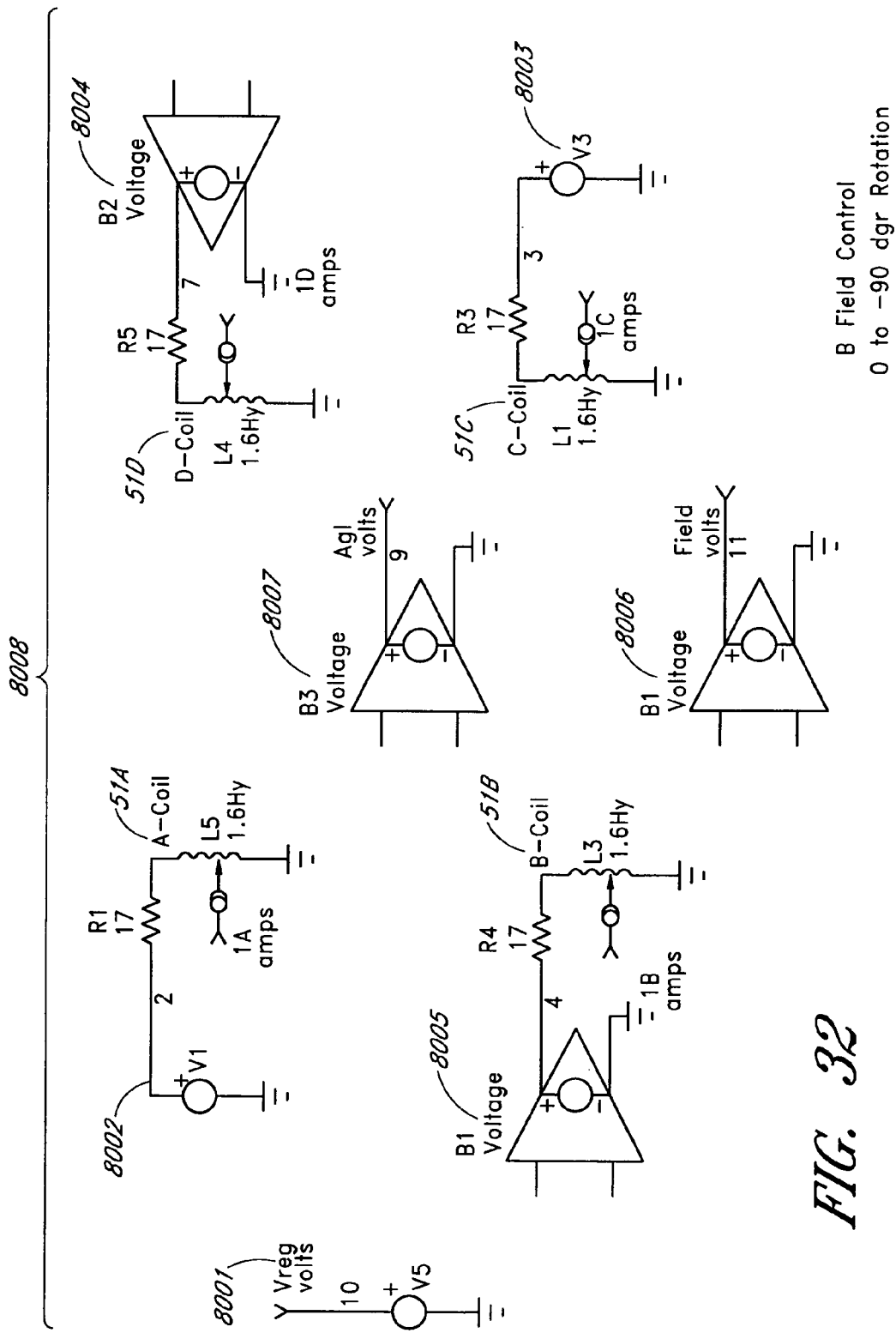
FIG. 32 shows amplifier block diagrams.
Figure 32A:
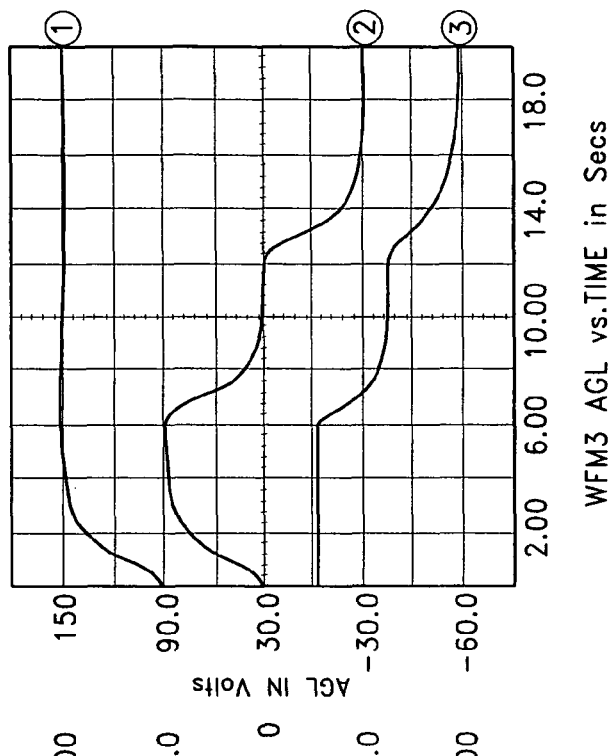
FIG. 32A provides graphs showing time versus amperes in the coils.
Figure 32B:
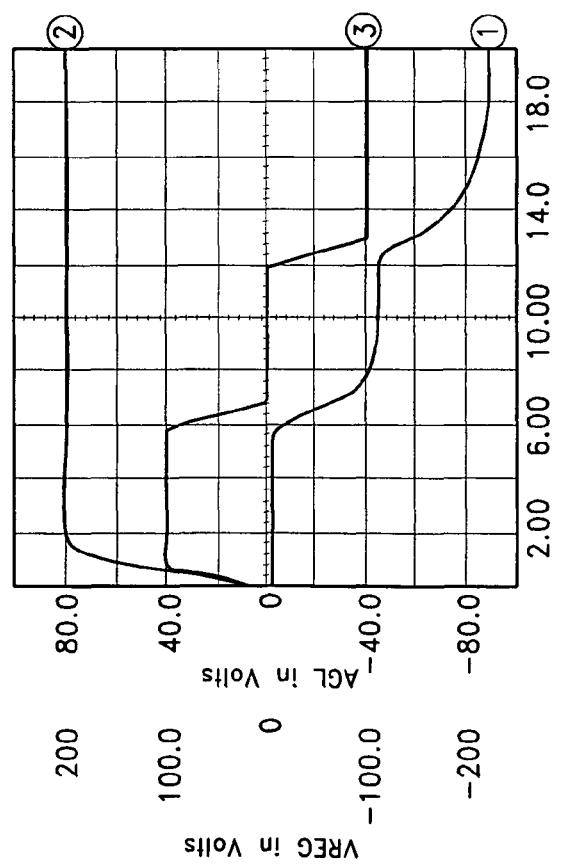
FIG. 32B provides graphs showing time versus voltage across the coils.

FIGS. 32, 32A, 32B, and 32C show the CGCI 1500 low level logic simulation of the magnetic circuit 400. The torque angle control circuit real time behavior is simulated using SPICE for the first −90° rotation, while the coil winding parameters are R=1.7Ω and L=1.6H and the inverse cosine function 420 is also used. The case shown by circuit analysis in FIG. 32 is a demonstration of how the CGCI controller 501 and its algorithm performs the desired position change of the operator input 500 and its mechanical movement by the JS 900 so as to simulate this change on the low level logic and the virtual tip 905 prior to initiating the power level of the DC amplifier 525 and its coil counterpart 51A etc. In this simulation, V5 is the regulator 8001 controlling the power supply voltage of coil 51D and coil 51B (B2 8004 and B1 8005 respectively). V5 8001 is the control variable in this simulation, and it is selected to the coil currents in 51B and 51D by the torque matrix step FIG. 31C, 1, 2, and 3. The currents of the 51B and 51D go up to +100% together with 51A and 51C, but then 51D and 51B go through zero)(−45°) and reverse polarity to −100% (−90°) while 51A and 51C are constant. The regulator 8001 output voltage profile shown in FIG. 32B forces coil current 51B and 51D to reverse after dropping to zero. V1 8002 is the power supply for coil 51A. Initially it ramps up to full voltage together with the V5 8001 regulator, and stays at 100% current for this particular simulation for the rest of the rotational cycle. Because the rotational matrix is already set, coil 51A will not vary magnitude or polarity during the rotation.

V3 8003 is the power supply of coil 51C which functions the same way as V1 8002 coil 51A above. The control matrix causes it to be same polarity and magnitude as V1 8002. B2 8004 is the power supply for coil 51D and its voltage follows V5 8001 regulator coil, as designed by the scale model 50. B1 8005 is the power supply for coil 51B and also follows the regulator 8001 command. B4, 8006 computes the B-field strength in percent. It takes the current of coil 51A (equal to 51C) and defines B in percent (%) by using the following equation.

$$B_\% = 100 \cdot \sin\left[\frac{I_A}{100}\right] \quad (421)$$

where $I_A$ varies from 0 to 100.

B3 8007 computes the rotational angle according to the following equation:

$$\theta = -\frac{1}{2}\cos^{-1}\left[\frac{I_D}{I_A}\right] \quad (422)$$

where $I_A$ and $I_D$ are coils 51A and 51D currents. The rotational procedure uses the regulator 8001 which controls the four coils to rise to full current as (shown by the parameters R=1.7Ω and L=1.6H), V Reg 8001 rises to 100%, current 51IA, 51IB, 51IC, and 51ID rise together according to L/R time constant (see FIG. 31C), and lines up to +X at zero degree phase. The regulator controls 51IB and 51ID together to zero starting at 6 seconds (FIG. 31C). 51IA and 51IC remain constant. The phase rotates to −45° while the field strength remains constant. The regulator commands current of coils 51IB and 51ID to reverse starting at 12 seconds (see FIG. 31C. The phase angle rotates to −90° (see FIGS. 31A and 31B) while the field strength remains constant.

The system can also proceed a B-field rotation as shown in case 31C step 4 and 5 to rotate −90° clockwise. The matrix changes the current control sequence so that coil 51A and 51C go through the polarity reversal. In summary, FIGS. 31, 31A, 31B and 31C show the control scheme of the controller which provides a low level simulation of the magnetic circuit 400 and provides, as an additional safety measure, verification of the joystick 900 movement prior to activation of the power level of the coils.

Figure 33:
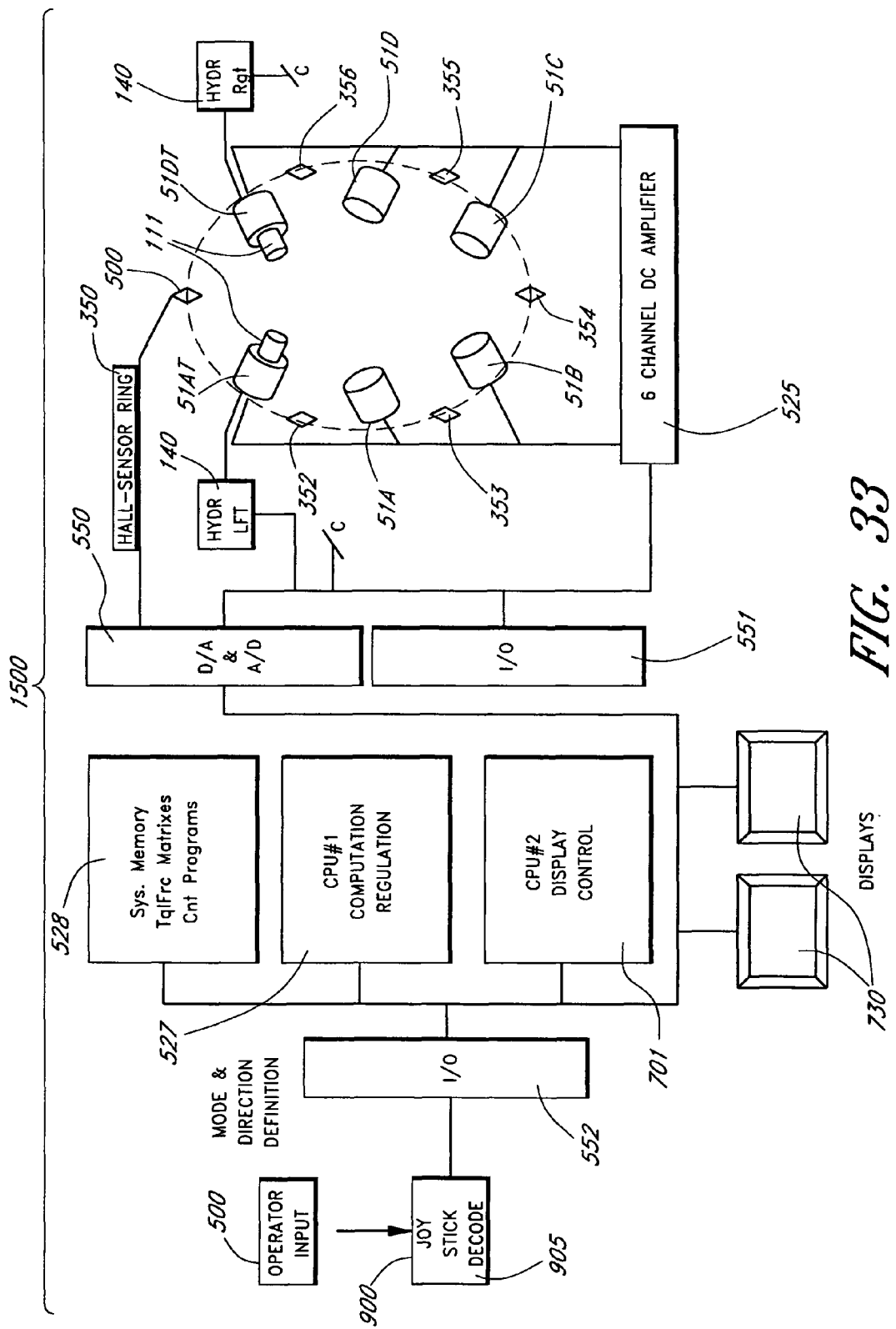
FIG. 33 is a block diagram of one embodiment of the CGCI apparatus with magnetic sensors.

FIG. 33 shows the CGCI 1500 top architecture showing the major elements comprising the controller 501 of the magnetic circuit. The controller 501 includes a system memory, a torque/force matrix algorithm residing in 528 and a CPU/computer 527. The CPU/computer such as PC 527 provides computation and regulation tasks. FIG. 33 further shows the six coil electromagnetic circuit formed out of coils 51A, 51B, 51C, 51D, 51AT and 51DT and the magnetic field sensors (MFS) 351, 352, 353, 354, 355 and 356 such as Hall sensor ring 350 mounted on an assembly forming the X, Y, and Z axis controls. A D/A converter 550 and an I/O block 551 provide communication between the controller 501 and the coils 51A and the hydraulically-systems 140. The six channel DC amplifier 525 provides current to the coils.

FIG. 33 shows the relationship and command structure between the joystick 900, the virtual tip 905, and the CPU 701. The CPU 701 displays control conveying real time images generated by the X-ray, radar 1000, or other medical imaging technologies such as fluoroscopy, MRI, PAT SCAN, CAT SCAN, etc., on a display 730. A flow diagram of the command structure of the control scheme is shown by the use of the 2D virtual plane coil polarity matrixes. By assigning the coil position and polarity elements to the directions of torque rotation and force field gradient on each 2D plane of a six coil cluster 414, a computer program such as MathLab or Math Cad is able to sift through the combination matrixes and compute the proper combination for the six coil current polarities and amplitudes. In one embodiment, a boundary condition controller is used for regulating the field strength 405 and field gradient 406 in the effective region. The controller 501 computes the fields in the neighborhood of the catheter tip 377 and as defined by the fields on the 2D planes in the effective area. Rules for computing the fields with rotated coil on the surface of the sphere are given by Equations 405 and 406 and the topological transformation 407 for the six coil CGCI 1500 configuration.

In one embodiment, look-up tables are used as a reference library for use by the controller 501. Lookup tables of the setting of various scenarios of force as well as torque position and magnitude allow the controller 501 to use a learning algorithm for the control computations. The look-up tables shorten the computational process for optimal configuration and setting of the coil currents and pole positions. The D/A and A/D system 550 allows the connection of voltage and current measuring instruments as well as input from the magnetic field sensor (MFS) 350 array, the MFS 351, 352, 353, 354, 355 and 356. The magnetic field sensor measuring the boundary plane field strength allows the CGCI to use a low-level logic algorithm to compute the positions, settings, coil currents, etc. The low-level simulation is performed prior to activating the power section of the CGCI apparatus 1500, thus, providing a "soft" level check prior to action performed by actual machine. The two-level control architecture that starts with low-level simulation architecture of low-level simulation allows the surgeon or operator of the CGCI apparatus 1500 to test each movement prior to actually performing the move.

FIGS. 34, 35, and 36 illustrate the field regulator loop outlined in FIG. 33 using the Hall effect ring 350. FIG. 34 shows the generator interface joystick 900 and its virtual tip 905 where the user commands are initiated. In one embodiment, movement of the catheter tip 377 is initiated as a field having a vector with components Bx, By, and Bz, for torque control and a vector dBx,y,z for force control are computated. The B-field loop with its functional units, include a Φ regulator 901.3. Hall effect sensors 351X, 352X, 353X, 354X, 355X, 356X, and 351Y-356Y as well as 351Z-356Z measure the B and dB fields. Computation regulators 527.1-527.6 calculate position, desired position (DP) change and the desired field and field gradients. The coil current 51A, 51B, 51C, and 51D are set and the catheter tip 377 position is changed from actual position 9040 to desired position 9060.

In one embodiment, the movement of the catheter tip 377 is seen in real time by the operator 500 while observing the display 730.

A visual display of the magnetic fields can be generated using 3-axis Hall sensors 351-356 placed on the 2D planes.

The "fire" push-button on the JS 900 selects torque or force modes for "rotate" or "move" commands. The magnitude and direction of the torque and force are determined by user inputs to the JS 900.

In one embodiment, the system sets the maximum torque and force by limiting the maximum currents.

In one embodiment, catheter movement is stopped by releasing the JS 900. The fields are held constant by "freezing" the last coil current values. The magnetic tip 377 is held in this position until the JS 900 is advanced again. The computer 527 also memorizes the last set of current values. The power can be turned off for radar positioning, Hall effect recalibration of the sensor array and the system returns to the previous coil current values. The memorized coil matrix sequences along the catheter movement creates a computational track-record useful for the computer to decide matrix combinations for the next anticipated movements.

In one embodiment, the magnetic field is sensed by 3-axis instrumentation-quality Hall sensors 351-356 placed in the centers of the 2D planes (six sensors all together). Each sensor 35X x, y, z provides the Bx, By, and Bz components of the field sufficient to describe the 2D boundary conditions numerically. The measurements are used to calculate B magnitude and angle for each 2D plane. From the fixed physical relationship between the plane centers, the field can be calculated for the catheter 377. As shown in FIG. 35, coils 51A, 51B, 51C, 51D forms a 2D virtual plane with respect to the 3-axis Hall devices wherein Hall sensors 351X identify Bx, By, and Bz relative to the X axis, similarly 351Y identify Bx, By, and Bz relative to the Y axis, and 351Z identify Bx, By, and Bz relative to the Z axis respectively.

In one embodiment, the Hall sensors 351X, 351Y, and 351Z produces three analog outputs 907. One for each component, for the A/D converter 550 shown in FIG. 33. This data is used to compute the superimposed fields in the 3D region of the catheter 377 (effective region 419).

Each Hall sensor 351x, y, and z is a multi-axis sensor such as the one manufactured by F.W. Bell having three individual Hall elements oriented in mutually perpendicular planes. This allows the sensors to produce voltages proportional to the three orthogonal components (Bx, By, Bz) 907 of a magnetic flux in any direction. Thus, the sensors 351 can be permanently mounted or arbitrarily oriented to sense fields in any direction. The magnitude of the flux vector, B 907 can be found using the following relation:

$$B = B_x^2 + B_y^2 + B_z^2$$

The flux direction relationship is formed by using the above relationship of angle.

$$a = \cos^{-1} B_x/B, b = \cos^{-1} B_y/B, d = \cos^{-1} B_z/B$$

Where a 904.1, b 904.2, d 904.3 are angles between B, Bx, By, Bz respectively.

The Hall sensors operate in an environment of ±5° C. temperature variation and 0 to ±5 kGauss field strength range.

The CGCI controller 501 generates a Bx, y, z, field readout error which is approximately 2.5% for all causes including linearity, matching and various temperature drifts. Some of the temperature drifts can be compensated for and residual flux errors can be readily offset. These error correction techniques reduce the total readout error to approximately 1%. This error is inconsequential for the magnetic field displays of the manual man-in-the-loop control mode, and can be tolerated for a fully closed loop system.

Another embodiment of the CGCI controller 501 uses close loop control wherein the biasing of the field is performed without the visual man-in-the-loop joystick feedback, but through position control and a digital "road-map" based on a pre-operative data using such as the MRI, PET SCAN, etc. The digital road map allows the CGCI controller 501 and the radar 1000 with aid of the fiduciary markers 700AX, 700BX to perform an autonomous movement from the point 9040 (actual position of the catheter tip 377) to desired position (DP) 9060 based on closed loop control.

In one embodiment, the CGCI system has magnetic capability for torque control up to 1.6 Tesla, and force control up to 1.7 Tesla/meter. Precision catheter 377 positioning is based on control of the direction and magnitude of both type fields within these ranges. The manual control with the man-in-the-loop provides a relatively coarse control of these values. The JS 900 visual navigation is based on imaging and navigation operator skill. The precision computer-aided catheter guidance system uses actual magnetic field regulation for precision catheter positioning.

Field regulation 740 is based on providing the coil current control loops used in the manual navigation system within the field regulating loop as a minor loop, and to be a correction and/or supervisory authority over machine operation. Control of B-field loops is defined by the joystick 900/905 and its associated field commands 900.1. The closed servo loop uses position data from the radar 1000 to allow the servo control loop to be closed and is used as the primary loop control.

FIG. 34 further shows field regulation 740. The field regulator 740 receives a command signal field 900.1 from the radar 1000 position 9040 and the JS 900 new position 9060 data from the computation unit 528, which generates a Bx, y, z vector for torque control, and the dBx, y, z vector gradient for force control. This position computational value identified in FIG. 34 allows the Φ regulator 901.3 to receive two sets of field values for comparison.

The present value (actual value 9040) of Bcath and dBcath at the catheter tip 377 are calculated from the five 3 axis Hall effect outputs B1x, y, z 351 through B5x, y, z 356.

The new field values for the desired position (DP) 9060 Bx, y, z 907 and dBx, y, z 907 to advance the catheter tip 377 are generated in the CGCI controller 501. The difference is translated to the Matrix block 528 for setting the coil currents and polarities.

In one embodiment, the matrix 528 issues the current reference signals to the six regulator CREG1 527.1 through CREG 527.6. The regulators 750 drive the six-channel power amplifier 525 to obtain the desired coil currents.

In one embodiment, the precision of field regulation is determined by the precision of the field measurement. The Hall effect devices 351-356 have about 1% error under the operating room environment. The CGCI controller 501 calculates the catheter position error (PE) in actual distance for a particular case of a catheter tip 377.

In one embodiment, the torque on a permanent magnet in field B 405 is:

$$T_m = M \cdot B \cdot A_m \cdot L_m \cdot \sin(\theta)$$

where M is the dipole magnetization vector, and B is the field density vector around the dipole. $A_m$ is the magnet cross section, and $L_m$ is its length. For B-0.15 Tesla the calculated bending arm is $L_{bend}$=38 mm. Assuming B is measured with 1% error, $T_m$ will have a 1% error.

Therefore, the position error due to measuring error of 1% is $$L_{error} = \frac{L_{bend}}{100} = 0.38 \text{ mm or } 0.015 \text{ inch}$$

A position error of less than 0.015 will leave room for other computational errors, and the regulation scheme provides an expectation of 22 mils. (0.22 inch) error.

Many other variations are possible within the scope of the present invention. For example, the modulation of the electromagnets can be controlled in such a way as to cause a vibratory or pulsating motion of the tip to aid in crossing plaque. The responsive tip(s) can be electromagnetic rather than permanent magnets. The magnetic field external to the body can be generated by a permanent magnet or magnets. The control of the external magnetic field can be accomplished by manually administering the field generating devices. AC induction with its associated magnetic effects can be used by causing a coil or coils wound around the tip to respond to an impressed time variant field. Materials with curie temperatures within a few degrees of body temperature can be used as magnetic flux switches for selective tip control by irrigating them with fluids having appropriate temperatures; electrostatic phenomena can enhance magnetic effects. Artificial intelligence can replace the operator control for producing command inputs; an expert system can replace or augment operator inputs. The apparatus can be used to incubate various body cavities and organs other than the heart. The apparatus can be used for human and animal procedures such as egg harvesting and embryo implantation. The responsive tip can be attached to a coherent fiber optic bundle to provide viewing of internal structures with unprecedented maneuverability; internal radioisotope therapy can be precisely performed by delivering a palletized source directly to a tumor using a guided catheter. Internal tissue samples can be obtained without major surgery; a fiber optic light guide equipped with a responsive tip can be accurately positioned to deliver last light to a specific internal location without major surgery. Thus, the scope of the invention is limited only by the claims.

What is claimed is:

1. An apparatus for controlling the movement of a catheter inside a body of a patient, comprising:
a magnetic field source for generating a magnetic field, said magnetic field source comprising:
a first coil corresponding to a first magnetic core and a second coil corresponding to a second magnetic core, a third magnetic core corresponding to a third coil, and a fourth magnetic core corresponding to a fourth coil, wherein said first, second, third and fourth cores and coils are arranged in a first semi-spherical symmetry cluster,
a fifth coil corresponding to a fifth magnetic core, a sixth coil corresponding to a sixth magnetic core, a seventh coil corresponding to a seventh magnetic core, and an eighth coil corresponding to an eighth magnetic core, wherein said fifth, sixth, seventh and eighth poles and coils are arranged in a second semi-spherical symmetry cluster; and
wherein at least said first magnetic core of said first semi-spherical symmetry cluster is moveable with respect to said second magnetic core of said first semi-spherical symmetry cluster and said first magnetic core extends and retracts relative to said first coil; and
a servo system controller configured to control extension and retraction of at least said first magnetic core to position said first magnetic core of said first semi-spherical symmetry cluster, said servo system controller configured to receive position data regarding said current position of said distal end of a catheter, said servo system controller further configured to control currents in said first, second, third, fourth, fifth, sixth, seventh and eighth coils to control a movement of a distal end of a catheter to a desired position with torque control fields according to the following equation:

$$B_{T_q} = B_{XY} \cdot \cos(\theta)$$

and with force control fields according to the following equation:

$$\frac{dB}{ds} = \frac{dB_{XY}}{ds} \cdot \cos(\vartheta)$$

where $B_{XY}$ is the field in an XY plane, and θ is angle of spherical rotation of the first, second, third, fourth, fifth, sixth, seventh and eighth coils from the XY plane;
said distal end responsive to said magnetic field to move to said desired position.

2. The apparatus of claim 1, said distal end comprising one or more magnetic field sensors.

3. The apparatus of claim 1, said distal end comprising one or more magnetic field sensors for providing sensor data to said system controller.

4. The apparatus of claim 1, further comprising an operator interface unit.

5. The apparatus of claim 1, wherein said servo system controller comprises a correction factor that compensates for a dynamic position of an organ, thereby offsetting a response of said distal end to said magnetic field such that said distal end moves in substantial unison with said organ.

6. The apparatus of claim 5, wherein said correction factor is generated from an auxiliary device that provides correction data concerning said dynamic position of said organ, and wherein when said correction data are combined with measurement data derived from said sensory apparatus to offset a response of said servo system controller so that said distal end moves substantially in unison with said organ.

7. The apparatus of claim 6, wherein said auxiliary device is at least one of an X-ray device, an ultrasound device, and a radar device.

8. The apparatus of claim 1, wherein said servo system controller includes a Virtual Tip control device to allow user control inputs.

9. The apparatus of claim 1, wherein said first magnetic core is extended and retracted by a hydraulic piston.

10. The apparatus of claim 1, further comprising:
first controller to control said first coil; and
a second controller to control said second coil.

11. The apparatus of claim 10, wherein said first controller receives feedback from a magnetic field sensor.

12. The apparatus of claim 11, wherein said magnetic field sensor comprises a Hall effect sensor.

13. The apparatus of claim 1, wherein said system controller coordinates flow of current through said first and second coils according to inputs from a Virtual tip.

14. The apparatus of claim 13, wherein said Virtual Tip provides tactile feedback to an operator.

15. The apparatus of claim 13, wherein said Virtual Tip provides tactile feedback to an operator according to a position error between an actual position of said distal end and a desired position of said distal end.

16. The apparatus of claim 13, wherein said system controller causes said distal end to follow movements of said Virtual Tip.

17. The apparatus of claim 13, further comprising:
a mode switch to allow a user to select a force mode and a torque mode.

18. An apparatus for controlling the movement of a catheter having a distal end responsive to a magnetic field and configured to be inserted into the body of patient, comprising:
a magnetic field source for generating a magnetic field outside the body said magnetic field source comprising:
a first coil corresponding to a first magnetic core and a second coil corresponding to a second magnetic core, a third coil corresponding to a third magnetic core, and a fourth coil corresponding to a fourth magnetic core, wherein the first, second, third and fourth coils and cores are arranged in a first semi-spherical symmetry cluster,
a fifth coil corresponding to a fifth magnetic core, a sixth coil corresponding to a sixth magnetic core, a seventh coil corresponding to a seventh magnetic core, and an eighth coil corresponding to an eighth magnetic core, wherein the fifth, sixth, seventh and eighth coils and cores are arranged in a second semi-spherical symmetry cluster;
a hydraulic system to extend and retract at least the first magnetic core of said first semi-spherical symmetry cluster with respect to said second magnetic core of said first semi-spherical symmetry cluster and with respect to the first coil to control a shape of a magnetic field produced by said magnetic field source with respect to the body;
a location system to measure a current location of said distal end of said catheter;
a sensor system to measure positions of a plurality of fiduciary markers;
a user input device for inputting commands to move said distal end; and
a servo system controller configured to receive said current position data of said distal end of said catheter, said servo system controller further configured to control said magnetic field source in response to inputs from said user input device, said location system, and said magnetic sensors, said system controller configured to control currents in said first, second, third, fourth, fifth, sixth, seventh and eighth coils to control a movement of a distal end of said catheter to a desired position with torque control fields according to the following equation:

$$B_{Tq} = B_{XY} \cos(\theta)$$

and with force control fields according to the following equation:

$$\frac{dB}{ds} = \frac{dB_{XY}}{ds} \cdot \cos(\vartheta)$$

where $B_{XY}$ is the field in an XY plane, and $\theta$ is angle of spherical rotation of the first, second, third, fourth, fifth, sixth, seventh and eighth coils from the XY plane; and
wherein said servo system controller is further configured to control said extension and retraction of at least said first magnetic core to position said first magnetic core of said first semi-spherical symmetry cluster.

19. The apparatus of claim 18, said location system comprising an impulse radar.

20. The apparatus of claim 18, said distal end comprising one or more magnets.

21. The apparatus of claim 18, where said servo system controller calculates a position error and controls said magnetic field source to move said distal end in a direction to reduce said position error.

22. The apparatus of claim 18, where said servo system controller integrates a position data of said distal end with a set of fiduciary markers.

23. The apparatus of claim 18, where said servo system controller synchronizes a location of said distal end with a fluoroscopic image.

24. The apparatus of claim 18, further comprising an operator interface unit.

25. The apparatus of claim 18, wherein a correction input is generated by an auxiliary device that provides correction data concerning a dynamic position of an organ.

26. The apparatus of claim 25, wherein said auxiliary device comprises at least one of an X-ray device, an ultrasound device, and a radar device.

27. The apparatus of claim 18, wherein said user input device comprises a virtual tip control device to allow user control inputs.

28. The apparatus of claim 18, further comprising a virtual tip with force feedback.

29. The apparatus of claim 18 wherein a first coil cluster is fitted with shield for flux return.

30. The apparatus of claim 18, further comprising a boundary condition controller, and where computing the fields in the surroundings of the catheter based on the fields on 2D planes.

31. The apparatus of claim 18, wherein a button allows said system controller to switch from torque control to force control.

32. The apparatus of claim 18, wherein said servo system controller is configured to produce coil current polarities and magnitudes are generated to produce desired field directions for torque and force field is established.

33. The apparatus of claim 18, wherein a low level logic simulation of action is provided.

\* \* \* \* \*